(12) United States Patent
Brooks et al.

(10) Patent No.: US 10,453,572 B1
(45) Date of Patent: Oct. 22, 2019

(54) SYSTEM AND METHOD FOR A HOSPITAL CART

(71) Applicant: Capsa Solutions, LLC, Portland, OR (US)

(72) Inventors: Richard Jason Brooks, Huntersville, NC (US); Joseph R. D'Amico, Fort Mill, SC (US); Stephen C. Torbett, Lake Wylie, SC (US); Derek J. Nash, Greer, SC (US)

(73) Assignee: Capsa Solutions, LLC, Portland, OR (US)

( * ) Notice: Subject to any disclaimer, the term of this patent is extended or adjusted under 35 U.S.C. 154(b) by 1035 days.

(21) Appl. No.: 13/782,841

(22) Filed: Mar. 1, 2013

Related U.S. Application Data

(60) Provisional application No. 61/605,716, filed on Mar. 1, 2012.

(51) Int. Cl.
*G16H 40/63* (2018.01)

(52) U.S. Cl.
CPC .................................. *G16H 40/63* (2018.01)

(58) Field of Classification Search
None
See application file for complete search history.

(56) References Cited

U.S. PATENT DOCUMENTS

| | | |
|---|---|---|
| D375,601 S | 11/1996 | Myers |
| D376,459 S | 12/1996 | Myers |
| D389,917 S | 1/1998 | Hornback et al. |
| 6,480,762 B1 | 11/2002 | Uchikubo et al. |
| D482,172 S | 11/2003 | Johnson |
| D517,768 S | 3/2006 | Arceta |
| D518,267 S | 3/2006 | Arceta |
| 7,155,306 B2 | 12/2006 | Haitin et al. |
| D539,794 S | 4/2007 | Rossini et al. |
| D540,002 S | 4/2007 | Perrier |
| D543,000 S | 5/2007 | Perrier |
| D544,962 S | 6/2007 | Diener et al. |
| D548,918 S | 8/2007 | Nussberger |
| D552,324 S | 10/2007 | Perrier |
| 7,594,668 B2 | 9/2009 | Arceta et al. |

(Continued)

FOREIGN PATENT DOCUMENTS

WO 2004/076604 A2 9/2004

*Primary Examiner* — Ryan A Jarrett
(74) *Attorney, Agent, or Firm* — Standley Law Group LLP; Adam J. Smith; Jeffrey S. Standley

(57) ABSTRACT

A medical cart includes a controller, display unit and display application that enables a user to select controls to specify different functions to be executed by the controller and to specify different status data to be displayed. A system for providing remote services to the medical cart includes a database and a server, both of which are located remotely from the cart. The database includes a plurality of applications. The server includes a data collection unit to collect data associated with the medical carts, and an analysis unit to analyze the collected data to detect a condition associated with the cart. In response to the detected condition, the control unit executes one or more of the applications, determines parameters to be communicated to the cart, automatically downloads one or more applications to the cart, and/or activating a web page having information to a user displaying information about the cart.

15 Claims, 25 Drawing Sheets

(56) References Cited

U.S. PATENT DOCUMENTS

| | | | |
|---|---|---|---|
| 7,612,544 B2 | 11/2009 | Rossini | |
| D606,202 S | 12/2009 | Banryu | |
| D626,235 S | 10/2010 | Smith et al. | |
| D632,797 S | 2/2011 | Ross et al. | |
| D648,855 S | 11/2011 | Smith et al. | |
| D650,142 S | 12/2011 | McRorie | |
| D652,521 S | 1/2012 | Ross et al. | |
| D652,936 S | 1/2012 | Ross et al. | |
| 8,109,527 B2 | 2/2012 | Bustle et al. | |
| D657,470 S | 4/2012 | Schon et al. | |
| 8,196,939 B2 | 6/2012 | Bustle et al. | |
| 8,215,650 B2 | 7/2012 | Arceta et al. | |
| 8,240,684 B2 | 8/2012 | Ross et al. | |
| D670,062 S | 10/2012 | Sonnendorfer | |
| D670,063 S | 10/2012 | Sonnendorfer | |
| 8,286,977 B2 | 10/2012 | Butler et al. | |
| D681,303 S | 4/2013 | Sonnendorfer | |
| D687,147 S | 7/2013 | Yoshida | |
| D696,783 S | 12/2013 | Chung et al. | |
| 8,651,594 B2 | 2/2014 | Jones et al. | |
| D700,706 S | 3/2014 | Molter | |
| 8,677,911 B2 | 3/2014 | McRorie | |
| D702,842 S | 4/2014 | Hyde et al. | |
| 8,714,569 B2 | 5/2014 | Lu et al. | |
| D708,341 S | 7/2014 | Ikegame et al. | |
| D712,540 S | 9/2014 | Hansen et al. | |
| D722,696 S | 2/2015 | Blomquist et al. | |
| D730,011 S | 5/2015 | McRorie et al. | |
| D760,390 S | 6/2016 | Blomquist et al. | |
| D764,669 S | 8/2016 | Birath et al. | |
| D769,448 S | 10/2016 | Adams et al. | |
| D776,279 S | 1/2017 | Newman et al. | |
| D777,927 S | 1/2017 | Choudhary | |
| D807,510 S | 1/2018 | Newman et al. | |
| D824,521 S | 7/2018 | Adams et al. | |
| D825,763 S | 8/2018 | Lim et al. | |
| D827,139 S | 8/2018 | Henderson et al. | |
| D836,781 S | 12/2018 | Meurer et al. | |
| 2004/0179332 A1* | 9/2004 | Smith | A61B 90/36 361/679.41 |
| 2004/0186357 A1* | 9/2004 | Soderberg | A61B 5/00 600/300 |
| 2004/0262867 A1 | 12/2004 | Arceta et al. | |
| 2005/0065817 A1 | 3/2005 | Mihai et al. | |
| 2005/0159784 A1 | 7/2005 | Arceta | |
| 2006/0142657 A1* | 6/2006 | Quaid | A61B 17/1764 600/424 |
| 2008/0146922 A1* | 6/2008 | Steins | A61B 8/546 600/437 |
| 2008/0252045 A1 | 10/2008 | Rossini et al. | |
| 2009/0015116 A1 | 1/2009 | Arceta et al. | |
| 2009/0212670 A1 | 8/2009 | Bustle et al. | |
| 2009/0319079 A1 | 12/2009 | Arceta et al. | |
| 2010/0213679 A1 | 8/2010 | Smith et al. | |
| 2011/0247903 A1* | 10/2011 | Boukhny | B60B 33/0042 188/68 |
| 2011/0272902 A1 | 11/2011 | Arceta et al. | |
| 2012/0126503 A1 | 5/2012 | Butler et al. | |
| 2012/0203377 A1* | 8/2012 | Paydar | G01K 3/005 700/232 |
| 2012/0212116 A1 | 8/2012 | McRorie et al. | |
| 2012/0236496 A1 | 9/2012 | McRorie | |
| 2012/0274196 A1 | 11/2012 | Arceta et al. | |
| 2013/0085615 A1* | 4/2013 | Barker | A61G 10/00 700/277 |
| 2013/0194072 A1* | 8/2013 | Kim | G08B 5/36 340/6.1 |
| 2013/0200579 A1 | 8/2013 | Abernethy et al. | |
| 2013/0300075 A1 | 11/2013 | Arceta et al. | |
| 2013/0307237 A1 | 11/2013 | Chen | |
| 2014/0084558 A1 | 3/2014 | Ergun et al. | |
| 2014/0218282 A1 | 8/2014 | Hung | |
| 2014/0265193 A1 | 9/2014 | Stark | |
| 2015/0245708 A1* | 9/2015 | Abernethy | B62B 3/02 361/679.4 |

* cited by examiner

SYSTEM AND METHOD FOR A HOSPITAL CART

RELATED APPLICATIONS

This is a regular-filed application which is based on and claims priority to U.S. Provisional Patent Application Ser. No. 61/605,716, entitled "System and Method for a Hospital Cart," which was filed on Mar. 1, 2012, the entire disclosure of which is hereby expressly incorporated by reference herein.

TECHNICAL FIELD

The disclosure relates generally to hospital carts and other healthcare delivery systems and, more particularly, to the configuration, operation and maintenance of computerized hospital carts.

BACKGROUND

Generally, computerized hospital cart functions are controlled by an embedded microcontroller embedded within the cart. This type of architecture presents a variety of constraints and problems. In particular, the user interface (UI) for manually configuring and adjusting cart function parameters on the cart itself, such as lift speed, personal identification number (PIN) codes or other user access, identification and authentication, cart name or designation, timeouts, caster locks, drawer locks, drawer accessibility, etc., must be installed on the end-user's computer, where the end-user may be a healthcare provider or other healthcare entity that utilizes the hospital cart, such as a hospital, system of hospitals, hospital floor, hospital ward, doctor's office, homecare provider, long term care provider, ambulatory surgery centers, clinics, school health facilities, penitentiary health facilities, etc. The end-user's computer may be provided as a laptop, thin client, zero client. The end-user's computer, however, while having functionality with the cart and its microcontroller, is generally provided as a system remote from the cart and the embedded microcontroller. In some cases an end-user's computer is not utilized with the hospital cart at all.

Further, additional drivers must be installed on the end-user's computer in order for the UI to connect to the cart microcontroller via a dedicated connection, such as Universal Serial Bus (USB). Generally, the UI applications and USB drivers are only compatible with computers running a full version of the Microsoft Windows™ operating system.

Where multiple of hospital carts are concerned, fleet management applications are utilized. However, the connection to the end-user's computer is the only means to facilitate the use of fleet management application for each cart, including user access (PIN codes) management and power system management. In addition, there are separate local and fleet management UI applications for user management and power system management. The fleet management applications must be installed on each end user's network servers, such as a hospital system's network servers, which may not be possible depending on particular configuration of the servers and network security policies.

Once a hospital cart has been configured/set up and fielded (e.g., put into use), feature upgrades, or new functions potentially require a complete replacement of the old microcontroller circuit board with a new microcontroller circuit board. To make changes and updates, firmware and software changes have to be performed on a cart-by-cart basis, or require reinstallation of software on hospital servers.

These constraints cause a significant amount of cost and inconvenience to the hospital's Information Technology (IT) staff and other end user personnel, as well as manufacturer service departments, during setup, deployment, and maintenance of the hospital carts.

Existing solutions only attempt to solve some of these problems, but not all, and they require installation of software on the end user's computers and/or servers. These installations often conflict with the end user's other software, computers or network configurations, thereby making them unwieldy or infeasible to implement or maintain in many cases. Other solutions require multiple, inflexible hardware buttons to be installed on the hospital carts to control cart operations, limiting the ability to adjust to changing user needs.

End-users are also tasked with the responsibility of reacting and responding after problems arose instead of proactively, due to lack data visibility and staffing to manage fleets of carts. Further, it is common for end-users to follow less than optimal security practices in managing PIN codes and user access to the cart and/or drawers. Still further, end users often choose to keep cart parameters and settings static and constant, rather than changing them to adapt to changing user, workflow requirements and ergonomics. Lastly, end-users infrequently engage in implementing integrated solutions with their fleet of carts, due to greater planning and resources than many end users can afford.

Thus, there is a need to provide end users with a hospital cart that is more flexible in terms of its configuration, operation and maintenance, while keeping data files on the end-user's computer, such as confidential patient medical data, inaccessible from the hospital cart, and keeping the hospital cart autonomous with respect to the end-user's computer, such that there is no functional interdependence or data-sharing between the hospital cart and the end-user's computer.

DETAILED DESCRIPTION

Disclosed herein is a hospital cart system and method that allows a designated third party (e.g., end user) access to cart data and operations, such as battery usage, memory usage, etc., while segregating and securing patient and/or hospital medical records. Features of the hospital cart may include, but are not limited to, an embedded computer independent of the end-user's computer, a display screen with a dynamic, customizable graphical user interface (GUI), a single platform-based power system with modular output power modules, an open, scalable power and communications bus architecture and intelligent subsystems capable of remote firmware and software updates, including the embedded computer and power systems. Further, a web-based, centrally-hosted and integrated fleet management system with end-user remote access is provided to monitor, configure, analyze, and update hospital carts without requiring installation of any custom software or drivers on the end-user's servers or cart laptops/computers.

Figure 1:
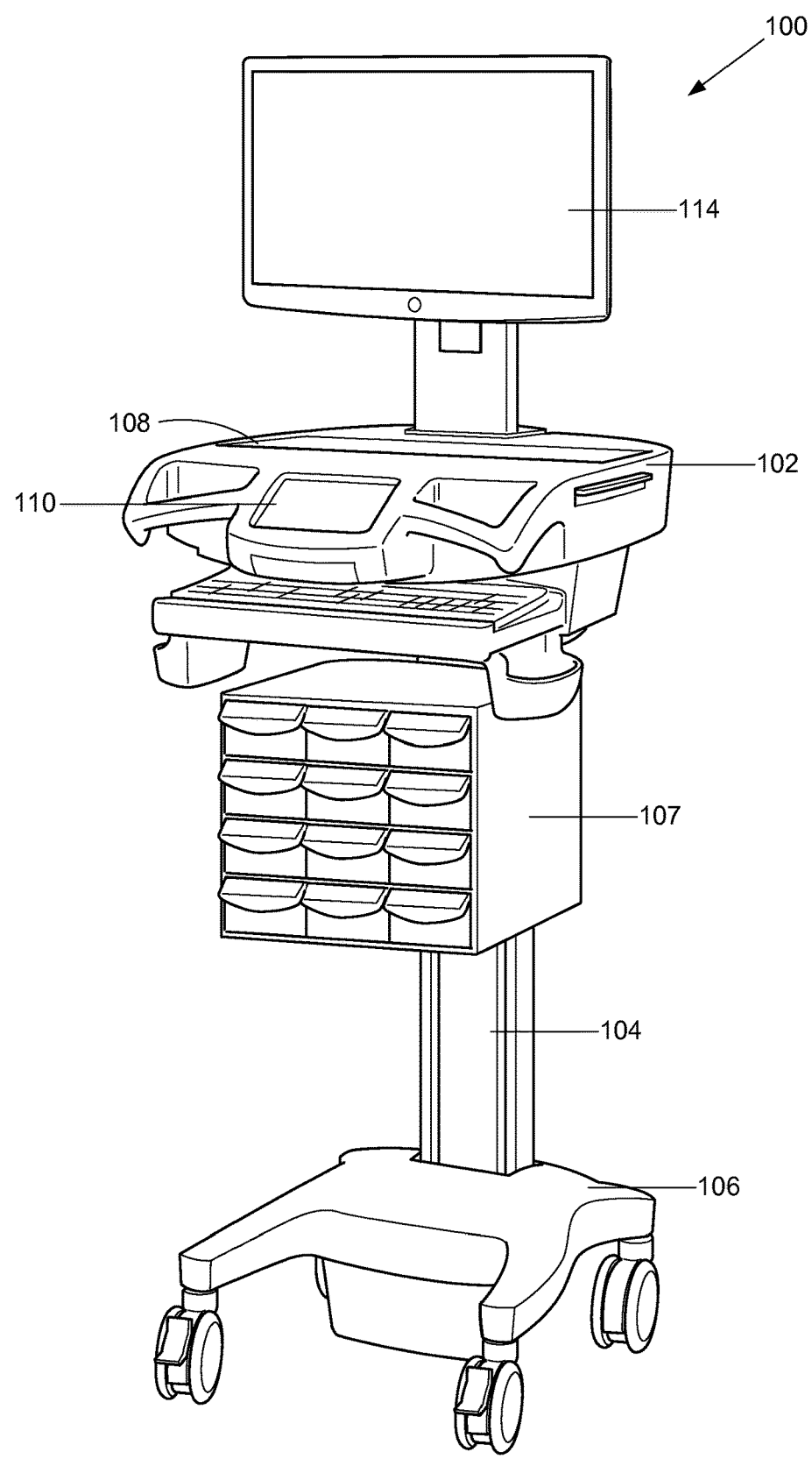
FIG. 1 is an exemplary perspective view of a medical cart in accordance with an embodiment.

FIG. 1 is an exemplary perspective view of a hospital cart 100 disclosed herein, and is referred to hereafter as a medical cart 100, where the medical cart 100 may be used in a variety of healthcare entities, including, but not limited to a hospital, system of hospitals, a hospital floor, a hospital ward or unit, a doctor's office, in-home care, long term care facility, ambulatory surgery centers, clinics, schools, and penitentiaries. With respect to FIG. 1, the exemplary medical cart 100, includes a work platform 102, a support 104 that supports and adjusts the height of the work platform 102, and a base 106 affixed to the bottom of the support 104. Optionally, the medical cart 100 includes one or more drawers 107, which may include manual or electric locks.

The work platform 102 of FIG. 1 houses an embedded computer, also referred to as a control system or hereinafter as a controller, having a computer-readable memory for storing instructions for cart operations and control cart functions, such as an embedded operating system kernel, for example, and a processor for executing those instructions/operating system. Additional disclosure regarding the controller is provided below.

Figure 2A:
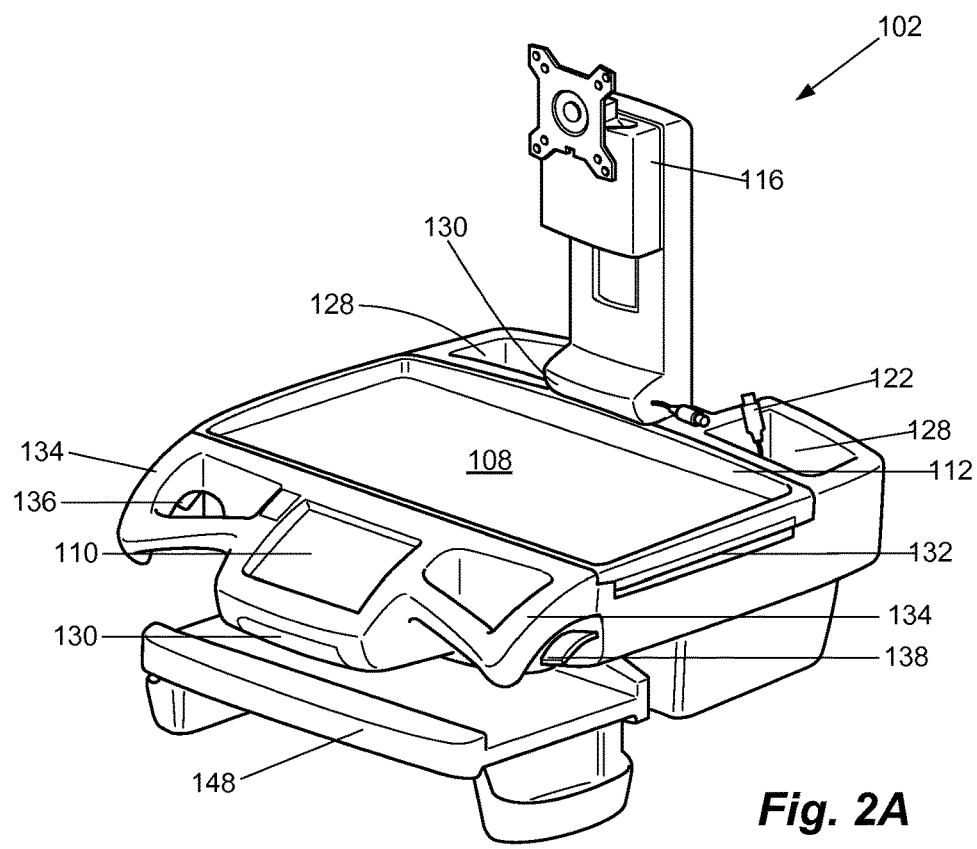
FIGS. 2A and 2B are exemplary perspective views of a work platform of the medical cart of FIG. 1 in accordance with an embodiment.
Figure 2B:
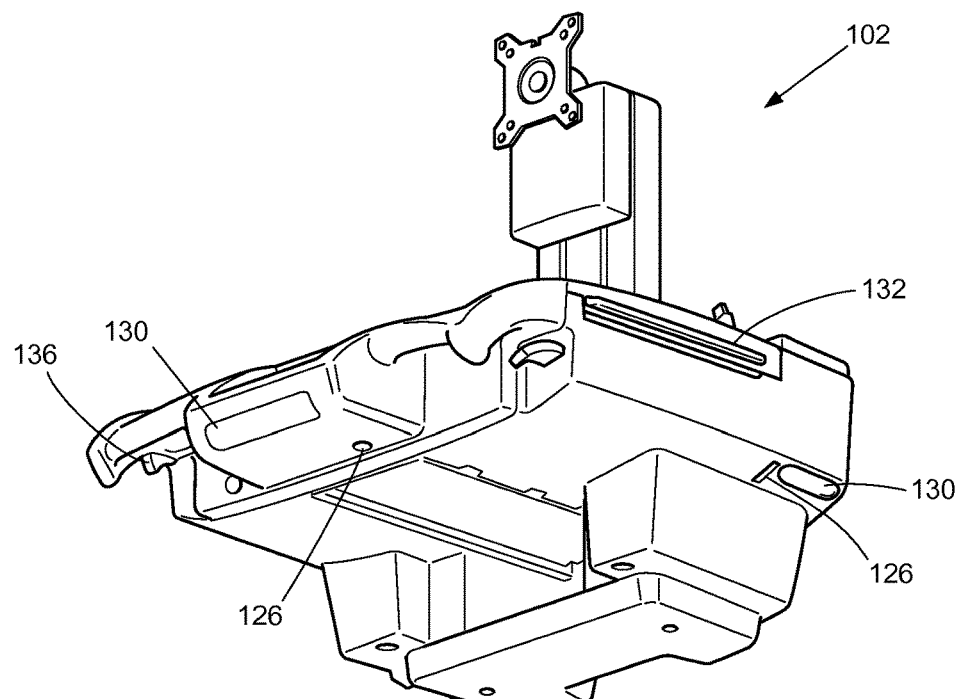

Referring to FIGS. 1, 2A and 2B, the work platform 102 further includes a work surface 108 and a display unit 110. The display unit 110 may be provided as a touch-sensitive display utilizing any of a number of display and touch screen technologies, including, but not limited to, cathode ray tube (CRT), liquid crystal display (LCD), light emitting diode (LED) LCD, organic light-emitting diode (OLED), projection, capacitive touch screens and resistive touch screens. The display unit 110 provides for control of the medical cart 100 via a display screen, which displays various controls as different display areas or display sections that a user can select by touching the display section corresponding to the desired commands in order to provide corresponding inputs to the controller for controlling the cart operations and cart functions. In particular, the display screen displays a dynamic, customizable GUI, examples of which are provided further below, which may be stored in the memory of the controller and executed by the processor as a separate application in the application layer above the embedded operating system kernel. The GUI displays relevant medical cart information to the end-user and enables the end-user to control system functions. System functions include, but are not limited to, power system and battery status, drawer access, electronic lift, a directional-locking caster function, keyboard/work-surface/ground lighting functions, service requests, notifications, and user preferences. The embedded controller and display unit 110 obviates the need for separate LED lights to display battery status on the cart, and enhances the display of battery status to include additional features such as calculations of time remaining and time to recharge, and alerts with explanation messages. The display unit 110 also removes constraints and limitations inherent with physical buttons that must otherwise be installed on the cart.

The work platform 102 may further accommodate a user's computer, such as a laptop, thin client or zero client, that is logically, and preferably physically, separate from the medical cart controller, such that the medical cart controller operates and connects independently from the user's computer, thereby allowing the medical cart to independently operational, including the ability to receive software/firmware updates, messages, notifications and all functions disclosed herein, despite the lack of or non-functionality of the user's computer. The separation of the user's computer from the medical cart controller further reduces or even eliminates the risk of sensitive data on the user's computer from being accessed via the medical cart, and allows for updates to the medical cart controller independent of the user's computer. Even where the user's computer may be communicatively coupled in some manner to the controller whereby the controller may utilize the end-user's computer as a communication bridge to an external network, a the connection between the controller and the end-user's computer does not allow for the exchange or access of data files. In one embodiment, a firewall within the medical cart controller may be provided to prevent any data transfer or other logical connection with files stored on the user's computer. In effect, there is no functional interdependence between the end-user's computer and the controller.

Figure 3:
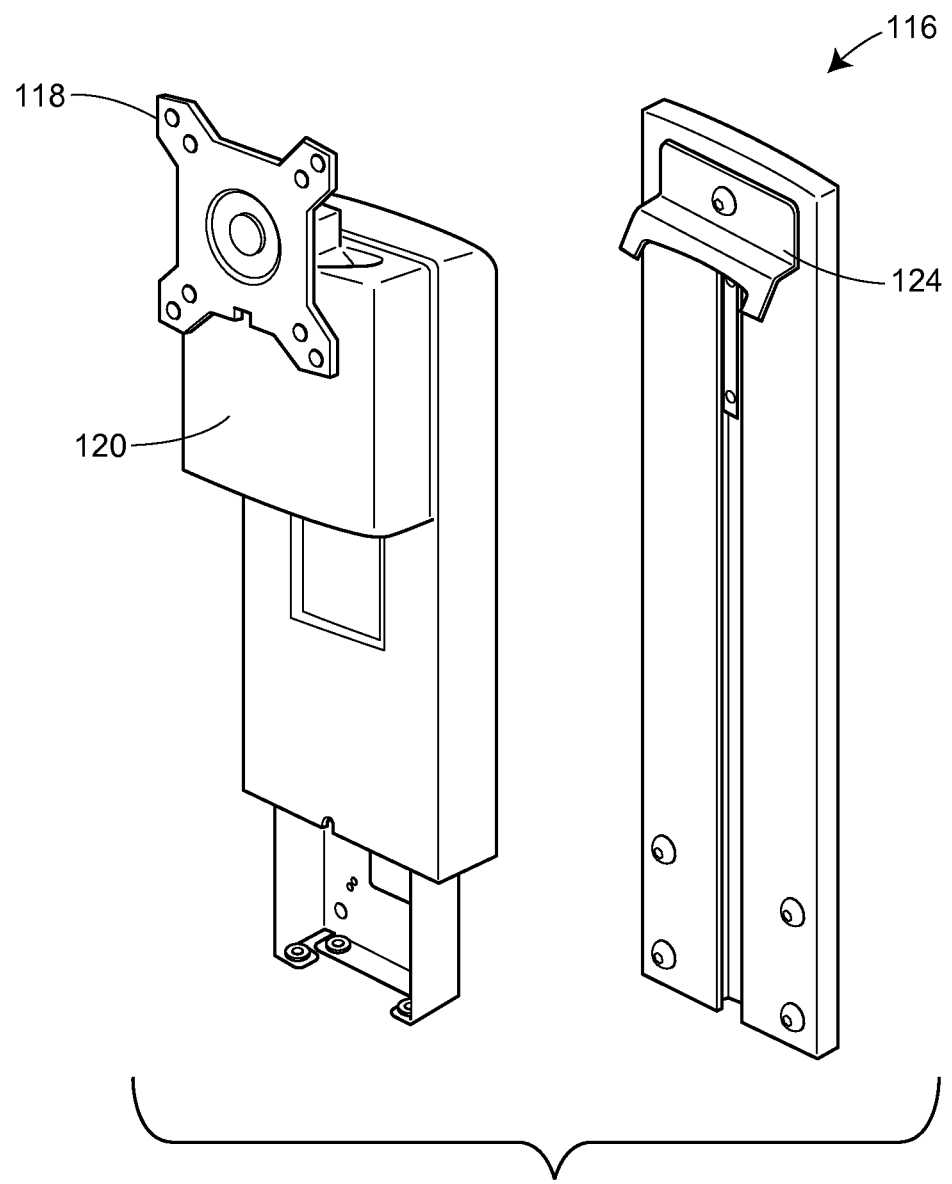
FIG. 3 is an exemplary perspective view of a monitor support of the work platform of FIGS. 2A and 2B in accordance with an embodiment.

In one embodiment, the work platform 102 accommodates the user's computer, which may be placed within an opening under the work surface 108, where the back of the work surface 108 includes a further opening 112 to permit the display of the user's computer to extend out from the back of the work surface 108. In another embodiment, shown in FIG. 1, the medical cart 100 may accommodate a user's display monitor 114 attached to a monitor support 116 affixed to the work platform 102, using a bracket 118 and a mount 120 (FIG. 3), with the user's computer operatively coupled to the display monitor 114 via a cable connection 122 in the opening under the work surface 108 and extending through the monitor support 116 or through the work platform 102 to the user's display monitor 114. The bracket 118 may be rotatable around an axis centered on the bracket 118 thereby allowing the user's display monitor 114 to rotate on the mount 120. The bracket 118 may be slidably engaged with the monitor support 116 using a slide mechanism 124, such as that shown in FIG. 3, so as to affix the user's display monitor 114 at a variety of heights independent of the height adjustment for the work platform 102.

Additional features of the work platform 102 include external connections to the medical cart controller and/or the end-user's computer, such as USB ports 126, a variety of storage bins 128, a variety of work lights 130 operatively coupled to the controller, pull-out shelves 132 to extend the work surface 108 of the work platform 102, and hand grips 134. The work lights 130 may be provided as LED lights, including, but not limited to, a keyboard light positioned above a keyboard platform 148, a work surface light position above the work surface 108 and one or more ground lights to illuminate the path in which the medical cart 100 is being moved. The hand grips 134 are ergonomically designed with multiple grasp points, including handle grips and pistol grips. The hand grips 134 may be used to move the medical cart 100 into position for the user, including adjustment of the height of the work platform 102, particularly if a mechanical (non-motorized) lift is provided. Under the hand grips 134, controls may be provided, including a steer-assist trigger 136 to engage directional-locking casters to assist the user in moving the medical cart 100, and a height lever 138 to engage adjustment of the height of the work platform 102.

As seen in the embodiment shown in FIGS. 1 and 2A, the placement of the display unit 110 is towards the front of the work platform 102 between the hand grips 134. Specifically, the display unit 110 is in front of, and slightly below, the work surface 108 and above the keyboard platform 148. The placement of the display unit 110 allows the user to readily view information presented via the GUI and interact with the GUI in almost any position, including when the work platform 102 is lowered for a sitting position, raised for a standing position. Likewise, the user can readily view the display when moving the cart due to the placement of the hand grips. Further, the placement of the display unit 110 does not interfere with the user viewing information presented on the end-user's computer or on the end-user's display monitor 114, or interfere with the user's use of the work surface 108. In short, the placement of the display unit 110 permits the user full use of the medical cart's functionalities while at the same time permitting full and unencumbered use of the display unit 110 and the functionalities associated therewith.

Figure 4:
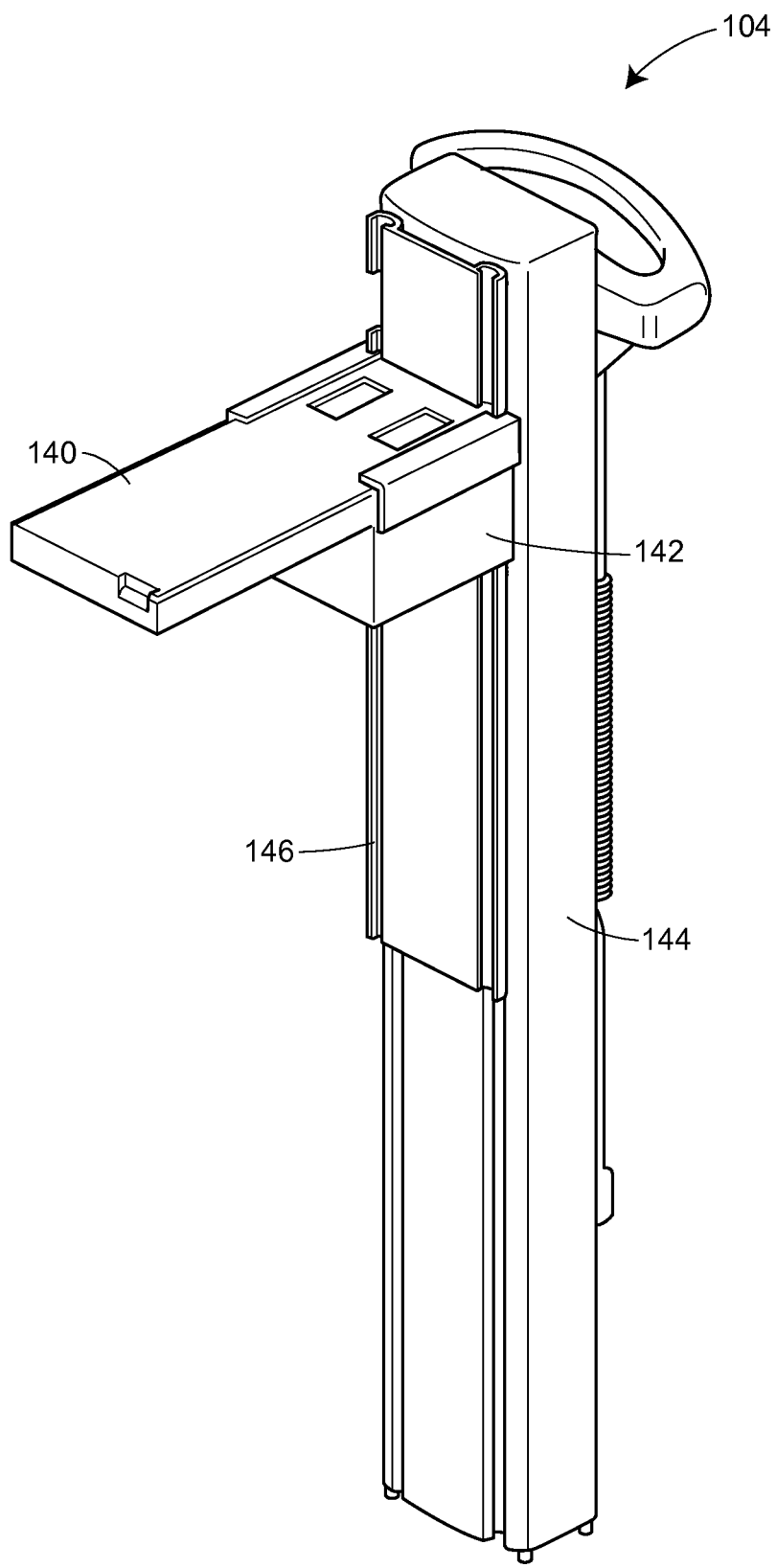
FIG. 4 is an exemplary perspective view of a support for the medical cart of FIG. 1 in accordance with an embodiment.

FIG. 4 depicts an embodiment of the support 104 for the medical cart 100. Generally, the support 104 may be made of a material or materials sufficient to support in excess of the weight of the work platform 102, and a user's computer and/or monitor, such as metals, extruded high-strength plastic, and other materials as known to those of ordinary skill in the art. As shown in FIG. 4, the support 104 includes a mount 140 to which the work platform 102 may be affixed, and a shuttle 142 to engage the mount 140 with a column 144, which runs to the base 106 of the medical cart 100. The shuttle 142 is slidably engaged with a rail 146 of the column 144 so as to affix the work platform 104 at a variety of heights. The work platform mount 140 may further include an integrated keyboard track, to which the keyboard platform 148 may be affixed to accommodate a user's keyboard. The keyboard track allows the keyboard platform 148 to extend outwardly from the shuttle 142 of the work platform 102 and retract back inwardly towards the shuttle 142.

Figure 5:
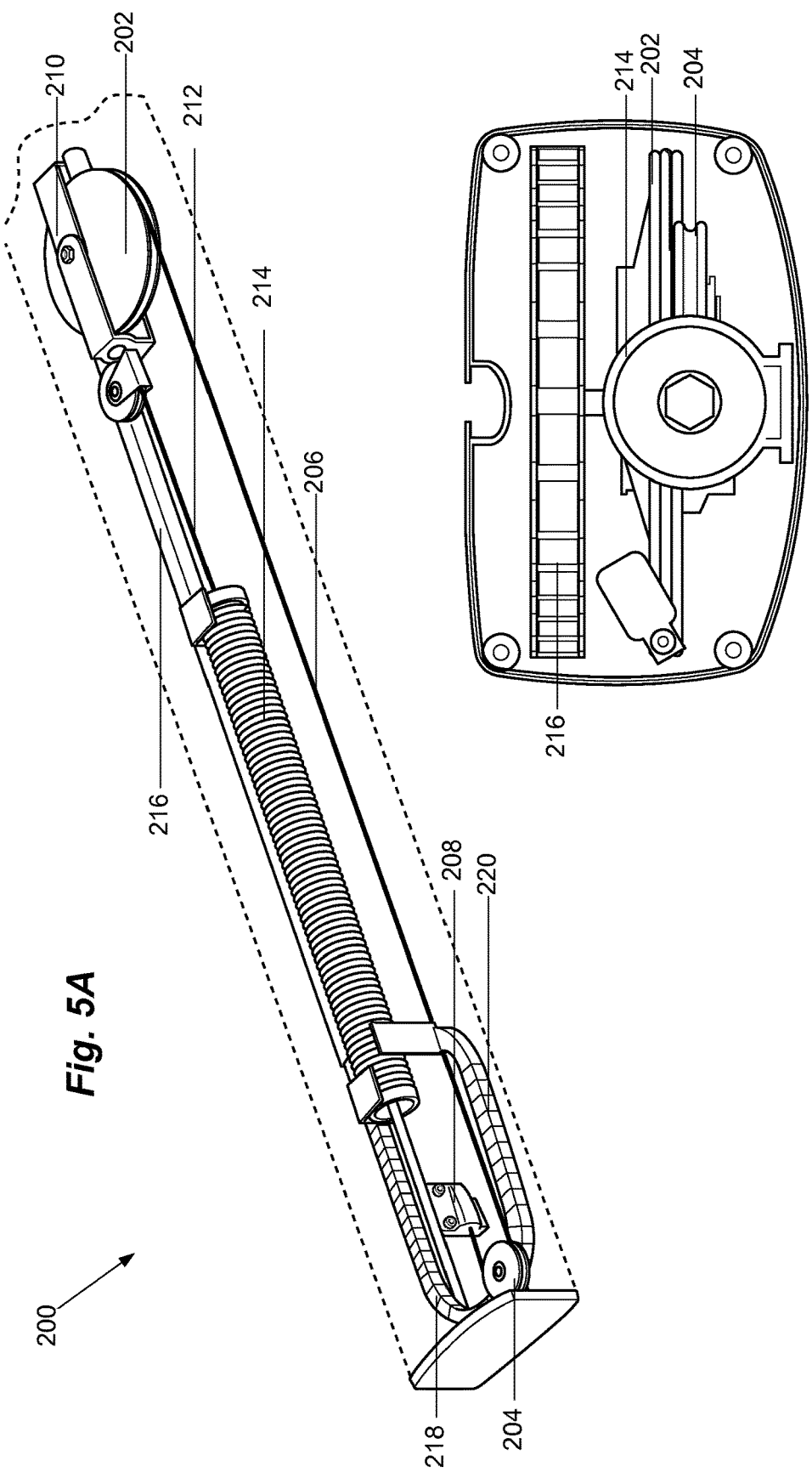
FIGS. 5A and 5B are exemplary cross-sectional views of a lift mechanism of the support cart of FIG. 4 in accordance with an embodiment.

FIGS. 5A and 5B depict an embodiment of a mechanical lift 200 within the support 104 for adjusting the height of the work platform 102. Generally speaking, the mechanical lift 200 is a cam pulley and spring system, having a cam 202 positioned toward the bottom of the support 104 and a pulley 204 attached to the top of the inside of the support 104. One end of a lift cable 206 winds and unwinds around the cam 202 as the work platform 102 is lowered and raised, respectively, with the other end of the lift cable 206 passing through the pulley 204 and affixed to an extension 208 of the shuttle 142 that runs along a slot in the support 104. A second pulley 209 is affixed to a frame 210 supporting the cam 202. One end of a spring cable 212 winds around the second pulley 209 and a second end of the spring cable 212 is affixed to a spring 214, which acts as a counterbalance to the weight of the work platform 102 in order to assist a user in raising or lowering the work platform 104 without having to bear its full weight. Although not shown in FIGS. 5A and 5B, the support 104 may include a series of notches or holes along a portion of the length of the support 104. A latch or other catch mechanism may be provided in the shuttle 142 to engage the notch or hole at the desired height, and manually released when the user adjusts the height of the work platform 104 by, for example, engaging the height lever 138. Alternatively, the latch may be spring-loaded to engage each notch or hole as the height of the work platform 104 is adjusted, and released by pressing the height lever 138 to move to a different height. Those of ordinary skill in the art will understand that additional or alternative mechanisms may be used to lock the work platform 104 in place at a desired height.

Also provided in the support 104 is a cable guide 216 for running electrical cables, such as signal/communication cables and power cables between the work platform 102 and a power source provided in the base 106 of the medical cart 100. Generally, the cable guide 216 is a hollow structure through which the cables run, and may be formed of extruded plastic and/or metal. Towards the top of the support 104, the cable guide 216 is provided as a series of chain links having a passage therethrough for the cable to run. In the alternative, the cable guide 216, including the flexible guide portion 218, may be provided as a three-sided structure, rather than a hollow structure, that protects the cables from interfering with the lift and vice versa. This flexible guide portion 218 of the cable guide 216 is provided so that as the height of the work platform 102 is raised and lowered, the cables running through the support 104 to the work platform may be guided along without interfering with the mechanical lift 200. The flexible guide portion 218 terminates in an end connector 220 which directs the cables through the column slot to the work platform 102.

Figure 6:
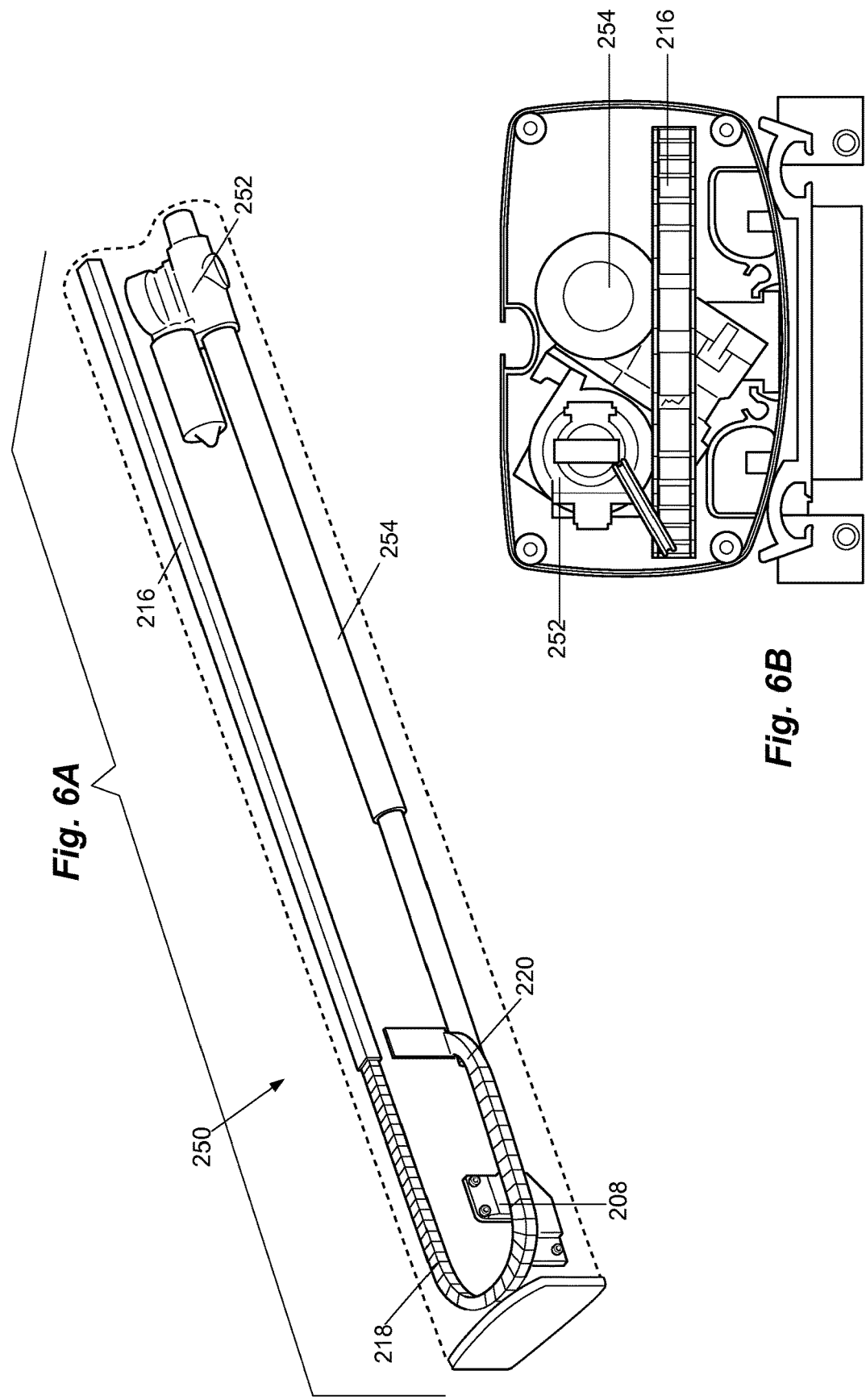
FIGS. 6A and 6B are exemplary cross-sectional views of a lift mechanism of the support cart of FIG. 4 in accordance with another embodiment.

FIGS. 6A and 6B depict an embodiment of a motorized lift 250, as an alternative the mechanical lift 200, within the support 104 for adjusting the height of the work platform 102. Generally speaking, the motorized lift 250 is a lead-screw system, having an electric linear actuator 252 positioned toward the bottom of the support 104, communicatively coupled to the controller in the work platform 104 and powered by the power source provided in the base 106 of the medical cart 100. Generally speaking, the actuator 252 includes a motor, a gear and a spindle that drives a lead screw 254 up or down to raise and lower the work platform 104, where the other end of the lead screw towards the top of the support 104 is affixed to the extension 208 of the shuttle 142 that runs along the slot in the support 104. A cable guide 216 similar to that for the mechanical lift 200 is likewise provided to run electrical cables, such as signal/communication cables and power cables between the work platform 102 and the power source provided in the base 106 of the medical cart 100. In another embodiment, the motorized lift 250 may be provided as a pneumatic piston-driven system.

Figure 7:
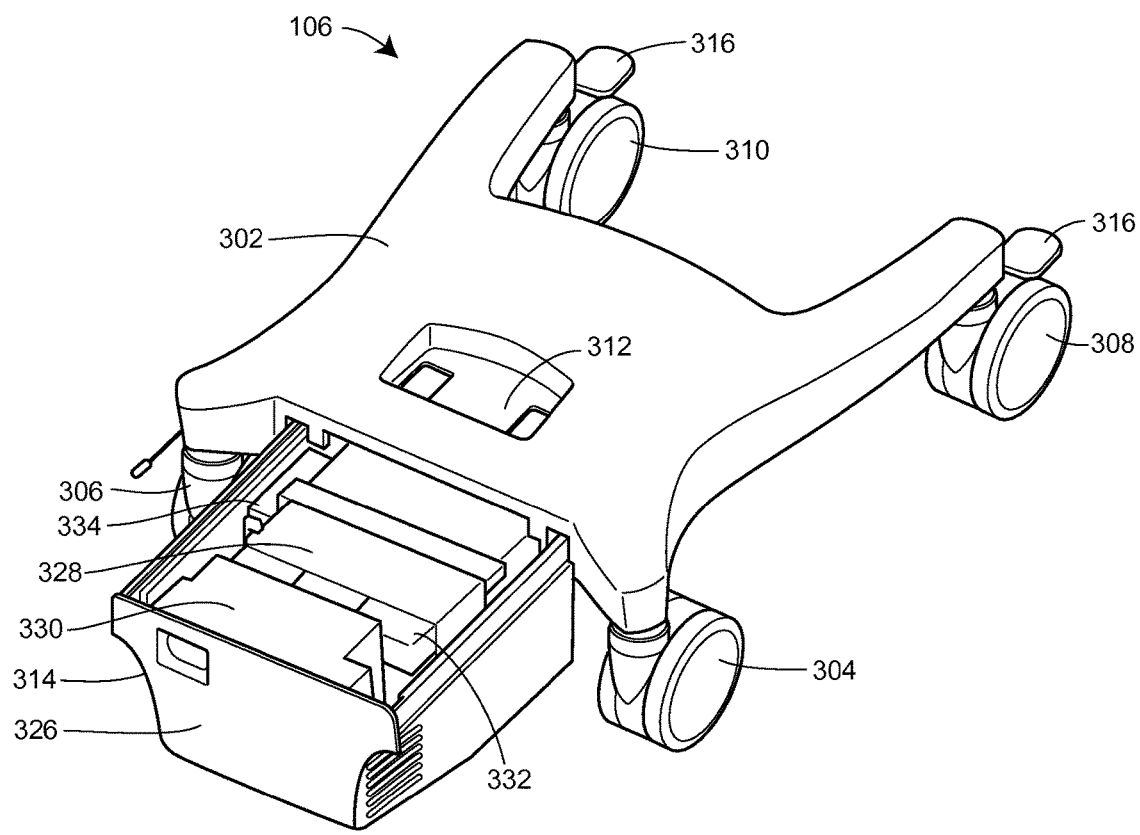
FIG. 7 is an exemplary perspective view of a base of the medical cart of FIG. 1 in accordance with an embodiment.

FIG. 7 depicts an embodiment of the base 106, which includes a main body 302 and multiple casters 304-310 affixed to the bottom of the main body. The main body 302 further allows for the support 104 to be affixed to the base 106, an example of which is shown in FIG. 7 as a depression 312 having the same shape and dimensions as the cross-section of the support 104, such that the lower end of the support 104 may be placed in the depression 312 and securely fastened to the base 106 using screws, bolts and nuts, or any other fastening system, as generally understood by those of ordinary skill in the art. The base 106 further includes the aforementioned power source. As shown in FIG. 7, the power source 314 may be provided underneath the main body 302.

Each of the casters 304-310 may be swivel casters that can rotate in any direction on the main body 302, thereby allowing for movement of the medical cart 100 in any direction. Generally, one or more of the casters, such as the casters 308, 310 facing the back of the medical cart 100, may have a locking mechanism 316 to prevent the wheel of the caster from rotating, thereby preventing or resisting movement of the medical cart 100. A user may engage the locking mechanism 316 by pressing down on a tab to cause the locking mechanism 316 to engage the wheel, for example by friction, a protrusion engaging a notch, or other caster locking mechanisms as known by those of ordinary skill in the art. Lifting up the tab releases the locking mechanism.

Figure 8A:
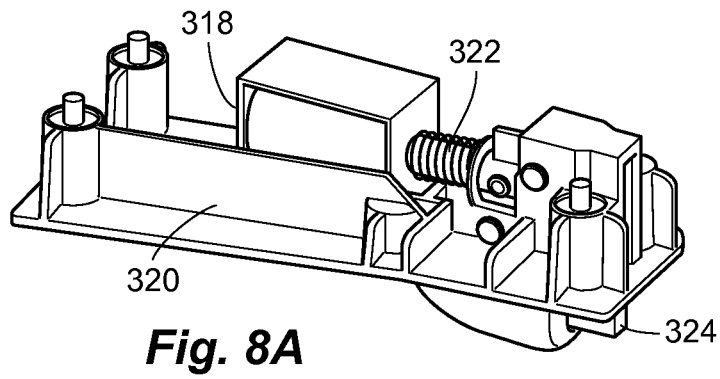
FIGS. 8A, 8B and 8C are exemplary perspective views of a directional-locking caster of the base of FIG. 7 in accordance with an embodiment.
Figure 8B:
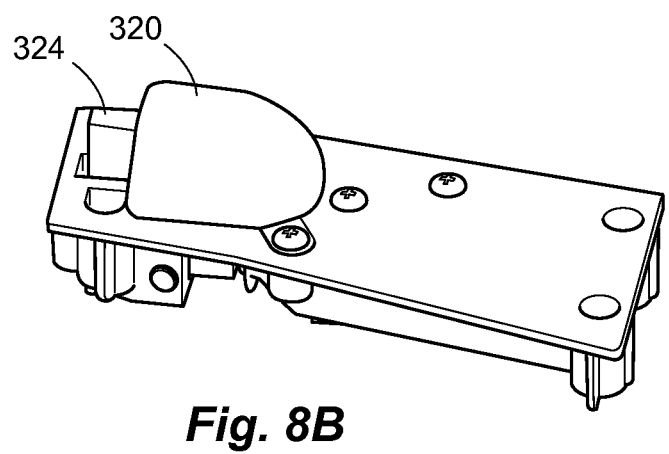
Figure 8C:
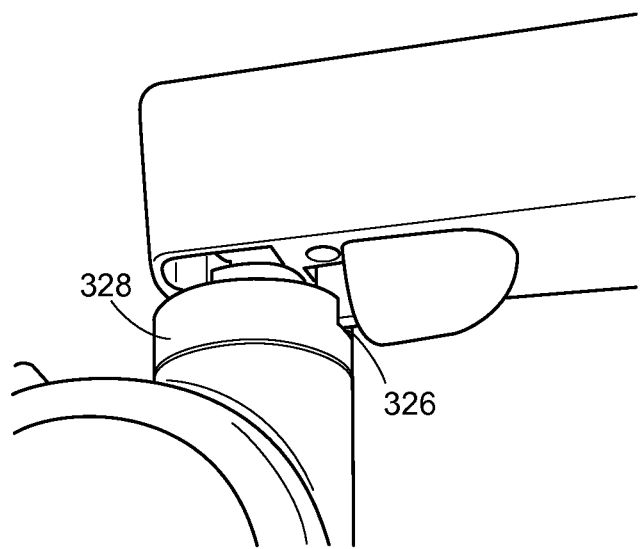

Optionally, one or more of the casters 304-310 may be provided as a directional-locking caster that locks the caster in place to limit the directional movement of the medical cart 100, for example, forwards and backwards or side-to-side. FIGS. 8A, 8B and 8C provide an example of a directional-locking caster operatively coupled to the controller in the work platform 102 and powered by the power source 314 in the base 106. Referring to FIGS. 8A and 8B, the directional-locking caster includes a solenoid 318 within a housing 320, where the housing 320 may be part of the caster or part of the main body 302 of the base 106. Alternatively, a servo-motor may be used instead of the solenoid 318. The solenoid 318, when activated by the controller to engage the lock of the directional-locking caster, causes a plunger 322 to extend. A latch 324 is affixed to the end of the plunger 322, and is likewise extended when the solenoid is activated to as to protrude outside the housing 320. When deactivated, or otherwise controlled to release the directional-locking caster, the solenoid retracts the plunger 322, thereby retracting the latch 324 back into the housing 320.

Referring to FIG. 8C, the caster is provided with a notch 326 formed in a cap 328 of the caster. When the notch 326 is aligned with the latch 324, and the solenoid 318 is activated or otherwise controlled to extend the plunger 322 to lock the caster, the latch 324 engages the notch 326, thereby preventing the caster from rotating in various directions. The resulting alignment of the caster is such that its movement is aligned only with a forward and backward movement of the medical cart 100. When the solenoid 318 is deactivated or otherwise controlled to retract the plunger 322, the caster is free to rotate such that the medical cart may be moved in any direction.

Referring again to FIG. 7, the power source 314 of the base 106 is provided as a single-platform power source within a compartment 326 beneath the main body 302. The compartment 326 may be mounted to the main body 302 on rails affixed to the bottom of the main body 302, such that the compartment 326 may slide out like a drawer to allow for easy access to the power source 314 and its components for service, retrofit, or exchange.

Generally speaking, the power system of the medical cart 100 includes modular output power modules within the work platform 102 coupled to the power source 314 via a power bus (e.g., power cables) in the support 104, where the output power modules include, but are not limited to, one or more alternating current (AC) power modules, such as a 120V AC 150 W output module, and/or one or more direct current (DC) power modules, such as a 19.2V DC 150 W output module. Depending on the equipment the end-user may intend to integrate into the cart, various combinations of any one or two of these power modules may be provided, such as for example, one alternating current (AC) module, two AC modules, one direct current (DC) module, two DC modules, or one AC module and one DC module. The power source 314 may further include a 100-250V AC 47-63 Hz universal-input, and a 24 VDC 450 W output power supply located in the base 106.

More particularly, the power source 314 includes a rechargeable battery 328, and a battery charger/power supply 330 for charging the battery 328 and which serves as a common power source for the entire medical cart 100. The battery 328 may be provided as a lithium battery, sealed lead acid (SLA) battery, nickel cadmium (NiCd) battery, nickel metal hydride (NiMH) battery, or any other type of battery capable of powering the medical cart 100 components as understood by those of ordinary skill in the art. In one embodiment, the medical cart 100 may be provide with batteries of multiple types.

Different battery types (e.g., lithium, SLA, NiCd, NiMH, etc.) may require different methods of charging. Furthermore, the ability of the battery 328 to hold a charge and/or be recharged changes over time as the medical cart 100 is utilized and the battery undergoes various cycles of charging and discharging, often experiencing differing charging practices as a result of different charging practices from user to user. As such, the battery 328 includes a monitoring unit 332, which may be provided as an EEPROM or other memory, for storing the charge profile and parameters for the specific battery type used in the power source 314. For example, the monitoring unit 332 may store various data such as the battery box serial number, model number, build date, etc., as well as the particular charge parameters associated with a given battery 328 and the battery cycle count. Further, the monitoring unit 332 may include safety devices, such as fault detection devices for detecting over temperature and over current. The monitoring unit 332 may be coupled to the battery charger/power supply 330 as part of monitoring the charging operation of the battery 328, and may be further communicatively coupled to the controller in the work platform 102 to provide information about the battery 328, such as the current battery charge, battery capacity last known fuel gauge value, battery fault data (e.g., over temp and over current), cycle count, and battery charge/discharge parameters, and to provide power to the medical cart systems. The monitoring unit 332 allows the charger 330 automatically recognize the battery 328, including its type, charge parameters, etc., and adjust accordingly to charge or discharge the battery 332 without further intervention from a user, such as a technician.

The monitoring unit 332 may be coupled to the battery charger 330 via a communications bus as part of the charging operation of the battery 328, and to provide the information about the battery 328. Generally speaking, although the battery pack itself may include a microcontroller (as provided by the battery manufacturer) the monitoring unit 332 does not have any intelligence, such as a microcontroller, and acts as an extension of the battery charger 330, whereby the battery charger 330 monitors the memory and fault detection devices of the monitoring unit 332, but does not interface with the microcontroller in the battery pack. As such, the monitoring unit 332 may be provided as a printed circuit board, integrated circuits, application specific integrated circuits (ASICs), controllers, programmable logic devices, etc. as understood by those of ordinary skill in the art. However, in one embodiment, the monitoring unit 332 is provided with a microcontroller, such that the battery 228 becomes a smart device that may receive software or firmware updates. In another embodiment, the battery charger 330 may interface with the microcontroller of the battery pack.

The battery charger/power supply 330 may be provided with a universal input, such as an International Electrotechnical Commission (IEC) plug, that can receive a current from a standard 120V or 240V outlet. The plug may be exposed through an opening in the compartment 326 to permit connection to a power cable to supply the battery charger/power supply 330 with electricity. The battery charger/power supply 330 may further include a 24V DC 450 W output power converter to provide power to outlets, including a nominal 24V output (20-30V DC) to the battery 328, and additional 24V outlets to additional systems in the medical cart, such as the controller in the work platform 102. Additionally, the battery charger/power supply 330 may include communication ports, such that it may be communicatively coupled with the controller in the work platform 102, thereby providing information to the controller, such as, for example, information about whether the battery charger/power supply 330 is charging the battery 328, whether the charging operation is complete, battery charge level, etc.

If the medical cart 100 is provided with a directional-locking caster and/or a motorized lift 250, a control unit 334 for operating the directional-locking caster and/or motorized lift 250 may be provided in the compartment 326. The control unit 334 receives commands from the controller in the work platform 104 to control the solenoid 318 (or servomotor) for the directional-locking caster and/or to control the actuator 252 for the motorized lift 250. For example, when commanded to lock the directional-locking caster(s), such when a user engages the steer-assist trigger 136, the controller may instruct the control unit 334 to provide power (or cut power, depending on the design of the solenoid) to the solenoid 318 thereby causing the plunger 322 to extend such that the latch 324 engages the notch 326. When commanded to unlock the directional-locking caster(s), the control unit 334 may cut power (or provide power) to the solenoid 318, thereby retracting the plunger 322 and disengaging the latch 324 from the notch 326. With the motorized lift 250, the controller may instruct the control unit 334 to provide power to the actuator 252 to raise the work platform 102, and to lower the work platform 102 by, for example, reversing/switching the phase of the actuator 252, when a user engages the height lever 138. The controller may further instruct the control unit 334 to control the speed of the lift by adjusting power to the actuator 252 or instruction the control unit 334 to cut power to the actuator 252, or otherwise stop movement of the work platform 102 if an overcurrent fault detection is detected by the monitoring unit 332 and/or battery charger 330, which may occur if the lift is encountering too much resistance (e.g., too much weight). Thus, the overcurrent fault detection provides a safety function to help prevent injury due to the lift. The control unit 334 may be provided as a printed circuit board, integrated circuits, application specific integrated circuits (ASICs), controllers, programmable logic devices, etc. as understood by those of ordinary skill in the art.

As mentioned above, a control system or controller is embedded within the work platform 102 and provided, as its most basic level, as a memory and a processor. More particularly, the controller is provided as an embedded computer independent of, and preferably physically and communicatively separated from, the end-user's computer, that allows an authorized end user access to medical cart data and operations, such as battery usage, memory usage, etc., while segregating and securing patient and/or hospital medical records. In one embodiment, the controller may be connected to the end user's computer whereby the end-user's computer is used as a communication bridge to an outside network, but is otherwise logically and functionally separated from the end user's computer by, for example, the type of connection between the controller and end-user's computer, a firewall or other security technique to prevent access to the end user's computer via the controller and vice versa. In another embodiment, the controller, and hence the medical cart, is physically and/or communicatively disconnected from the end user's computer. In either case, the controller acts as an autonomous computer system separate from the end user's computer.

Figure 9:
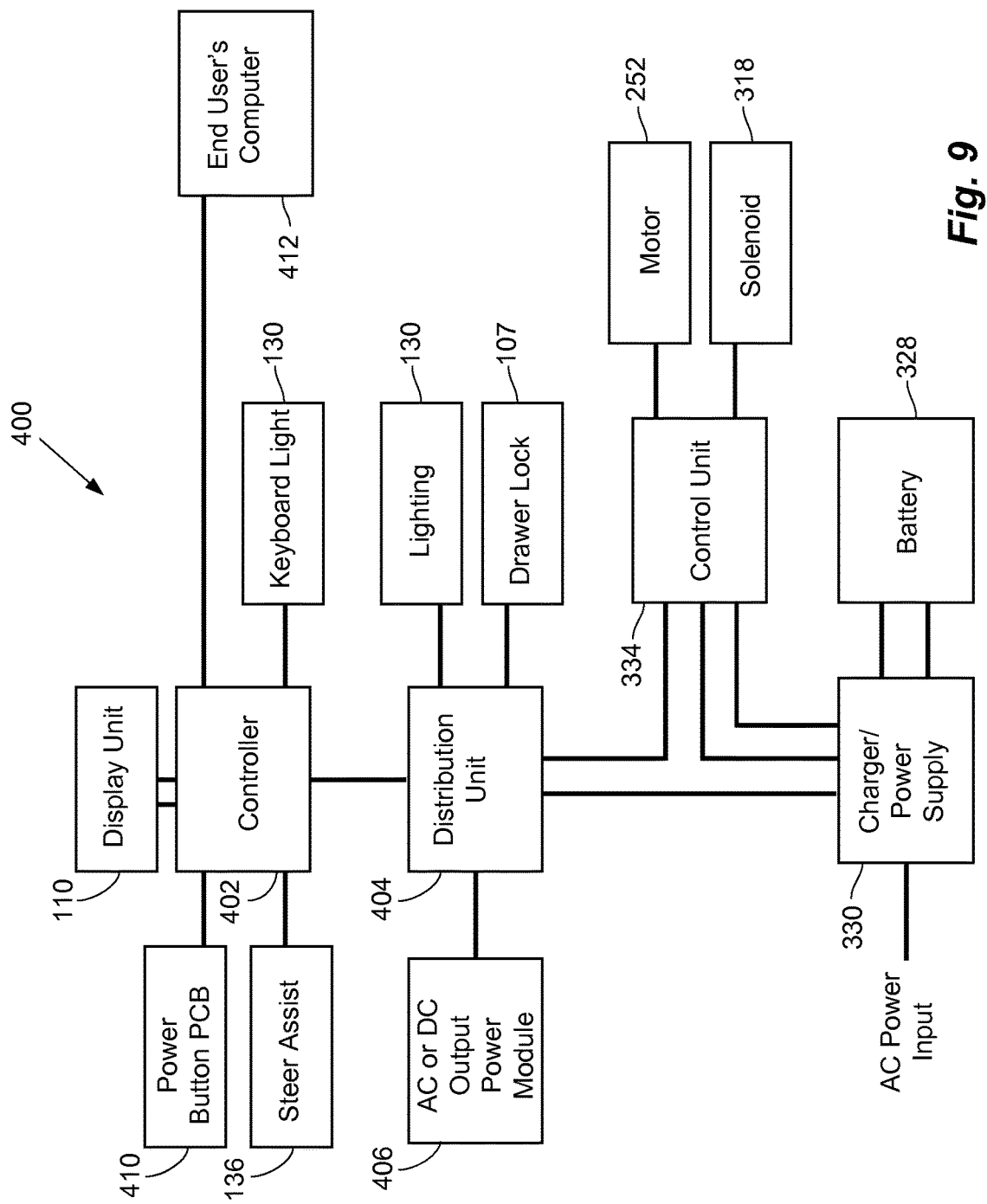
FIG. 9 is an exemplary schematic diagram of the various components parts of the medical cart of FIG. 1 in accordance with an embodiment.

FIG. 9 is an exemplary schematic diagram of the various components parts 400 of the medical cart 100, including the controller 402 operatively and communicatively coupled to a distribution unit 404, which, in turn, is connected to an AC and/or DC output power module 406, the battery charger/power supply 330, which, in turn, is connected to the battery 328. These form the core components of the medical cart's electrical power and communication system. Additional components, some of which have been described above, may include the work lights 130, the locking drawers 107, steer-assist trigger 136, the control unit 334 and associated solenoid 318 for directional-locking casters and/or actuator 252 for a motorized lift 250, a power button 410 to power up the medical cart 100, and the end user's computer 412, each of which are operatively and communicatively coupled to the controller 402 either directly or via the distribution unit 404. The distribution unit 404 may be provided as a printed circuit board, integrated circuits, application specific integrated circuits (ASICs), controllers, programmable logic devices, etc. as understood by those of ordinary skill in the art.

The controller 402 embedded within the hospital cart may be provided as one or more memories, such as a hard disk, solid state hard drive, programmable ROM, RAM or other memory device, and further provided as one or more processors, such as central processing units (CPUs) or other computing devices that support an embedded operating system kernel, such as, for example, the Microsoft Windows™ Embedded CE 6.0 R3, Win7, Linux, Android, or Ubuntu operating system kernels. The controller 402 further supports multi-threaded cart software application, a separate cart diagnostics software application, and a host of hardware interfaces.

To establish communication with the fleet management system described further below, the controller 402 may further include a communications unit to maintain a connection to the end-user's communication infrastructure, such as a server within the healthcare facility, either continuously or at regular intervals. This communication infrastructure may be provided as a wireless infrastructure, such that at least one segment of the communication between the controller 402 and the fleet management system is a wireless communication using wireless communication technologies, including, but not limited to, the Institute of Electrical and Electronics Engineers wireless local area network IEEE 802.11 standard, Worldwide Interoperability for Microwave Access (WiMAX), Ultra-wideband (UWB) radio technology, low bandwidth access such as small, low-power digital radios based on the IEEE 802.15.4 standard, Bluetooth, mesh networks, and cellular technology. In one embodiment, communication between the medical cart 100 and the fleet management system may be facilitated directly via a wireless communication module, such as a cellular communication device. Alternatively, the controller 100 may utilize a hard-wire connection to end-user's computer 412, which may be utilized to tunnel through existing wireless connections.

The embedded controller 402 is one part of a solution to allow the medical cart 100 to be independent from end-user computers, while allowing for flexible configuration, operation and maintenance. The medical cart system and method disclosed herein does not require installation or maintenance of software or drivers on end-user computers 412 and servers since there is an embedded controller 402 on the medical cart 100 that communicates with a web-based centrally-hosted platform, described further below. The embedded controller 402 further allows for flexible support for integrated solutions through local API's (application programming interfaces) to control medical cart operations, and for notifications and service requests. In one embodiment, the use of API's to control medical cart operations, notifications, service requests, etc. may also be provided from the fleet management system, described further below. As such, API's may be interfaced via the fleet management system or via direct communications on the medical cart (e.g. an API to control login, drawer locks and login/lock timeouts controlled by badge readers, proximity scanners, biometrics, or single sign-on systems).

Figure 10:
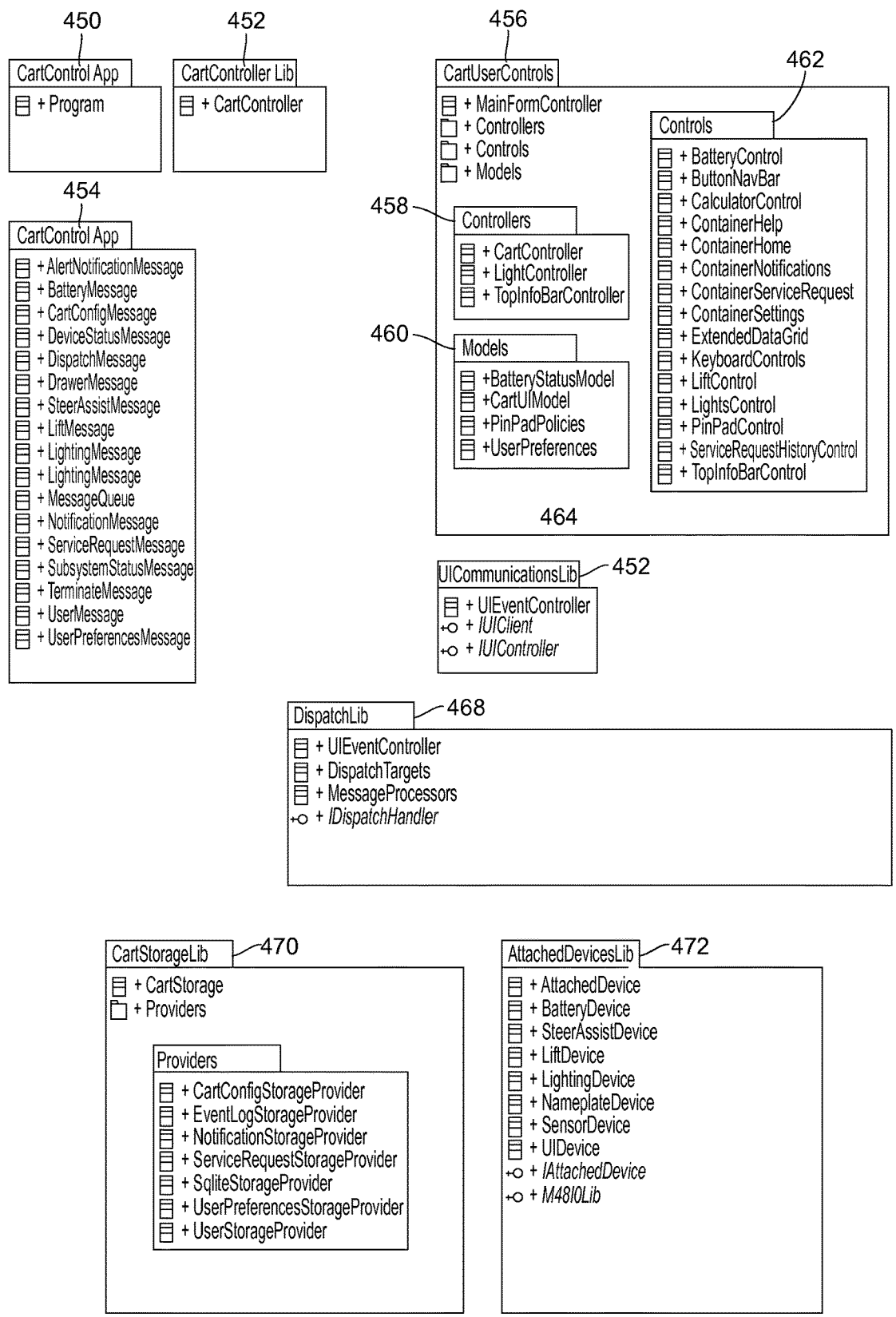
FIG. 10 is an exemplary depiction of applications, libraries and controls provided with a controller of FIG. 9 in accordance with an embodiment.

FIG. 10 is an exemplary depiction of applications, libraries and controls which may be included as part of, and/or called by, the embedded operating kernel of the controller 402, shown in FIG. 10 as the cart control application 450 with an associated cart control library 452 of the various medical cart functions, operations, controls, etc. The applications, libraries and controls may be stored within the memory of the controller 402 and executed by the processor. As seen in FIG. 10, the applications, libraries and controls may be provided for a variety of functions, including, but not limited to, cart control, system reboots, cart shutdown, user controls, messaging, user interface communications, dispatch, cart storage and device attachments. Cart/user control may be provided by improved security through enhanced remote control of login, configurable timeouts, and drawer access via PIN codes.

For example, a messages library 454 may detail the various messages that may be provided to a user on the display unit 110, including, but not limited to, alerts, battery information, and medical cart configuration (such as information on installed subsystems and devices, the GUI configuration, display unit 110 brightness, height, or other configurable features of the medical cart 100). Additional messages may include drawer access (such as locked/unlocked, last access time, last user to access the drawer, etc.), steer-assist (such as whether the directional-locking casters are engaged or not), lift (such as the current height of the work platform 102), lighting (such as which work lights are on, non-functional, etc.), message queue (such as the number and/or list of messages or notifications either awaiting the user or that have been sent by the user and/or medical cart) including messages about location (e.g., wireless access point connections), time/date, weather, calculator, presets or user preferences, pedometer, internet access, etc., notifications (such as notifications from the fleet management system, notifications regarding medicine pick-ups, availability or completion of patient medical results—though not the results themselves, etc.), service requests (such as the status of a request for service, service request history, etc.), sub-system status (such as the operational status of drawers, power supply, directional-locking caster, sensors, work lights, lift, and other subsystems/devices installed on the medical cart), and user preferences (such as presets, display unit 110 brightness, height, volume, timeouts, GUI configuration, etc.), healthcare entity announcements or codes, and availability of software/firmware updates to name some.

A GUI application 456, shown in FIG. 10 as cart user controls and which will be discussed further below, provides a variety of controllers 458 for installed routines or tools, models/simulations 460 and controls 462 which may be displayed on the display unit 110 to the user, and which the user may select via touchscreen. Examples of various controllers 458 for routines or tools provided by the controller 402 via the GUI include, but are not limited to, a calculator, work light controls, and information provided in a top bar of the GUI, such as drawer lock status, connectivity, cart identification, time and data, etc., an example of which is shown with respect to an exemplary GUI below. The controller 402 may also model or simulate 460 various medical cart systems, such as the operational capacity of the medical cart 100 at various battery charges levels, user access policies, user preferences, and user interfaces. Controls 462 provided via the GUI may include controls for the battery, GUI navigation via a bottom bar disclosed below, calculator, help/assistance, a GUI homepage, notifications, service requests, settings, keyboard, lift, lift presets including personal lift presets, pinpad to permit access to the medical cart functions and operations, service history and information via an information bar disclosed below, to name some.

Additional libraries include communications 464 regarding medical cart events, a dispatch library 468 pertaining to service dispatches for the medical cart 100 or medical carts within a particular floor, unit or hospital, cart storage 470 and a library of devices 472 installed on the medical cart 100 and recognized by the controller 100. The cart storage library 470 may be provided as a user file that stores the various user preferences for the medical cart 100 in user profiles, cart configurations, event logs, notifications, service requests, etc. The attached devices library 472 provides a list of, and related information about, all devices installed on the medical cart 100 and recognized by the controller 402, including, but not limited to, the battery, directional-locking casters, lift, work lights, sensors and GUI. The devices library 472 may be updated as subsystems and devices are added to or removed from the medical cart 100.

Figure 11:
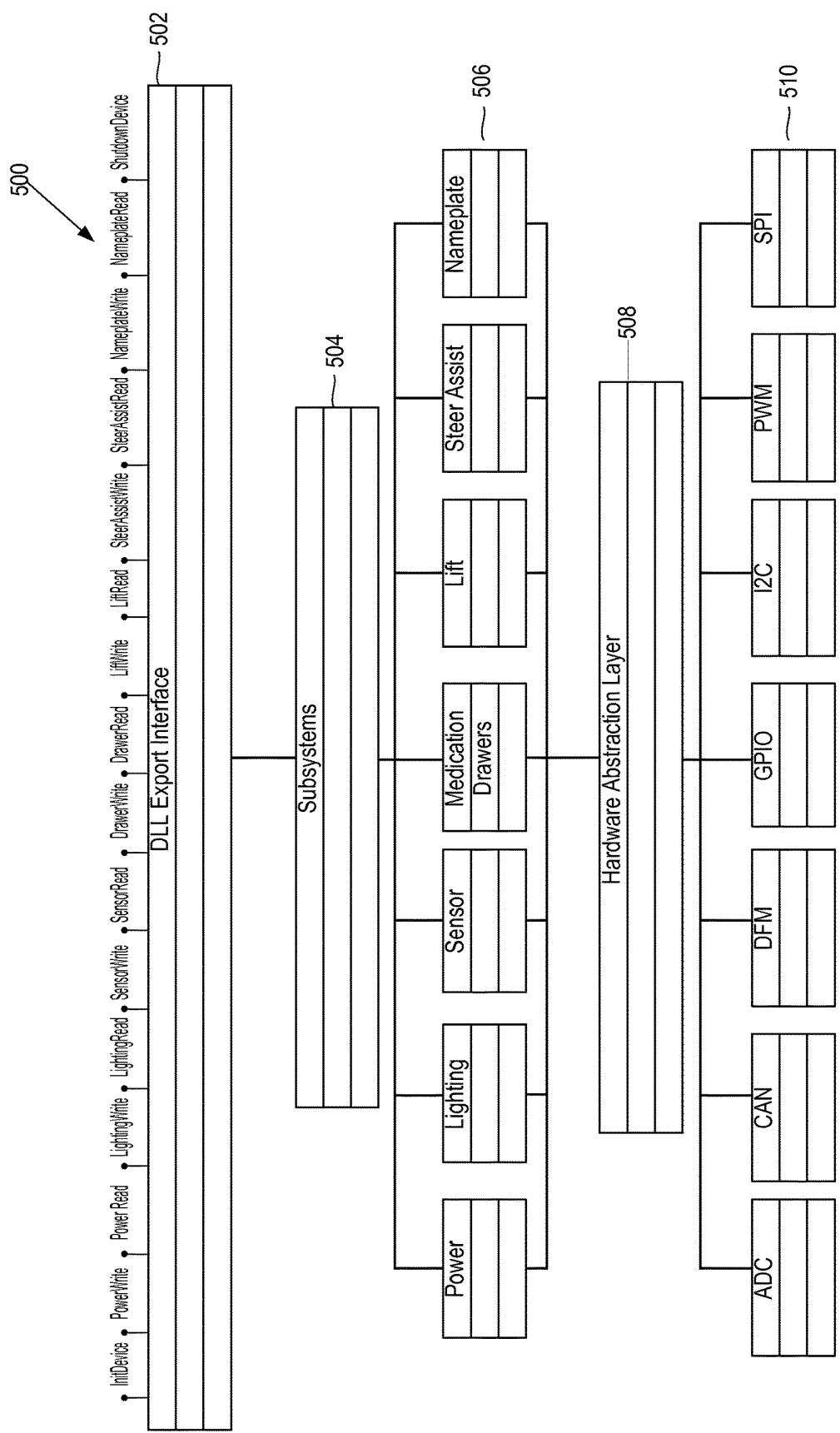
FIG. 11 is an exemplary schematic diagram of a bus architecture and system for the medical cart of FIG. 1.

FIG. 11 is an exemplary schematic diagram of the bus architecture and system for the medical cart 100. The bus architecture of the medical cart 100 is structured such that the power source 314, which may be provided in the base 106, and the controller 402, which may be provided in the work platform 102, act as bookends in the interconnection scheme. Thus, any number of available optional subsystems, including the motorized lift 250, a directional-locking caster 304, and individual locking storage drawers 107, etc., may be inserted in-line between the power source 314 and the controller 402 using this architecture.

As seen in FIG. 11, the bus architecture includes a dynamic link library (DLL) export interface 502 for various read/write operations, communicatively coupled to a cart subsystems bus 504 described further below, where provided subsystems 506 may include, but are not limited to, the power source 314, work lights 130, sensors, access to drawers 107, the motorized lift 250, steer-assistance (directional-locking casters 130) and cart configuration data. The subsystems 506 are interfaced with a hardware abstraction layer 508 to provide direct access for the subsystems 506 to the medical cart hardware. Physical hardware interfaces 510 are thus provided, which may include, but are not limited to, analog/digital conversion (ADC), controller area network (CAN) bus, device fault management (DFM), general purpose input/output (GPIO), inter-integrated circuit (I2C), pulse width modulation (PWM) (e.g., for power control), and serial peripheral interface bus (SPI).

The subsystems 506 are capable of remote firmware and software updates, much like the embedded controller 402 and power source 314. In particular, the open architecture of the bus allows inline insertion of the subsystems 506 into the power and communications bus system by virtue of the power source 314 and controller 402 bookending the bus interconnections. The inserted subsystems 506 may be provided as smart devices that contain embedded microcontrollers and memory. This enables the controller 402 to automatically recognize newly-installed devices or subsystems, establish communications with the recognized devices or subsystems, and adjust the GUI displayed on the display unit 110 (for example, by updating the attached devices library 472 and updating the controls 462, such as by a firmware or software update via the fleet management system) to reflect the medical cart 100 features/functions added from the new device/subsystem. This intelligence also provides the controller 402 as scalable and flexible for future product upgrades, such as execution of firmware updates to any of the attached subsystems 506, including the power source 314. The updates may be executed by an authorized service technician at the medical cart 100 locally, for example via a hospital server or by interfacing with the medical cart directly through the GUI and/or via a data port, such as a Universal Serial Bus (USB) port. As discussed further below, updates may be remotely pushed to the medical cart 100 individually or to a fleet of medical carts 100 via the fleet management system.

The communication protocol and communication channel used within the bus architecture to allow the controller 402 to communicate with various devices and subsystems within the medical cart may be based on a controller area network (CAN) protocol mentioned above, such as the CAN 2.0B standard, which is a bus standard that allows microcontrollers, such as microcontrollers in the smart devices and subsystems, to communicate with each other and with the controller 402. Thus, the communication bus of the medical cart 100 has a CAN bus architecture. Thus, components of the medical cart 100, such as sub-systems, add-ons, peripherals, etc. that are provided as intelligent devices (e.g., with an independent microcontroller), are able to communicate with each other within the medical cart 100 without management by the controller 100. A multi-packet protocol provides the ability to transfer messages longer than the maximum allowable payload length, such as, for example, firmware or software updates that are longer than the payload length. Instead of a CAN bus architecture, the communication bus of the medical cart 100 may have alternative specialized internal communications networks that interconnect components inside the medical cart 100, including ring, star or mesh networks.

Figure 12:
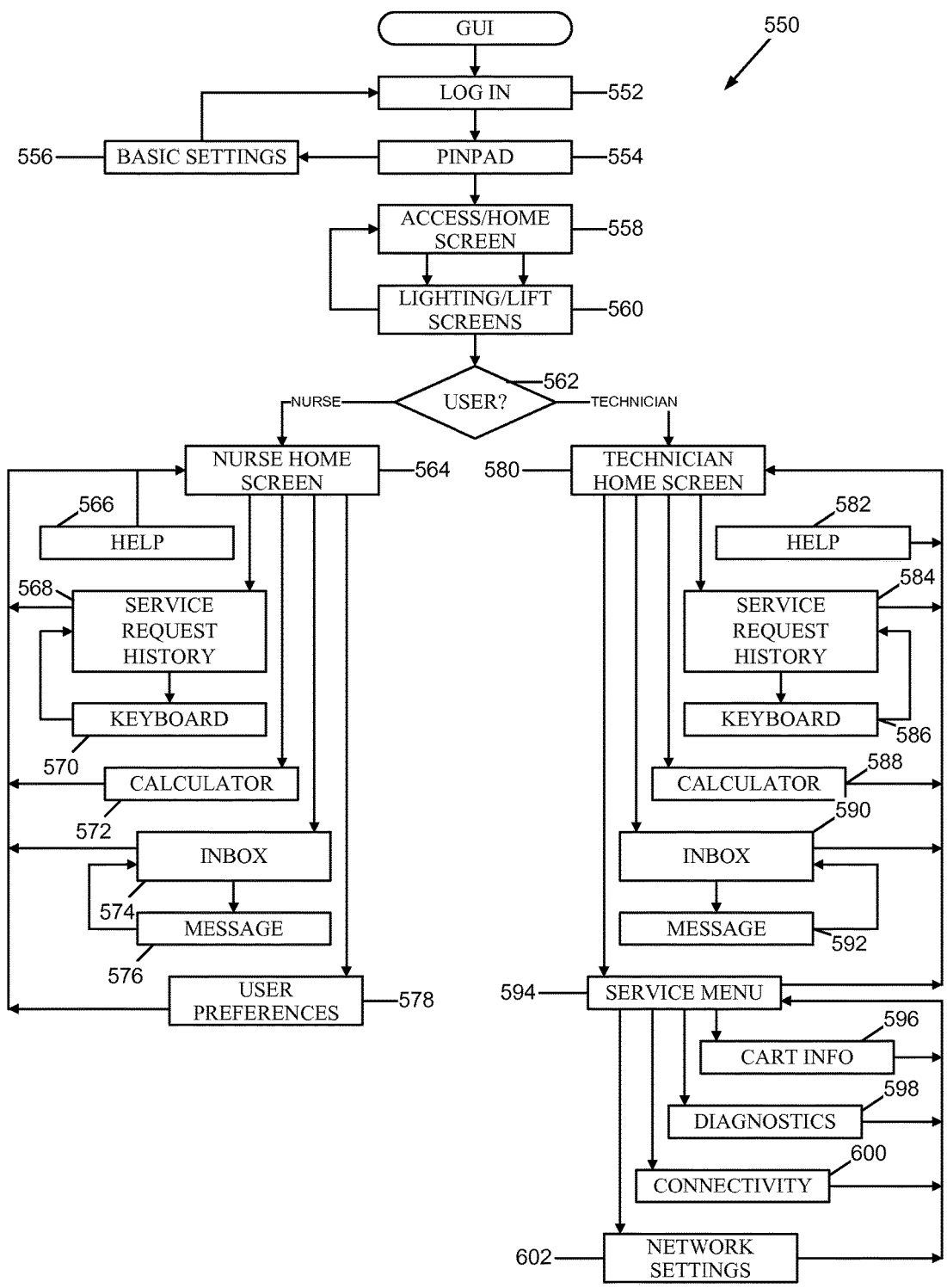
FIG. 12 is an exemplary GUI navigation flowchart associated with the medical cart of FIG. 1 in accordance with an embodiment.

As part of the monitoring, control, and operation of the medical cart 100, a display application, such as a graphical user interface (GUI), may be provided and integrated with the controller 402, for example as part of the operating system kernel, to facilitate a user's interaction with the medical cart 100, as well as the fleet management system described further below. FIG. 12 is an example of a GUI navigation flowchart 550 which provides the graphical user interface (GUI) associated with the medical cart 100 and the graphical displays as may be displayed to a user, where FIGS. 13-31 are exemplary graphical displays that may be provided by the GUI on the display unit 100 to the user to provide information and allow the user to monitor, control and operate various parameters and functions of the medical cart 100.

However, before discussing the GUI in greater detail, it should be recognized that the GUI may include one or more software routines that are implemented using any suitable programming languages and techniques. Further, the software routines making up the GUI may be stored and processed within the controller 402. Preferably, but not necessarily, the GUI may be implemented using a familiar graphical windows-based structure and appearance, in which a plurality of interlinked graphical views or pages include different sections on the display pertaining to various controls, functions, monitoring, etc. which are selectable by the user, for example by a user's touch on the touchscreen, to enable the user to navigate through the pages in a desired manner to view and/or retrieve a particular information, execute particular functions and execute particular controls of the medical cart 100. The features and/or capabilities of the medical cart 100 may be represented, accessed, invoked, etc. through one or more corresponding pages, views or displays of the GUI. Furthermore, the various displays making up the GUI may be interlinked in a logical manner to facilitate a user's quick and intuitive navigation through the displays to retrieve a particular type of information or to access and/or invoke a particular capability of the above data sources.

For example, the GUI provides intuitive graphical depictions or displays of medical cart information. Each of these graphical displays may include numerical, textual and graphical displays of status information regarding the medical cart 100 and its components. For example, a display depicting a battery may provide corresponding status information of battery 328. On the other hand, a display depicting service history may include status information associated with a previous service request. In any event, a user may use the status information shown within any view, page or display to quickly assess whether a problem exists within the medical cart, ascertain the status of various medical cart functions, sub-systems, service requests, etc. and access various medical cart functions and controls.

Additionally, the GUI described herein may automatically, or may in response to a request by a user, provide information to the user regarding medical cart subsystems 506, the power source 314, service requests, user preferences, operating system, etc. However, depending on the type of information or the security clearance of the particular user, restrictions may be imposed on the basis of the type of information, available controls and available functions. For example, a nurse may be restricted to viewing information regarding the charge level of the battery 328, status of service requests, messages and notifications, his or her preferences (e.g., display unit 110 brightness, lift presets, drawer lock timeout, login timeout, volume, etc.) and the functions the nurse is responsible for, such as control of the lift, control of the work lights, drawer access, locking/ unlocking of the directional-locking casters, service requests and calculator. At the same time, the nurse may be prevented from viewing diagnostic information, connectivity information with the fleet management system, network settings, etc. On the other hand, a technician servicing the medical cart may be restricted from viewing user preferences, but permitted to conduct diagnostics, view diagnostic results, view connectivity information, view and change network settings, etc.

Figure 13:
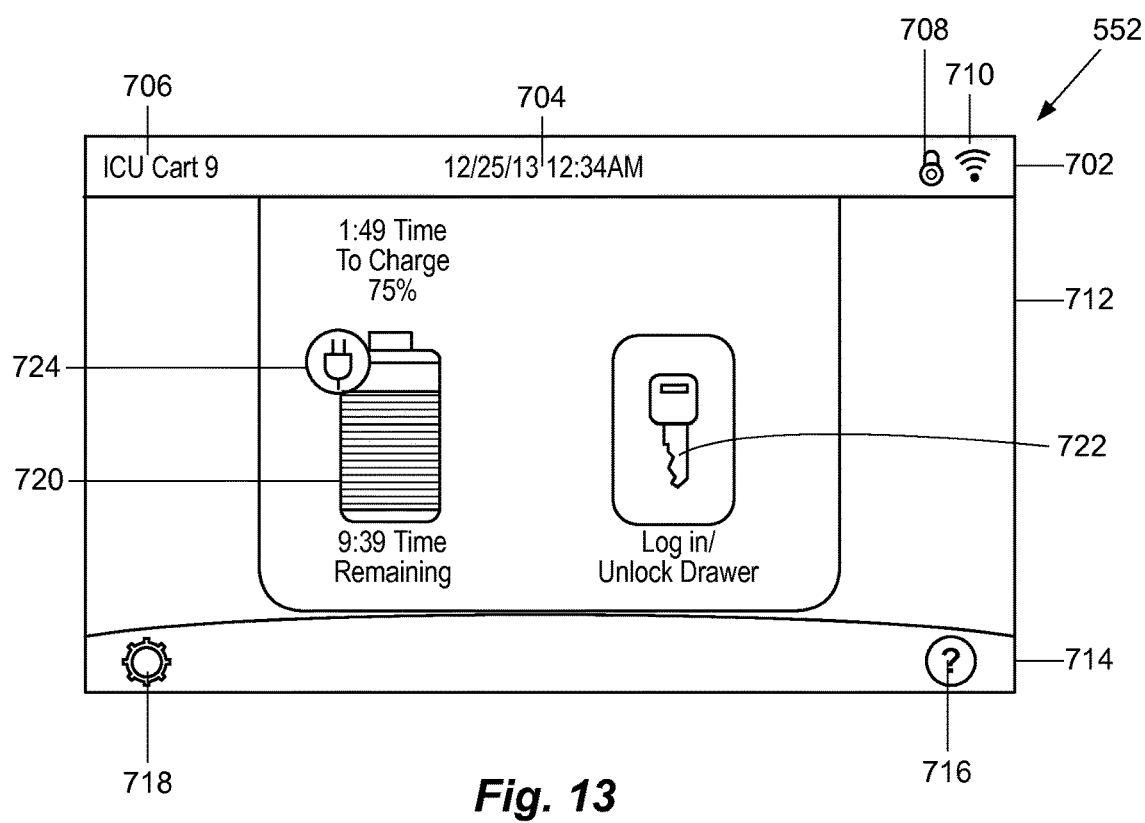
FIGS. 13-31 are exemplary graphical displays that may be provided by the GUI on a display unit of the medical cart of FIG. 1 according to the navigational flowchart of FIG. 12 in accordance with an embodiment.

Each graphical display may be formatted according to a common format, such that it presents different views within each display. For example, in the exemplary displays that follow, each graphical display is formatted to include a header or information bar or view at the top of the graphical display, a control area/view in the middle of the display, and a footer or button bar or view at the bottom of the display. Referring to FIG. 13, an information bar 702 may display basic information in various graphical elements or sections, referred to hereinafter as icons, such as the date and time 704, the name, serial number or other identifying information of the medical cart 706 (e.g., "ICU Cart 9"), drawer lock status 708, and an indicator 710 of a communication connection with the fleet management system for when the medical cart 100 is in communication with the fleet management system. In one embodiment, the indicator 710 may also show the status and strength of the communication connection, particularly for wireless communications. Once a user logs in to the medical cart 100, the information bar 702 may further include the name of the user, the user's primary group or department within the healthcare entity (e.g., ICU, IT, etc.), and selectable icons (e.g., buttons) to log out of the medical cart 100.

The control area 712 is primarily used to display information to the user and allow the user to control different operations and functions of the medical cart 100. Generally speaking, the control area 712 include various icons corresponding to different options or actions available to the user. These icons are selectable by the user, for example by touching the icon corresponding to the desired option or action if the display unit 110 is provided as a touchscreen display, thereby causing the controller 402 to engage in the corresponding function or operation of the medical cart 100, examples of which are described below. The selectable icons, when selected by the user, may also result in navigating through the various graphical displays of the GUI to display information as requested by the user, further controls pertaining to a desired action, information pertaining to a requested action, etc. Whereas the information bar 702 and the bottom bar 714 have relatively static icons from graphical display to graphical display (with some changes occurring, such as when a user logs in and logs out), the control area 712 is more dynamic in that it changes to present different icons depending on the user's selections.

The button bar 714 generally displays selectable icons pertaining to different actions, help request button 716 and a settings button 718 to adjust medical cart 100 settings. Additional icons that may be displayed in the button bar 714 once a user logs in include buttons to view user preferences, to view service history (and request additional service), view notifications and messages, and to bring up a calculator.

Referring to FIG. 12, the GUI displays various views used by either an operator (end-user) of the medical cart, such as a nurse or service technician, though it should be understood that different views (and access to different controls, functions and information) may be customized for different users depending on their department, group, level of access, etc. Each time the medical cart 100 is accessed, the GUI may display a login display 552 (FIG. 13). In the exemplary login display of FIG. 13, the control area 712 may display icons for battery status 720 and for logging in 722 to the medical cart 100. The battery status icon 720 may be displayed regardless of whether a user is logged in or not, so that the status of the battery can be readily ascertained and addressed as appropriate (for example, by plugging in the charger 330 to an outlet if necessary). The battery status 720 may include an icon of a battery that visually indicates and approximates the amount of charge left in the battery, battery life de-rating and temperature, which may coincide with a textual display of the remaining charge relatively to battery capacity (e.g., 75%), and the time remaining until the battery 328 is drained of its charge. The time remaining for the battery may be calculated by the monitoring unit 332 and/or the controller 402 based on a variety of factors, such as energy consumption from the end-user's equipment, current cart settings (e.g., display unit 110 brightness, battery capacity) and charge use, charge used during recent cart usage, predicted charge usage based on past usage history, etc. The battery status icon 720 may further include an icon 724 indicating whether the battery 328 is charging, and the amount of time until the battery is fully charged. The time remaining to charge the battery may likewise be calculated by the monitoring unit 332 and/or the controller 402 based on, for example, the current charge in the battery, the battery capacity and the rate at which it is increasing its charge, which may be relative to the rate at which the battery is losing its charge due to usage of the medical cart by a user, illumination of the display unit 110, display unit 110 brightness and activation of the work lights 130, etc.

Figure 14:
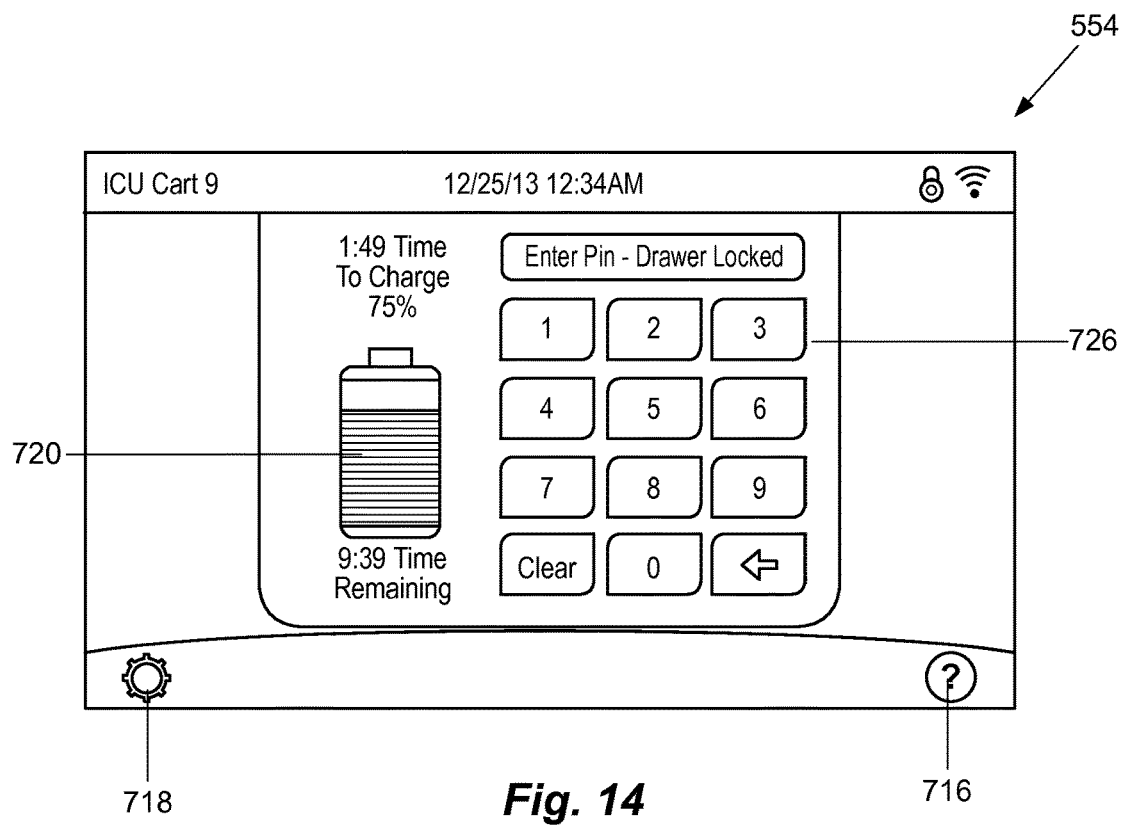

Referring again to FIG. 12, if the user selects the login icon 722, such as by touching it on the display unit 110, the GUI navigates to a passcode or pin pad screen 554 (FIG. 14). More particularly, in the exemplary pin pad display of FIG. 14, the GUI updates control area of the login display of FIG. 13 to change the login icon 722 to a numeric pin pad icon 726. The alphanumeric pin pad icon 726 includes individually selectable elements corresponding to numbers, letters or characters with which to enter a passcode (e.g., PIN) unique to the user to as to authenticate the user and permit access to the medical cart 100 based on that user's level of access. The passcode may be displayed in a text box above the alphanumeric elements as the passcode is entered. Although a pin pad is depicted, those of ordinary skill in the art will readily understand that various mechanisms for logging in to the medical cart may be utilized, including, but not limited to, biometric authentication and badge readers, and dual factor authentications such as multiple pass codes, pass code and physical authentication (e.g., badge reader, biometric, etc.), witness authentication (e.g., separate additional pass code by a witness or manager for access to controlled drugs/narcotics in a drawer 107). Further, the user may be authenticated using a variety of techniques, including, but not limited to, token key, radio-frequency identification (RFID), or a centralized location for network administration and security, such as Active Directory™ from Microsoft® or the OneSign Platform™ (single sign) from Imprivata®, that checks the submitted passcode and authenticates/authorizes the user.

Figure 15:
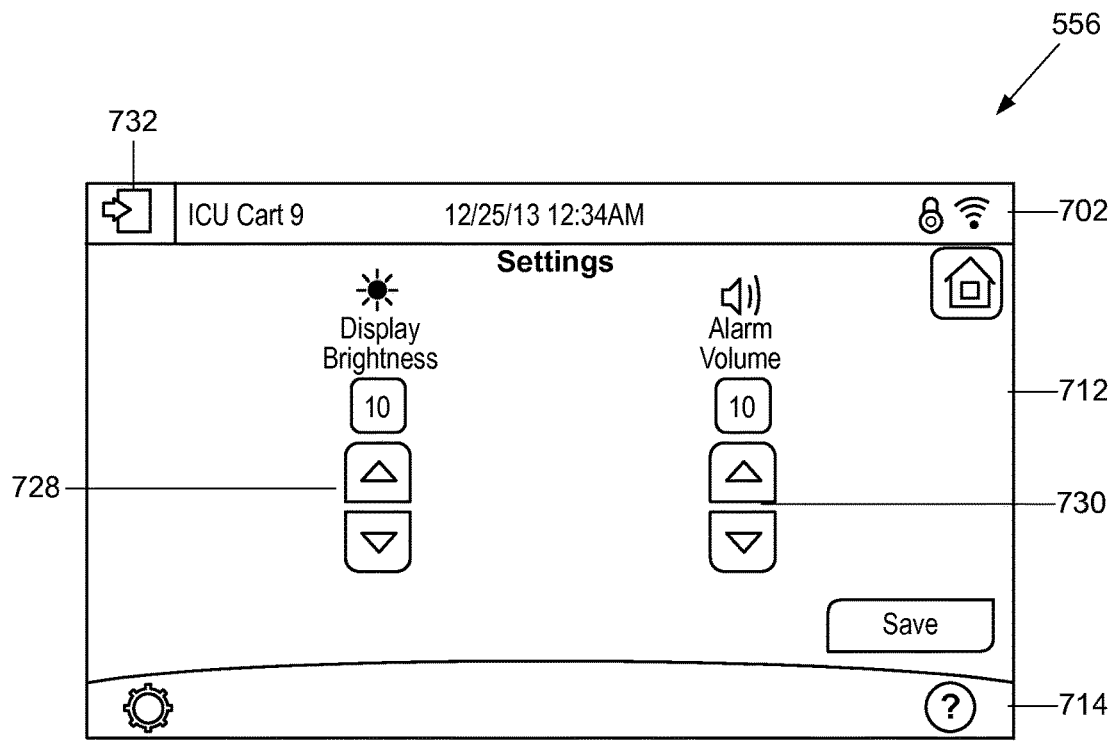
Figure 16:
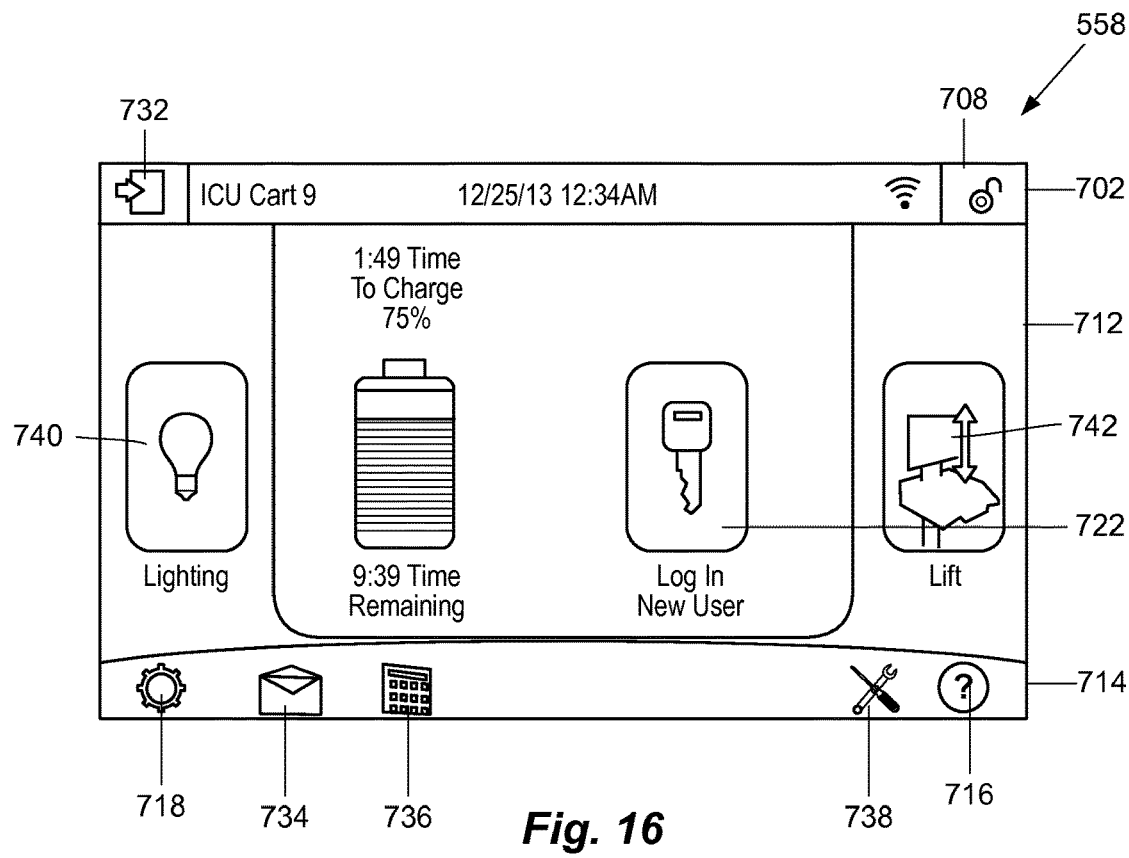

Referring back to FIG. 12, prior to, or as an alternative to, logging in via the pin pad, a user may select the settings button 718, thereby causing the GUI to navigate to a basic settings display 556 (FIG. 15). In the exemplary basic settings display 556 of FIG. 14, the GUI displays rudimentary settings for the medical cart that may be accessed and changed without user authentication. For example, the basic settings display 556 may include controls presented as icons 728 for adjusting the brightness of the display unit 110, such as selectable icons to increase or decrease the brightness, and a text box indicating a brightness index (for example a value in the range of 1 to 10), whereby the controller 402 adjusts the illumination output of the display unit accordingly. The basic settings display 556 may further include controls for adjusting the volume of the medical cart 100 (if provided with a speaker), such as the volume of an alarm (e.g., an alarm to charge the battery 328). Similar to the controls for adjusting the brightness of the display unit 110, the volume controls may include selectable icons to increase or decrease the volume, and a text box indicating a volume index (for example a value in the range of 1 to 10) whereby the controller 402 adjusts the volume output of a speaker accordingly. As further seen in FIG. 15, the GUI updates the information bar 702 to include a return or "logout" button 732, which may return the user to the login display 552 or the pin pad display 554.

Referring to FIG. 12, if the user enters his or her unique passcode, as verified by the controller 402 by comparing the passcode to a list of accepted passcodes, or otherwise verifying the authenticity of the user in accordance with the security mechanism utilized, the GUI navigates to a user home display 558 (FIG. 16), which provides a starting point for the user to access various functions, controls, operations and information for the medical cart 100. In particular, the GUI updates the information bar 702 to include the logout button 732, which, if selected by the user, logs the user out of the medical cart 100 and causes the GUI to navigate back to the login screen 552. The information bar 702 may further be updated to include the user's name and primary group or department (e.g., "Jane Doe—ICU"), which may remain until the user "Jane Doe" logs out of the medical cart 100. Depending on the settings for the cart, the drawers may also be automatically unlocked by the controller 402 upon the user successfully logging in, as indicated by the lock status icon 708.

The GUI also updates the button area 714 to include additional options for the user, such as a notifications icon 734 to navigate to messages and notifications for the user. In one embodiment, the notifications icon 734 may indication the number of new or unopened messages and/or notifications for the user, which may be updated as the user views messages and notifications, and as new messages and notifications are communicated to the medical cart 100. A calculator icon 736 also appears in the button area 714 to allow the user to utilize a calculator tool, and a service icon 738 to allow the user to review the service history for the medical cart 100 and request additional service.

Further controls and options are provided in the content area 712, where the GUI updates the content area 712 to display the login icon 722, except this time to log in a different user (and as a result log out the existing user). Further, the content area 712 is updated to display a lighting icon 740 to control the work lights 130, and a lift icon 742 to adjust the height of the work platform 102.

Figure 17:
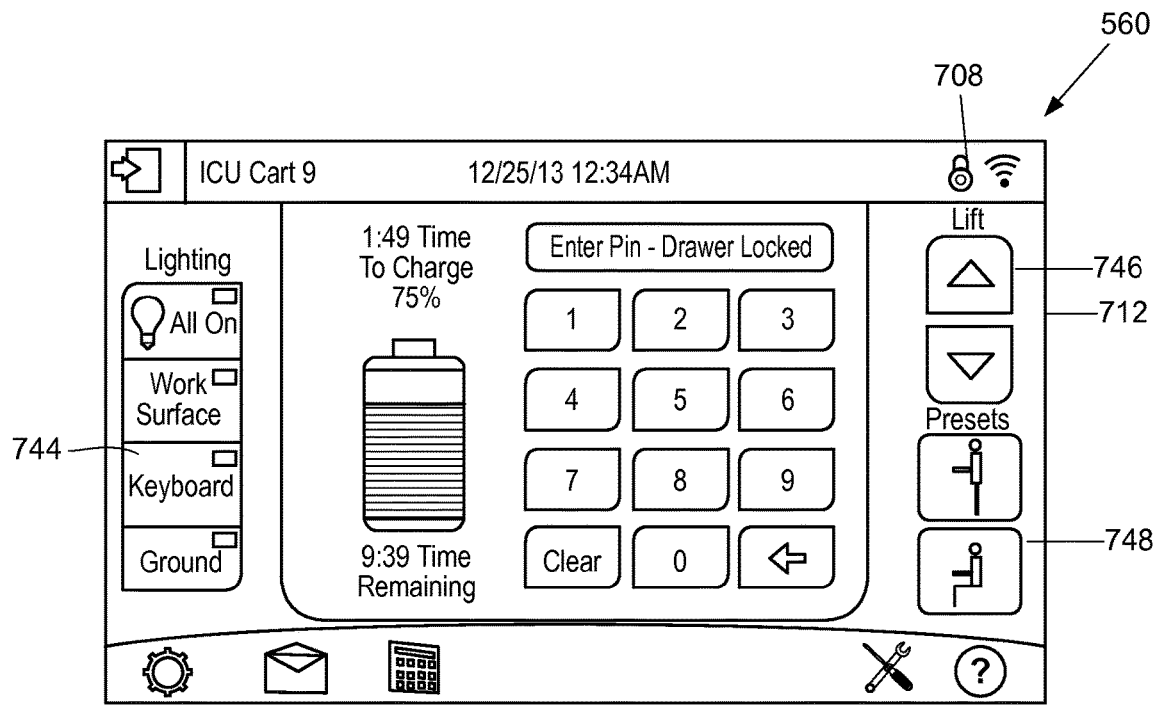
Figure 18:
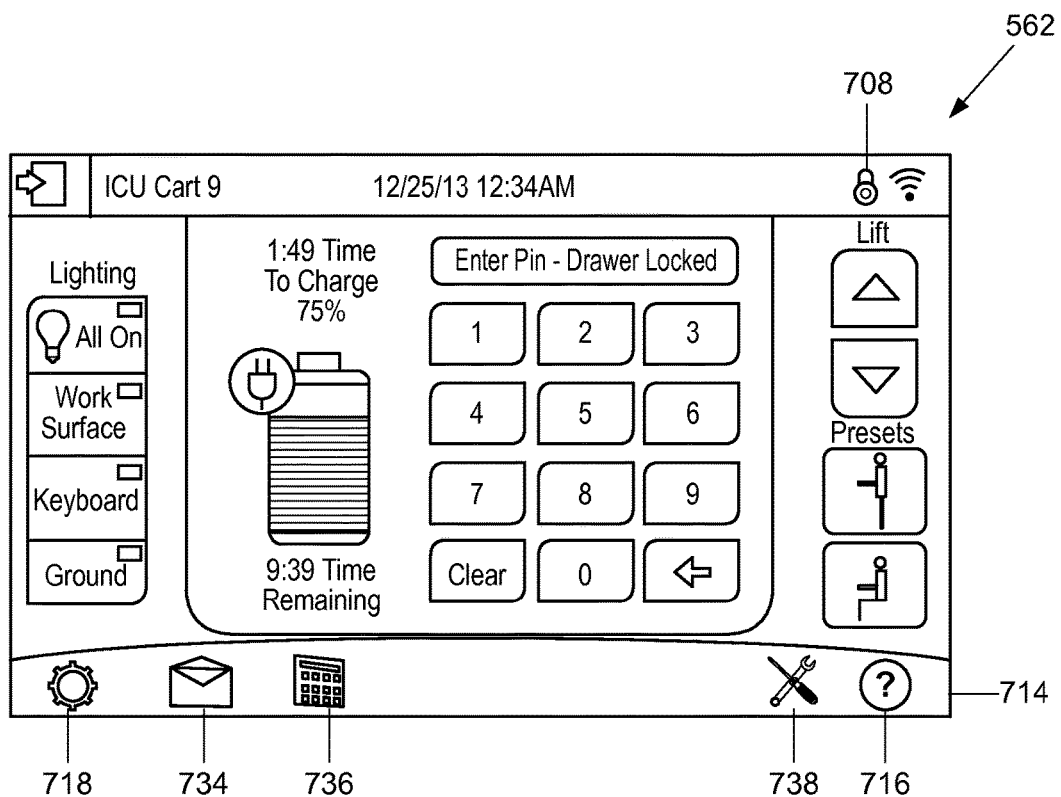

As shown by the two arrows extending from the user home display 558 in FIG. 12, the user may access either the work light controls and/or the lift controls, at which point the GUI navigates to a lighting display, lift display or a combined display of the same (FIG. 17). In the exemplary lighting/lift display 560 of FIG. 17, the GUI displays settings for controlling the work lights 130 and/or the motorized lift 250 (depending on the user's selection) that may then be accessed and changed by the user. For example, the content area 712 is updated to display work light control icons 744, if the user selects the lighting icon 740 of the user home display 558, which includes individually-selectable icons that cause the controller 402 to turn on/off all work lights 130, or turn on/off individual work lights 130, such as those for the illuminating the work surface 108, keyboard platform 148 and ground.

If the user selects the lift icon 742 of the user home display 558, the content area 712 is updated to display lift control icons 746, 748. The lift control icons may include a set of individually-selectable icons 746 to raise and lower the work platform 102, thereby causing the controller 402 to, in turn, engage the control unit 334 to, in turn, cause the actuator 252 to raise or lower the work platform 102 accordingly. In one embodiment, the work platform 102 may be raised and lowered incrementally, such that the user repeatedly touches the icon until the work platform 102 is at the desired height. Alternatively, the user may be required to continue to touch the icons 746 until the work platform 102 is at the desired height.

The lift control icons may further include a set of individually-selectable icons 748 corresponding to preset work platform 102 heights, such as a preset for a standing height and a preset for a sitting height. These presets may be universal settings regardless of user, or may be stored in the memory of the controller 402 as specific user preferences. Regardless, when a user selects one of the presets, the controller 402 reads the corresponding file or data, (such as that for the user's preferences) in the memory, the current height of the work platform (as may be provided based on data from the control unit 334), and causes the control unit 334 to, in turn, activate the actuator 252 to automatically raise or lower the work platform 102 until it reaches the preset height.

Referring again to FIG. 12, at this juncture 562 in the GUI navigation, the path of the GUI may be different depending on the type of user that logged into the medical cart 100. For example, if the user who logged into the cart is identified as a nurse, based on a user profile associated with the entered passcode as stored in the memory of the controller 402, the GUI may display certain functions, controls, operations, and information available only to the nurse, while preventing other functions, controls, operations, and information from being accessed by the nurse. Likewise, if the user is a technician, the GUI may display only certain functions, controls, operations, and information for the technician, while denying the technician access to other functions, controls, operations, and information. Although many of the displays that follow seem similar in appearance, the functions, controls, operations, and information available to different types of users may nonetheless differ depending on the user.

Figure 19:
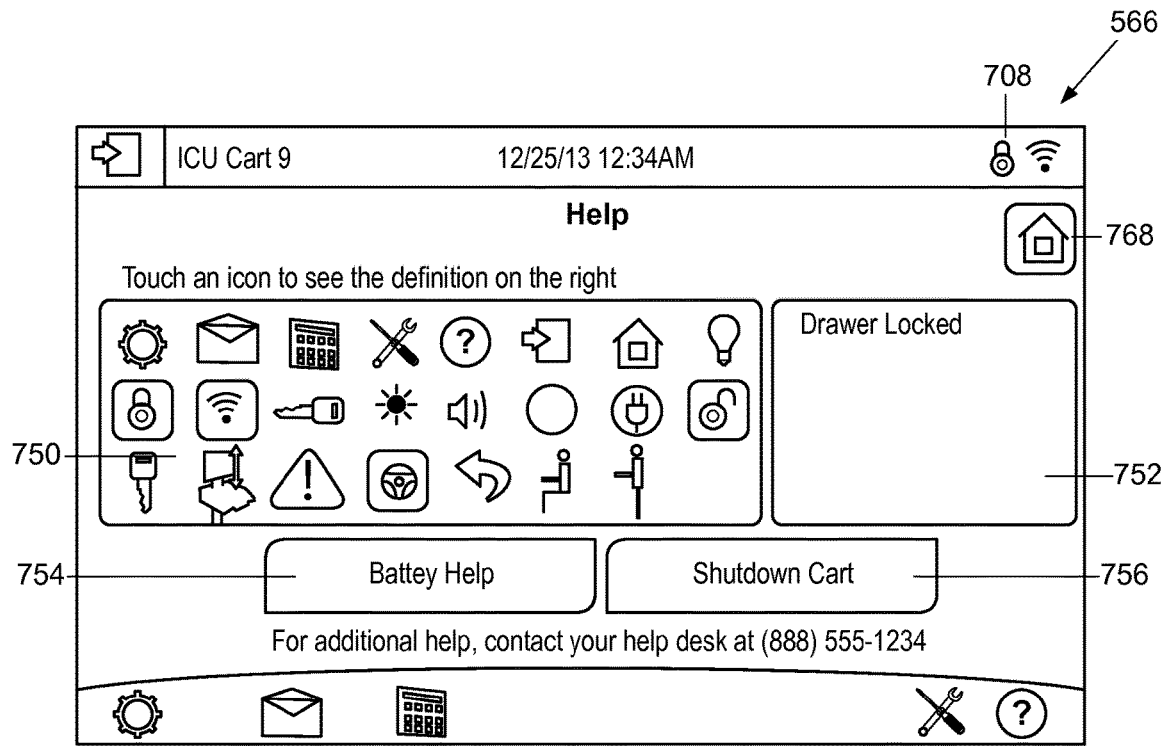
Figure 24:
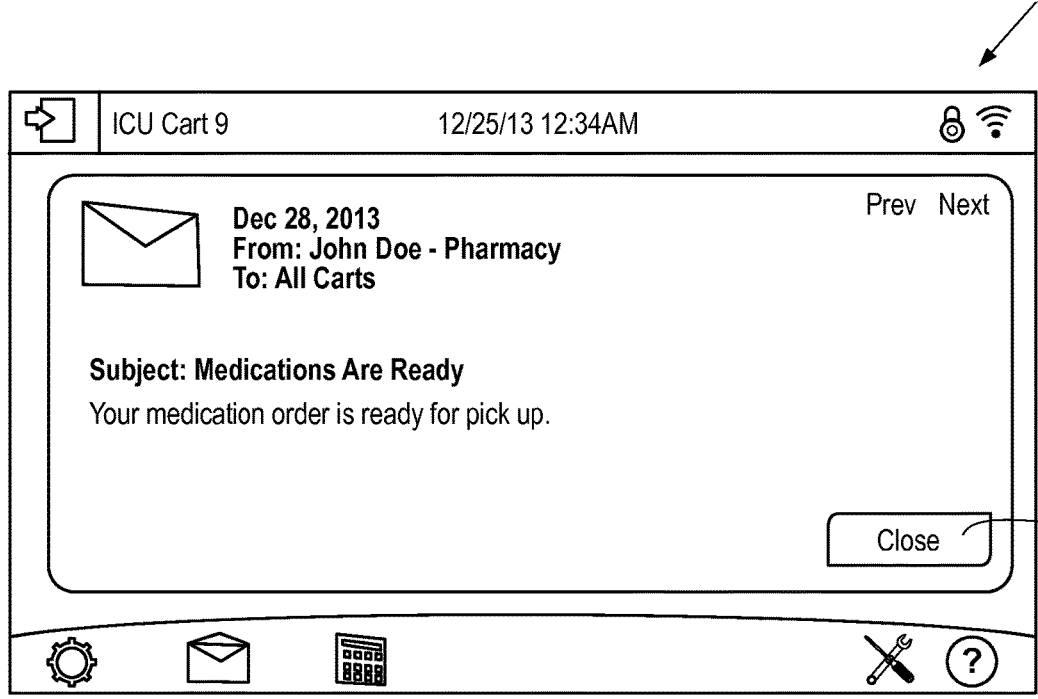
Figure 25:
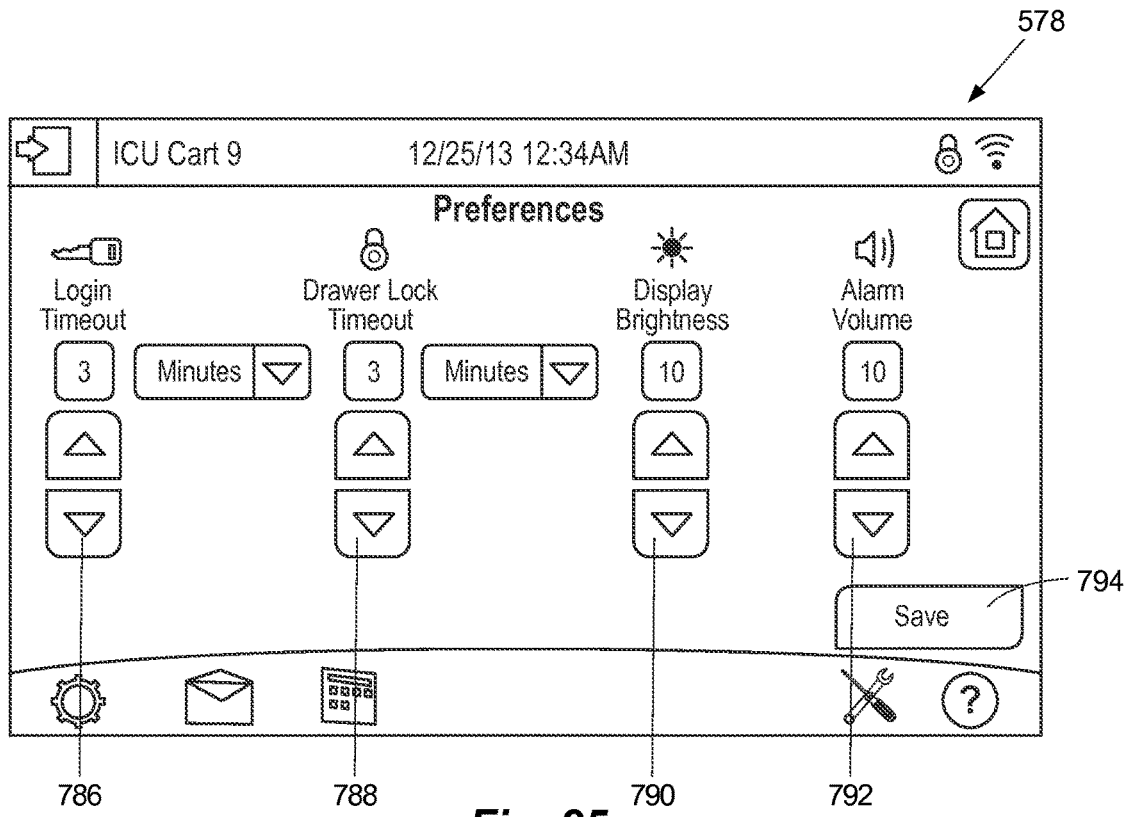

For example, a nurse home display 564 (FIG. 18) is similar to the previous display, be it the lighting/lift display 560 or the access/home display 558. As previously mentioned, the button area 714 includes options for the user, such as a notifications icon 734 to navigate to messages and notifications for the user, a calculator icon 736 to utilize a calculator tool, and a service icon 738 to review the service history and request additional service, a help request button 716 to access a help file within the controller 402, and a settings button 718 to adjust medical cart 100 settings and user preferences. Referring to FIG. 12, if the user selects the help request button 716, the GUI navigates to a help display 566 (FIG. 19). Likewise, selection of the service icon 738 navigates to a service request history display 568 (FIG. 20), and, in turn, a keyboard display 572 (FIG. 21), selection of the calculator icon 736 navigates to a calculator display 572 (FIG. 22), selection of the notifications icon 734 navigates to an notification/message inbox display 574 (FIG. 23), which, in turn, navigates to notifications or message display 576 (FIG. 24) for individual notifications and messages, and selection of the settings button 718 navigates to a user preferences display 578 (FIG. 25).

Referring to FIG. 19, the exemplary help display 566 that is generated when a user selects the help request button 716 provides the user with assistance in navigating the GUI based on help files stored within the controller 402. For example, the help display 566 may include a display 750 of various icons the user may encounter throughout the GUI, whereby a user may select the icon he or she wishes to inquire about, upon which the controller 402 reads the selection, retrieves the information associated with that icon and causes the GUI to display that information in a description area 752. Additional help options available to the user include, but are not limited to, battery help as represented by the battery help icon 754, and a cart shutdown icon 756 to cause the controller 402 to shutdown the medical cart 100. In another embodiment, a system reboot icon may be provided to cause the controller 402 to reboot the end user's computer and/or the settings on the medical cart 100, such as reverting the setting to factory/manufacturer defaults, for example. It is also noted that the help display 566, as well as many of the displays described below for a nurse user include a home icon 758, which the user may select to cause the GUI to navigate back to the nurse home display 564.

Figure 20:
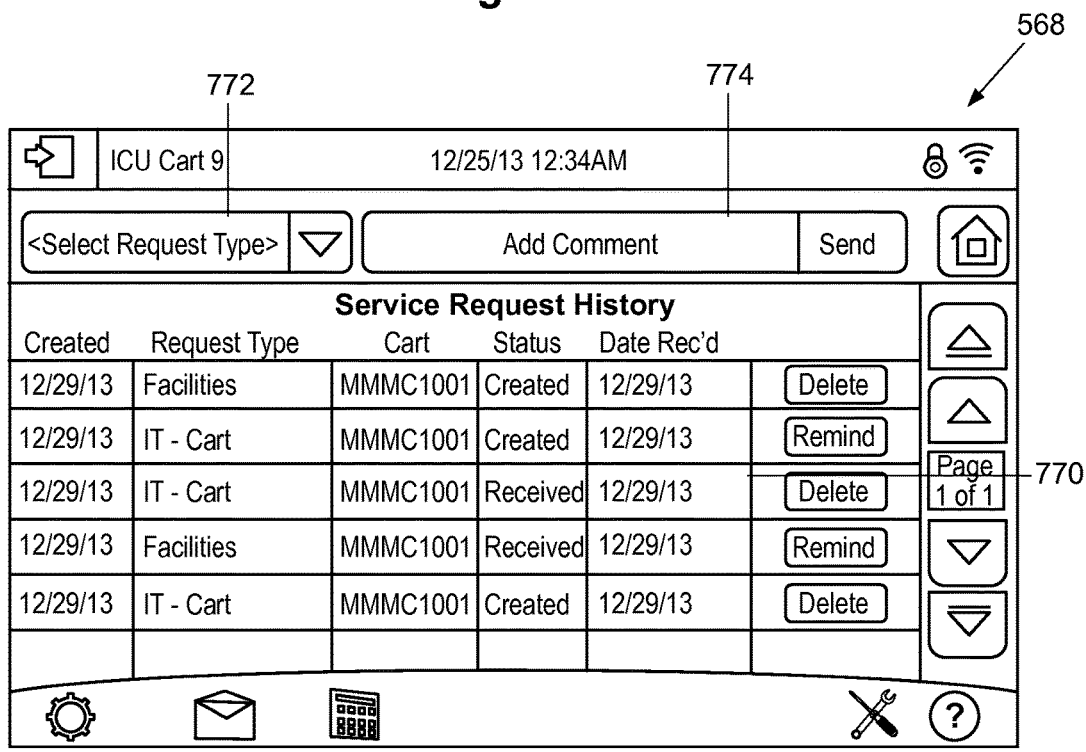
Figure 21:
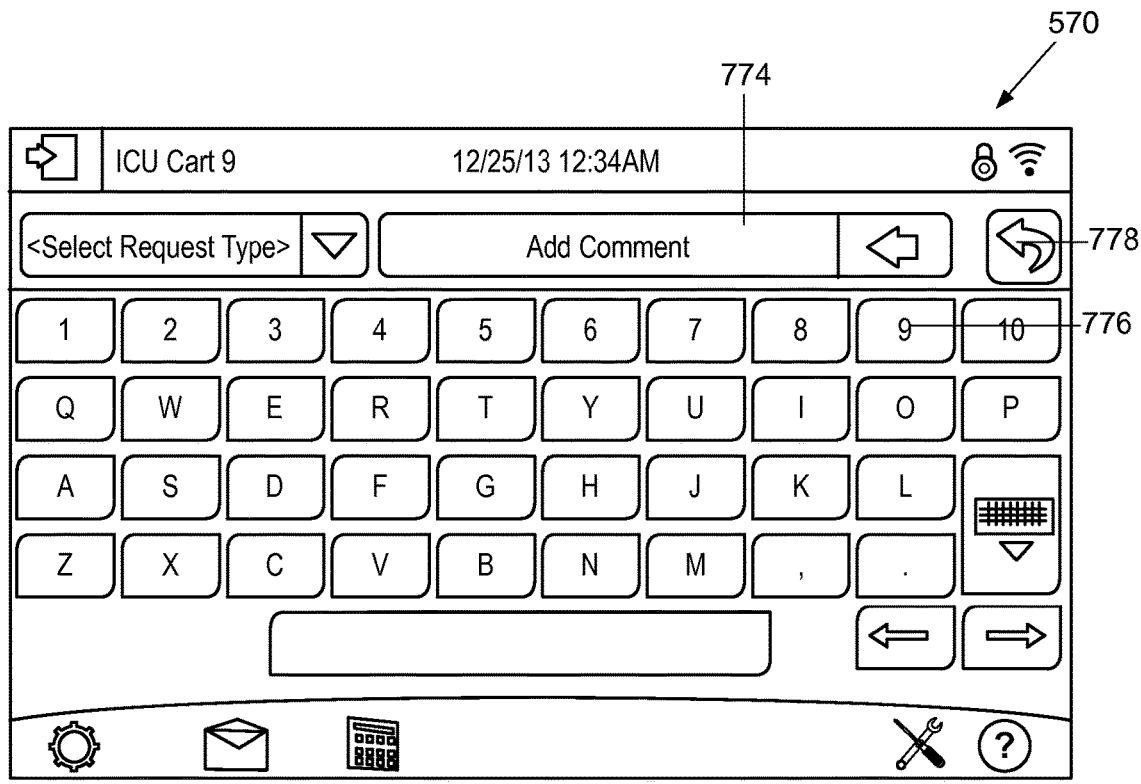

The service request history display 568 of FIG. 20 allows the user to view the service history of the medical cart 100, particularly pending service requests. In one example, a service request is input by a user of the cart and communicated to the fleet management system, which, in turn, may communicate the service request to a service facility, or remotely diagnose the condition of the medical cart 100, and address the diagnosed condition as needed, which may include, but is not limited to, dispatching a technician, pushing a software, firmware or other application to the medical cart 100, generate a remote display, such as a webpage, accessible by personnel in the healthcare facility, etc. In effect, the service request allows the controller 402 to function as a work order generator, which, in one embodiment, results in work orders being automatically generated via the fleet management system to address a problem with the medical cart as specified by a user. However, the type of service is not limited to just servicing of the medical cart 100. For example, the types of services requested may be extended to include housekeeping services, facility services, dietary/nutrition services, etc., where these services may be communicated to different groups or departments within a healthcare entity as necessary, thus allowing the user to facilitate healthcare-related services via the medical cart 100.

The service request history display 568 may include a view 770 of the various service requests, which may include such information as the date the service request was created, the type of request, the medical cart 100 for which the service request was made, the status of the request (e.g., created, received, completed), the date the request was received and options to allow the user to update the request, for example by issuing a reminder (particularly if the request is stale or urgent), or deleting the request (for example, if the problem has been alleviated). Thus, the user is presented with information that allows him or her to readily ascertain whether a problem has already been addressed by a service request, whether that service request has been received, and whether that service request has resulted in action to address the problem.

The service request history display 568 further enables the user to create new service requests. The service request history display 568 includes a drop down menu 772 (or other selection option) to select the type of request (e.g., IT services for an end user computer, IT services for the medical cart 100 generally, IT services for the battery 328, housekeeping, facilities maintenance, nutritional/dietary, etc.), and a selectable text box 774 for the user to provide further details or comments about the service request, such as a description of the problem. Upon selecting the text box 774, the GUI navigates to the keyboard display 570 of FIG. 21, which updates the control area 712 to include an alphanumeric input display 776, such as a display of a QWERTY keyboard, for example. The alphanumeric input display 776 includes a plurality of selectable icons to enable the user to type in any additional comments pertaining to the service request in the text box 774. Once completed, the user may select a back icon 778 to revert back to the service request history display 568, thereby completing the service request. The controller 402 may read the request type, log the date it was created and communicate the request to the fleet management system via the hospital's communication system, whereby the hospital's communication system is essentially utilized as a service provider to an external network, such as the Internet.

Figure 22:
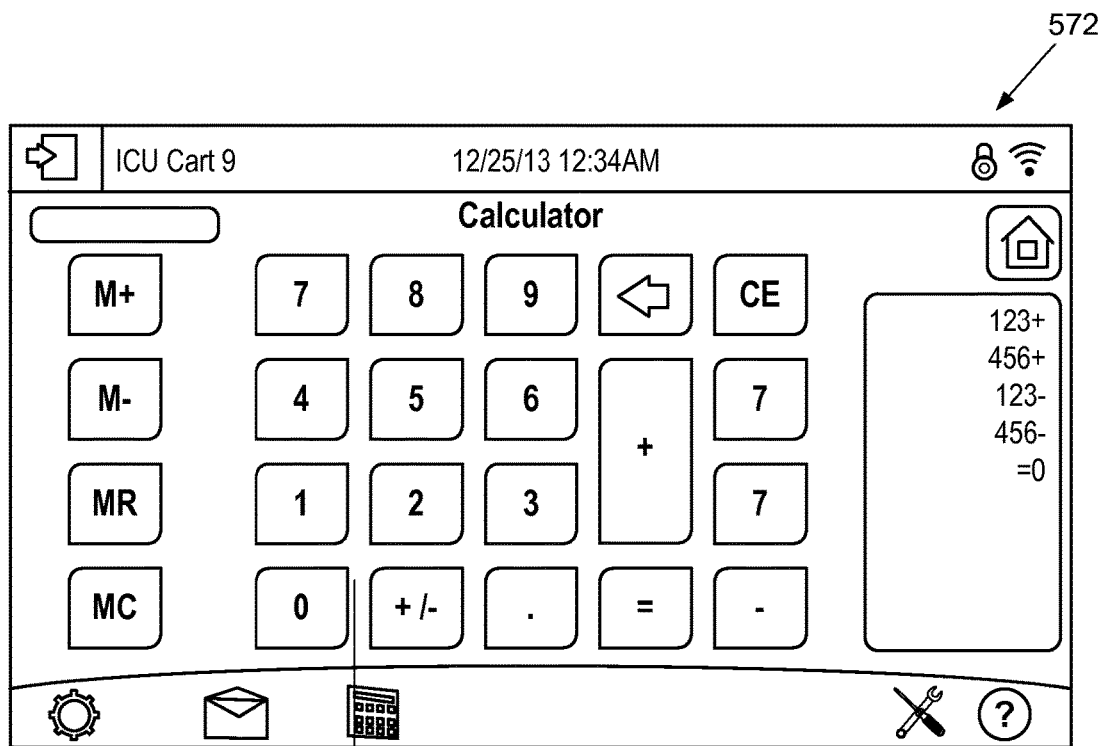

The calculator display 572 of FIG. 22 offers a functional calculator, which may be an application/tool stored in the memory of the controller 402 and executed by the processor of the controller 402. The GUI generates a numeric display, mathematical operators and memory buttons as may be generally found on a standard calculator.

Figure 23:
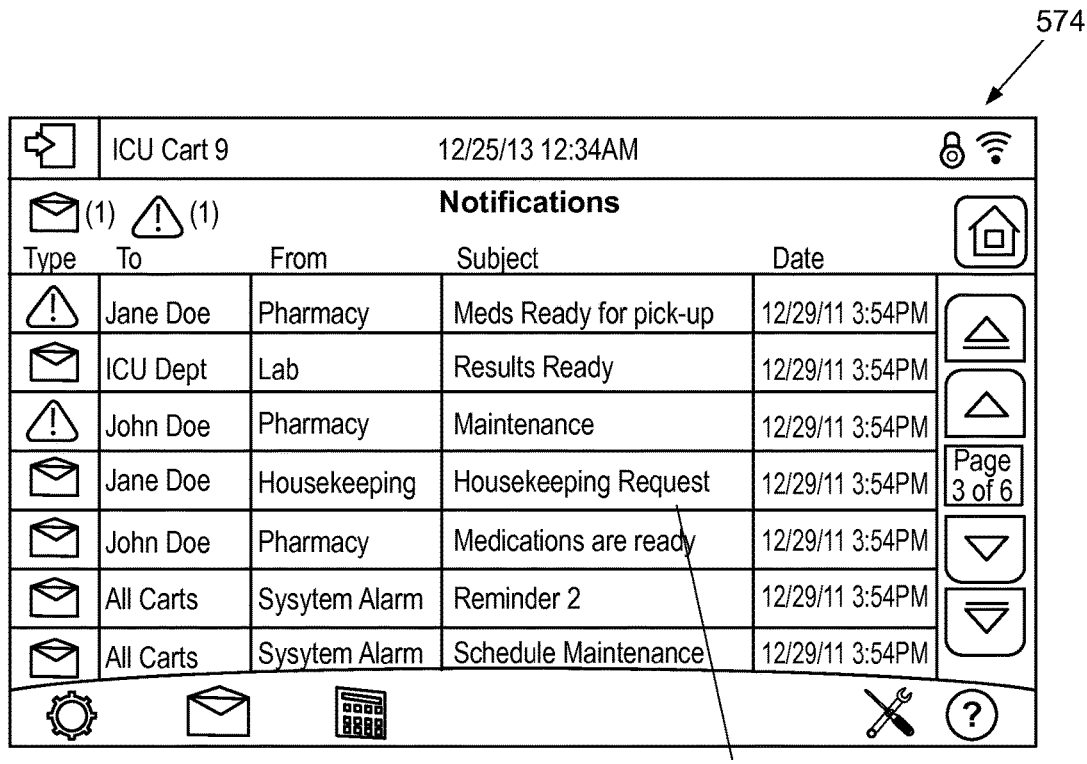

The notifications display 574 of FIG. 23 presents the user with various messages and notifications, either for the user directly or as it pertains to the medical cart 100. For example, the controller 402 may access the email account of the user once the user logs in, such that the user may view email messages addressed to him or her, addressed to the user's group or department, etc. Further, the notifications display 574 may include notifications as they pertain to the medical cart 100, such as service reminders, scheduled maintenance, etc., thus alerting the user to actions necessary as they pertain to the medical cart 100. The messages and notifications are presented in a list 782 detailing the urgency, recipient, sender, subject and date the message or notification was sent.

Each message or notification in the list 782 is selectable by the user. If a message or notification is selected, the GUI may generate a display, much like opening an email, as shown in FIG. 24, where the user may read the contents of the message or notification. Once finished with the message or notification, the user may select a close icon 784 to close out the message/notification and return to the notifications display 574.

The user preferences display 578 that results from selecting the settings button 718 is different than what results from selecting the settings button 718 from the pin pad display 554. Whereas the basic settings display 556 generated by the GUI when the settings button 718 from the pin pad display 554 offers rudimentary settings that may be adjusted by anyone, the user preferences display 578 is customized for the user logged in to the medical cart 100. Here, a user may adjust settings on the medical cart 100 to his or her preferences. For example, a login timeout icon 786 allows the user to specify how long until the medical cart 100 automatically logs the user out due to inactivity, which may be presented as icons to incrementally increase or decrease the time, which is displayed in a text box, and which further allows the user to specify the unit of time involved. The controller 402 then updates the user profile to reflect the new login timeout setting, and adjusts the login timeout setting on the medical cart 100.

The user preferences display 578 may further include a drawer lock timeout icon 788. In particular, one possible feature of the medical cart 100, if provided with drawers 107, includes an automatic drawer unlock time-out. For example, as a precautionary measure to avoid unauthorized access to the drawers 107 even as a user may be logged in to the medical cart 100, an adjustable timer may be set that causes the controller 402 to automatically lock the drawers after a certain period of inactivity (e.g., no interaction with the display unit 110, no drawer opened, etc.). If the drawers are automatically locked once timed out, the lock status icon 708 may change to indicate the drawers are locked, and the control area 712 may be updated to include the pin pad icon 726, thereby prompting the user to re-enter his or her passcode to unlock and gain access to the drawers 107. Here the user may specify how long until the drawer locks engage. As with the login timeout icon 786, the drawer lock timeout icon 788 may be presented as icons to incrementally increase or decrease the time, which is displayed in a text box, and which further allows the user to specify the unit of time involved. The controller 402 then updates the user profile to reflect the new drawer lock timeout setting, and adjusts the drawer lock timeout setting on the medical cart 100.

In some respects, the user preferences display 578 may be similar to the basic settings display 556 of FIG. 14, in that the user preferences display 578 may include controls presented as icons 790 for adjusting the brightness of the display unit 110, such as selectable icons to increase or decrease the brightness, and a text box indicating a brightness index (for example a value in the range of 1 to 10). The user preferences display 578 may further include controls for adjusting the volume of the medical cart 100 (if provided with a speaker), such as the volume of an alarm (e.g., an alarm to charge the battery 328). Similar to the controls for adjusting the brightness of the display unit 110, the volume controls may include selectable icons to increase or decrease the volume, and a text box indicating a volume index (for example a value in the range of 1 to 10).

One difference with the basic setting display 556 is that the settings may be saved as preferences for the user. Once entered, the user may save the preferences by selecting the save icon 794, thereby causing the controller 402 to make adjustments accordingly to the login timeout, drawer lock timeout, display brightness and volume, and saving these setting in a user profile datafile. Whenever the user logs in to the medical cart 100, the controller 402 may automatically read the setting preferences as saved in the user profile, and adjust the medical cart 100 according to those settings. Moreover, the user preferences may be communicated to a central server within the fleet management system. Whenever the user accesses any medical cart, the user's settings may be read by the medical cart, either by requesting the information from the fleet management system, or the fleet management system pushing the information to the medical cart 100 upon detection of the user logging in to the medical cart 100 (for example, the medical cart authenticating the user via the fleet management system or otherwise notifying the fleet management system of the user's access to the medical cart 100).

In yet another alternative, the users preferences may be pushed out to each medical cart 100 that the user may access or has previously accessed. For example, if the user works within a particular group or department, all medical carts for that group or department may maintain a profile for that user, such that the user may use any medical cart 100 within that group or department without having to readjust the settings to his or her preferences, with updates being pushed to those medical carts as changes are made to the preferences and as the medical carts establish communication with the central server. In one embodiment, the fleet management system may maintain data on which medical carts and users are within particular groups or departments, collect the user preferences (or updates to the user preferences) from any of the medical carts within that group(s) or department(s), and push those user preferences to other medical carts within that group(s) or department(s).

Figure 26:
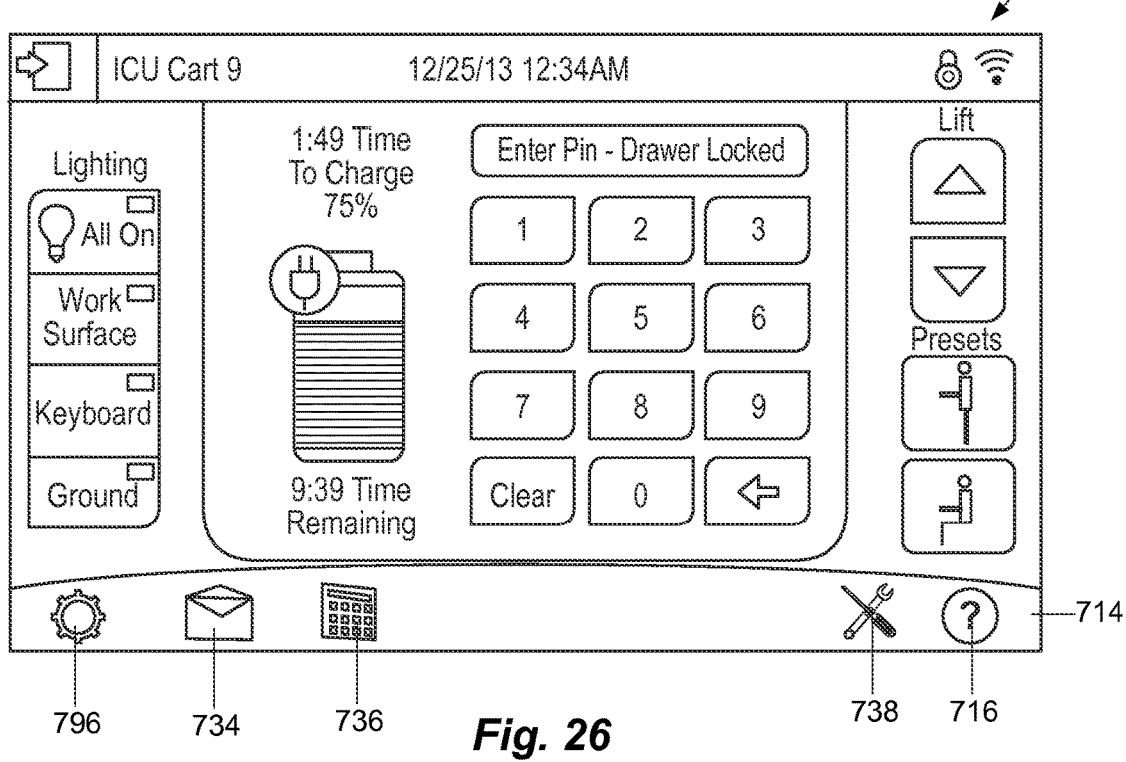
Figure 27:
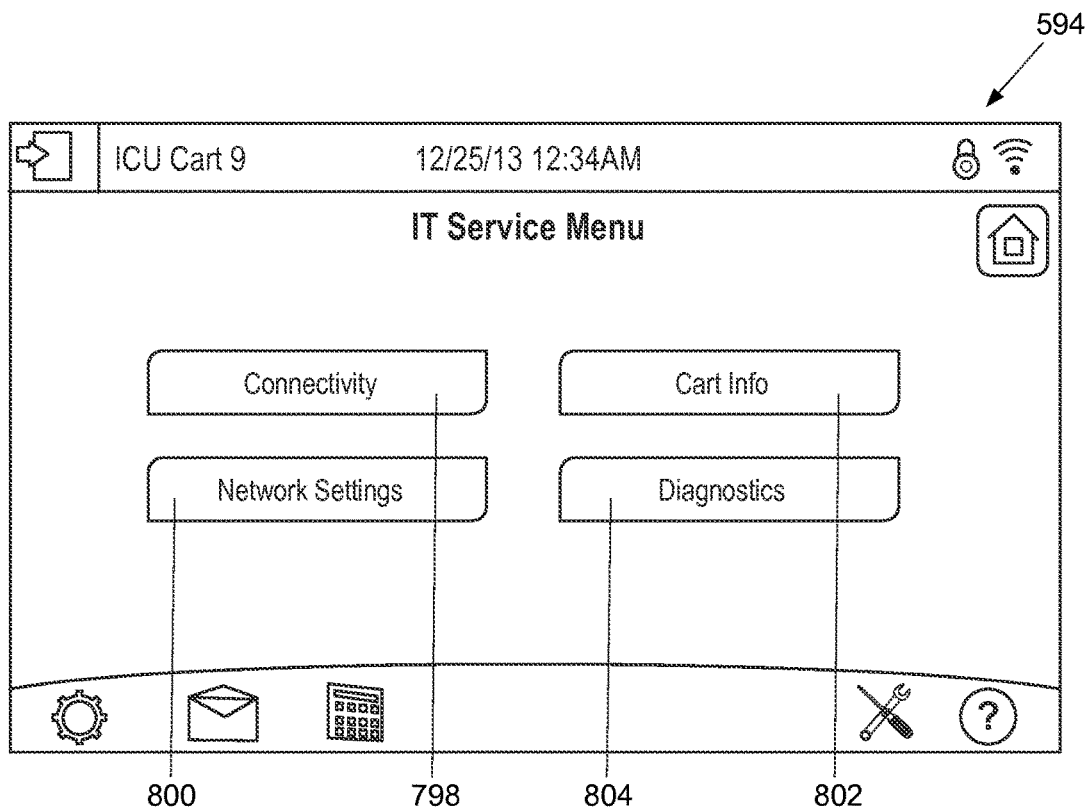

Referring again to FIG. 12, and specifically the juncture 562 in the GUI navigation at which the path of the GUI diverges depending on the type of user that logged into the medical cart 100, the GUI may present different displays pertaining to functions, controls, operations, information, etc. than that described above for the nurse, thereby providing an example of how the GUI may be customized to a particular user. In particular, FIG. 26 presents an exemplary technician home display 580 that may be generated by the GUI when the user logged in to the medical cart 100 and is identified by the controller 402 as being a different type of user, namely a technician. The technician home display 580 is similar to the nurse home display 564 of FIG. 18. In particular, the technician home display is much like the previous display, be it the lighting/lift display 560 of the access/home display 558, and the button area 714 includes options for the technician, such as a notifications icon 734 to navigate to messages and notifications for the uses, a calculator icon 736 to utilize a calculator tool, and a service icon 738 to review the service history and request additional service, and a help request button 716 to access a help file within the controller 402. Referring to FIG. 12, if the user selects the help request button 716, the GUI navigates to a help display 582, which is similar to that shown in FIG. 19. Likewise, selection of the service icon 738 navigates to a service request history display 584 similar to that shown in FIG. 20, and, in turn, a keyboard display 586 similar to that shown in FIG. 21, selection of the calculator icon 736 navigates to a calculator display 588 similar to that shown in FIG. 22, selection of the notifications icon 734 navigates to an notification/message inbox display 590 similar to that shown in FIG. 23, which, in turn, navigates to notifications or message displays 592 similar to that shown in FIG. 24 for individual notifications and messages.

However, as mentioned, the functions, controls, operations, and information available to different types of users may differ, even if slightly. For example, referring again to the technician home display 580 of FIG. 26, rather than including a settings button 718 as in the nurse home display 564, the button area 714 may include a service menu icon or button 796 available only for technicians. Referring to FIG. 12, if a technician user selects the service menu icon 796, the GUI navigates to a service menu display 594 (FIG. 27), which offers options for servicing the medical cart 100, for example in response to service request. Available options from the service menu display 594 are represented by icons that include, but are not limited to, a connectivity icon 798, a network setting icon 800, a medical cart information icon 802 and a diagnostics icon 804. Selection of the cart information icon 802 navigates to a medical cart information display 596 (FIG. 28), selection of the diagnostics icon 804 navigates to a diagnostics display 598 (FIG. 29), selection of the connectivity icon 798 navigates to a connectivity display 600 (FIG. 30) and selection of the network setting icon 800 navigates to a network settings display 602 (FIG. 31).

Figure 28:
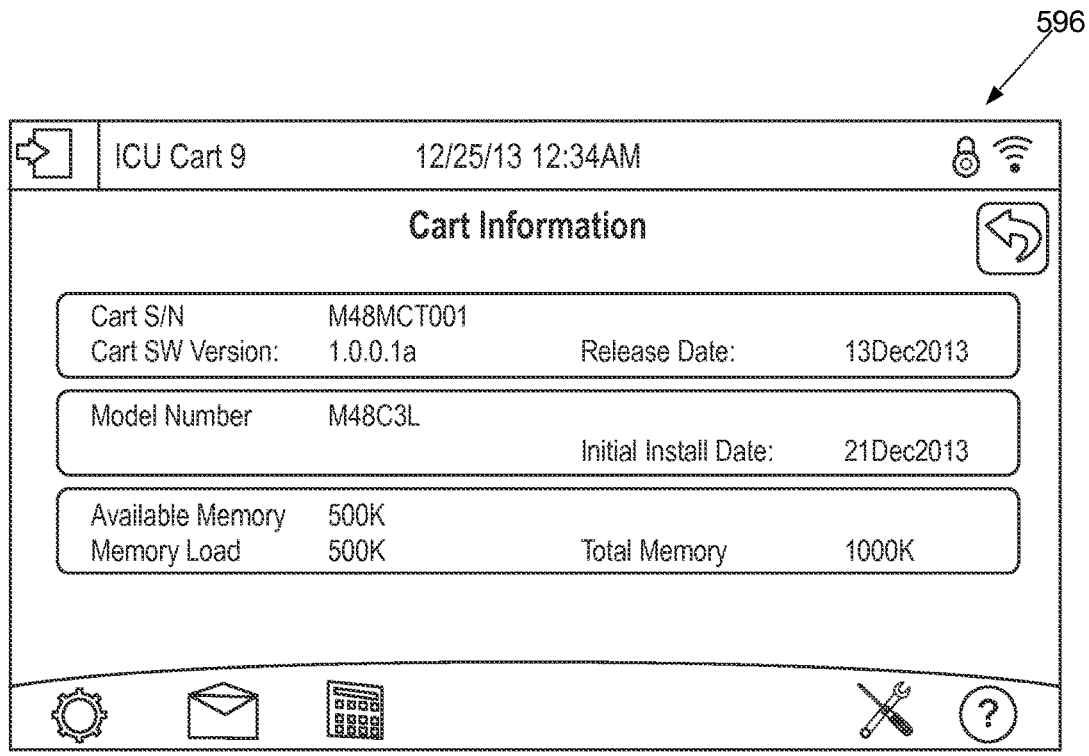
Figure 29:
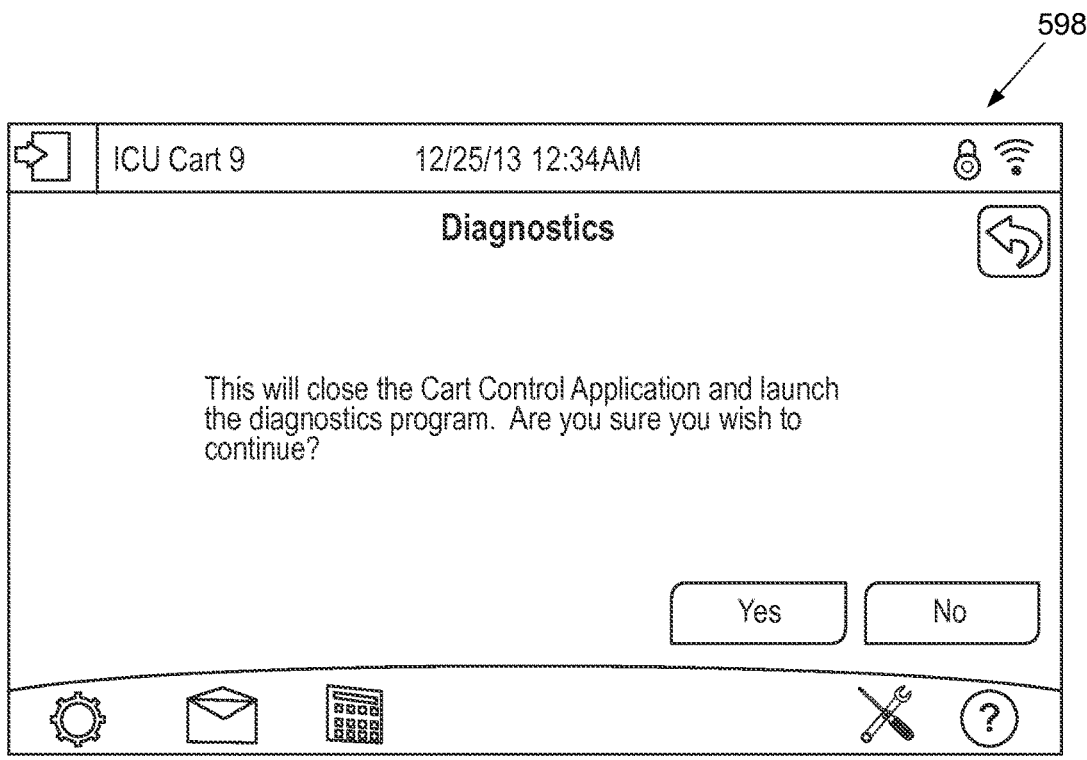

The medical cart information display 596 of FIG. 28 presents the technician user with information about the controller 402, including the latest firmware or software version and available memory, and information about the particular model of the medical cart 100. The diagnostics display 598 of FIG. 29 presents the technician user with the option of having the controller 402 run a self-diagnostic of all sub-systems, installed software/applications, etc. Alternatively, the medical cart 100 may transmit status information about itself, such as the status of the battery 328, status of the controller 402, temperature, service history, etc. to the fleet management system, whereupon the fleet management system may diagnose the medical cart 100 remotely. Selection of this option effectively shuts down the medical cart 100 from further user access as the diagnostic is being performed to prevent interference with the diagnostic.

Examples of the diagnostics, whether executed at the medical cart 100 or remotely at the fleet management system, may include a review and adjustment of communication settings (e.g., detections of a communication interface such as a wireless adapter, whether communications are enabled, network settings, etc.) and medical cart information (e.g., model and serial numbers, sub-system model and serial numbers, power source model and serial numbers, display unit model and serial numbers, distribution board and serial numbers, operating kernel version/revision, firmware versions, etc.). Particular diagnostics may be provided for various operationally important components of the medical cart 100, such as the power source, in which case information such as communication connections (e.g., with the controller 402), current battery charge, service dates, battery and charger voltages, discharge time, discharge current, temperature, faults, events, battery state (e.g., charging, discharging), firmware version, model number, serial number, cycle count, service/warranty dates, capacity (e.g., standard and aged), cycle rating, cycle life de-rating, discharge de-rating percentage/capacity, etc. Even more specifically, the diagnostics pertaining to the battery may be provided such as charging parameters for the battery, including, but not limited to, the battery's minimum charging voltage/current (i.e., the minimum voltage/current at which the battery can safely accept a full charging current), floating charge (i.e., the voltage/current applied to the battery after being fully charged), overcharge (i.e., the maximum battery voltage/current permissible during charging), cycle rating, etc. Various sub-systems may also be diagnosed. For example, a lift diagnostic may provide information about the current lift position, and part/serial numbers, and firmware version. Controls may also be provided to test the lift, such as "stop", "up", "down", and to calibrate the lift. In some cases where the firmware of a component or sub-system may requires revision or reprogramming, the diagnostics may provide various programming modes to update or rollback the firmware version.

Figure 30:
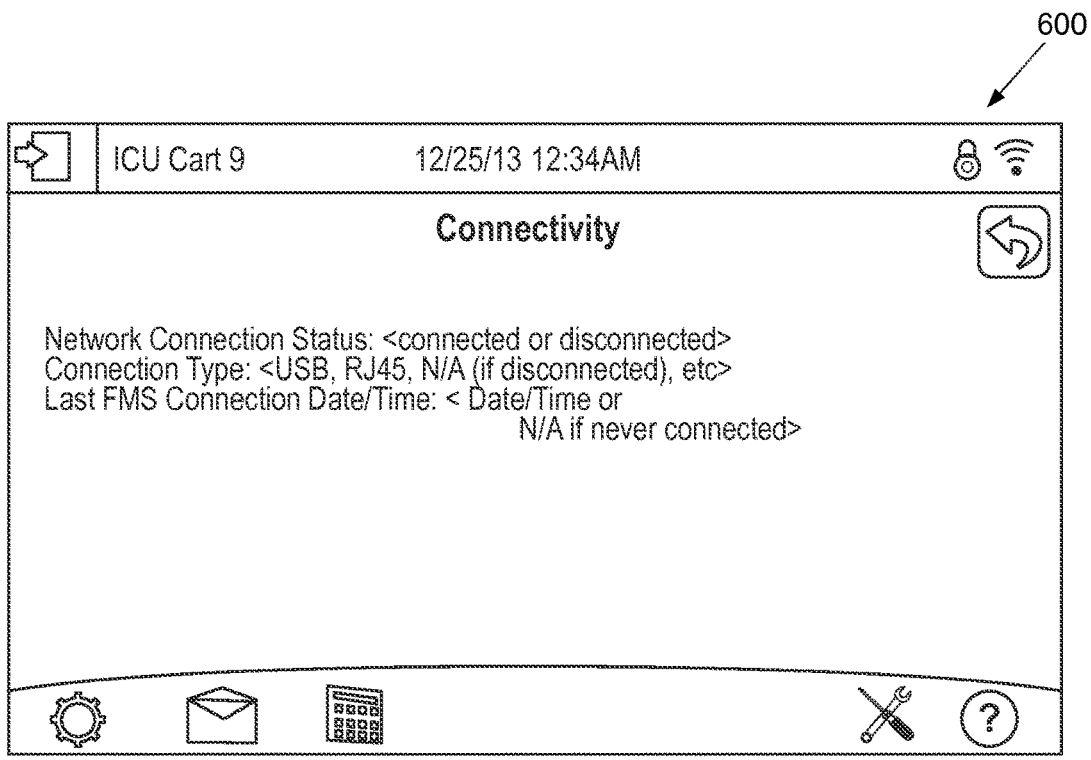
Figure 31:
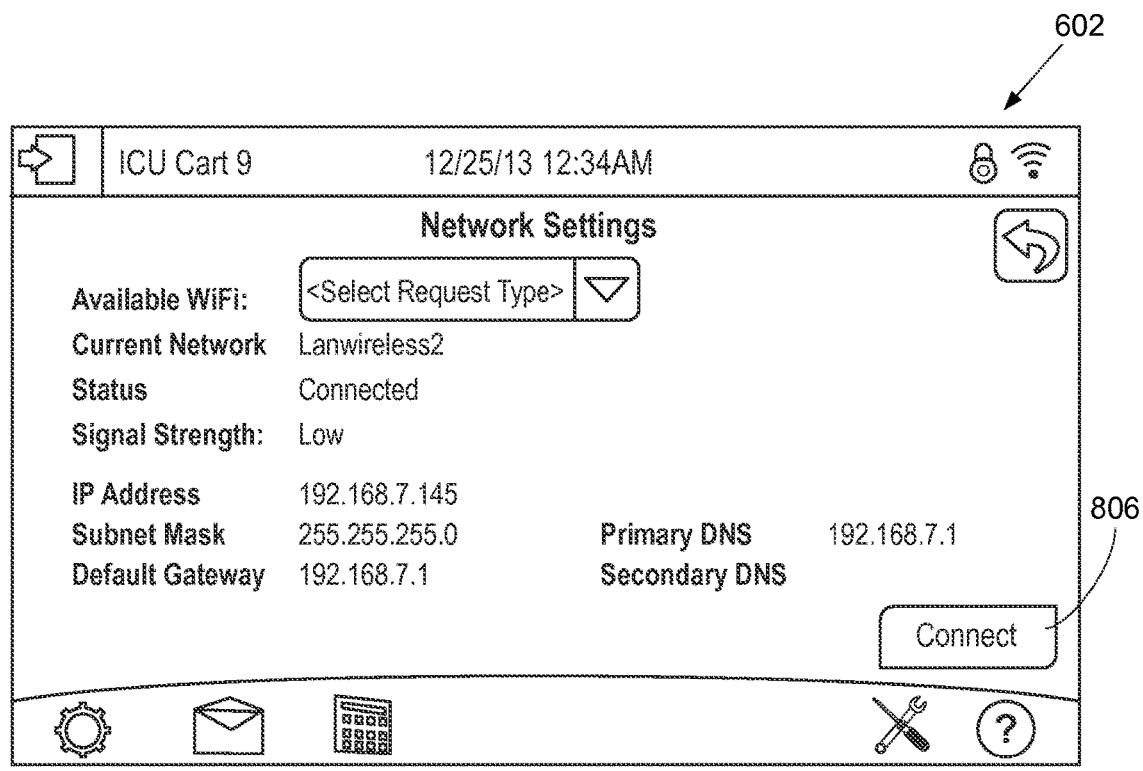

The connectivity display 600 of FIG. 30 presents the technician user with information about the medical cart's communication connection with the healthcare entity server and/or with the fleet management system, including the current connection status, the last time the communication connection was successful and the type of connection involved. The network settings display 602 of FIG. 31 presents the technician user with information about the settings being used by the medical cart 100 to connect to the network, be it the local network of the healthcare entity and/or the fleet management system. If not connected, the network connections display 602 includes a connect icon 806 which may be selected by the technician user to cause the controller 402 to establish, or attempt to establish, a communication connection with the local network of the healthcare entity and/or the fleet management system.

Although FIGS. 12-31 depict one example of the GUI navigational flow and particular examples of various displays, it should be well-understood by those of ordinary skill in the art that the navigation is not limited to that particular flow. For example, it can be readily seen that many of the icons are displayed on multiple displays, each of which is selectable and each of causes the GUI to generate the corresponding display. Thus, a user can navigate to various controls, functions and information from various screens. Moreover, it should be well-understood by those of ordinary skill in the art that the particulars of the displays may be presented differently, in different configurations, with different icon arrangements, different graphical representations, etc. Likewise, as subsystems are added or removed from the medical cart 100, the GUI may be automatically updated to reflect those changes. For example, if the drawers 107 are removed, the controller 402 may update the user controls 456 such that the GUI no longer display information about the drawers, such as lock status, timeout preferences, etc.

Figure 32:
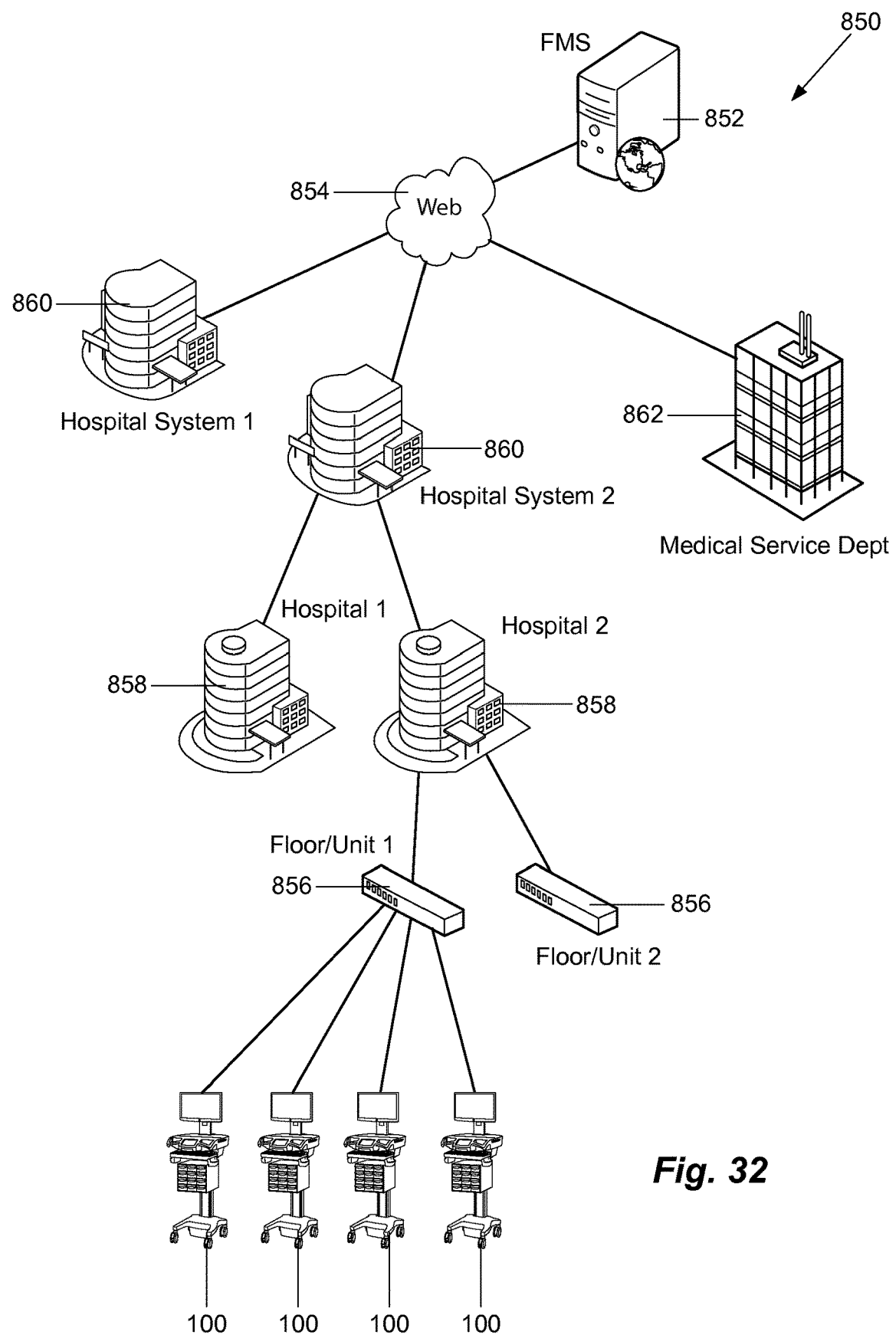
FIG. 32 is an exemplary network diagram of a fleet management system for medical carts in accordance with an embodiment.

FIG. 32 is an exemplary network diagram of a fleet management network 850, including the fleet management system 852. As seen in FIG. 32, the fleet management system 852 is provided from a centrally-hosted, and preferably remote, site via a communication network 854 The communication network 854 may include an open network, such as the Internet, with a secure communication channel to various end-users, though it is understood that other communication networks may be utilized, including, but not limited to, cellular networks, private closed networks, etc. The fleet management system 852 may be hosted, for example, at the manufacturer's location or other third party service provider. Thus, the fleet management system 852 may be provided as a single-hosted website and database maintained by an entity independent of the end-user.

The various entities within the fleet management network 850 may be interconnected in physical and/or logical groups according to various healthcare entities, such as hospital units or floors 856, hospitals 858 and hospital systems 860. Generally, hospitals include interconnected units or floors, and hospital systems (e.g., hospital business entities) generally include hospitals which may be interconnected. In other words, assets related to a hospital 858, including the medical carts 100 or hospitals 858 themselves, may be grouped together to form assets or asset groups at higher levels. Medical carts 100 may be stratified or logically grouped together to form groups or fleets of medical carts 100 within a unit 856 of a hospital 858, such that the medical carts 100 are interconnected via one or more access points, repeaters, routers or other communication system components of the unit 856. For example, all medical carts 100 utilized by an intensive care unit (ICU) may be logically interconnected via a communication system (e.g., access points, repeaters, routers, etc.) for the ICU, which, in turn, communicates with the medical carts 100, and each medical cart 100 is designated as belonging to that unit 856 together forming a fleet of medical carts 100 for the ICU. Additionally, or in the alternative, the medical carts 100 may be logically interconnected according to a physical grouping, such as all medical carts 100 on a particular floor of the hospital 858. Likewise, units 856 may be interconnected with other units 856 to create a hospital 858 fleet of medical carts 100, whereby communication systems (e.g., access points, repeaters, routers, etc.) of the units 856 are interconnected and/or communicatively coupled to additional or higher level communication systems (e.g., access points, repeaters, routers, etc.) for the hospital 858, and each medical cart 100 within that grouping of units 856 is designated as a fleet of medical carts 100 belonging to that hospital 858. In turn, hospitals 858 may be interconnected with other hospitals 858 to create a hospital system 860, and each medical cart 100 within that grouping of hospitals is designated as a fleet of medical carts 100 belonging to that hospital system 860. As a result, a hospital 858 includes numerous levels of hierarchy having interconnected assets at varying levels of hierarchy, including units/floors 856 and medical carts 100, and a business enterprise such as a hospital system 860 may include interconnected hospitals 858.

Each unit 856, hospital 858 and/or hospital system 860 may be provided with a customizable web interface granting access to the data for their particular fleet of carts. The website and database communicate via secure connection web interface or secured communication protocol, such as secure sockets layer or other encryption method, to the unit's, hospital's or hospital system's internet servers, which, in turn, communicate with the medical carts' embedded controllers 402 via the unit's, hospital's or hospital system's communication infrastructure. Each medical cart 100 in the fleet, either at the unit/floor level, hospital level and/or hospital system level, may regularly communicate data to and from the fleet management system 852. Thus, each healthcare entity, such as the hospital systems 860, hospitals 858, units/floors 856, may view up-to-date information on their entire fleet of carts for a variety of aspects and functionalities, including battery performance, power system modes, connectivity, end-user information such as login data, charging behavior, service request history, etc. Additionally, the fleet management system 852 can be used to "push" information to the end-users, one or more medical carts 100, or the entire fleet of medical carts 100 including subsystem firmware updates, software, drawer access, PIN codes, UI notifications for the end-user, etc. The fleet management system 852 may also extend beyond medical carts to other medical systems, including, but not limited to, beds, transfer carts, other mobile devices and equipment, wall mounted medical systems, etc.

Figure 33:
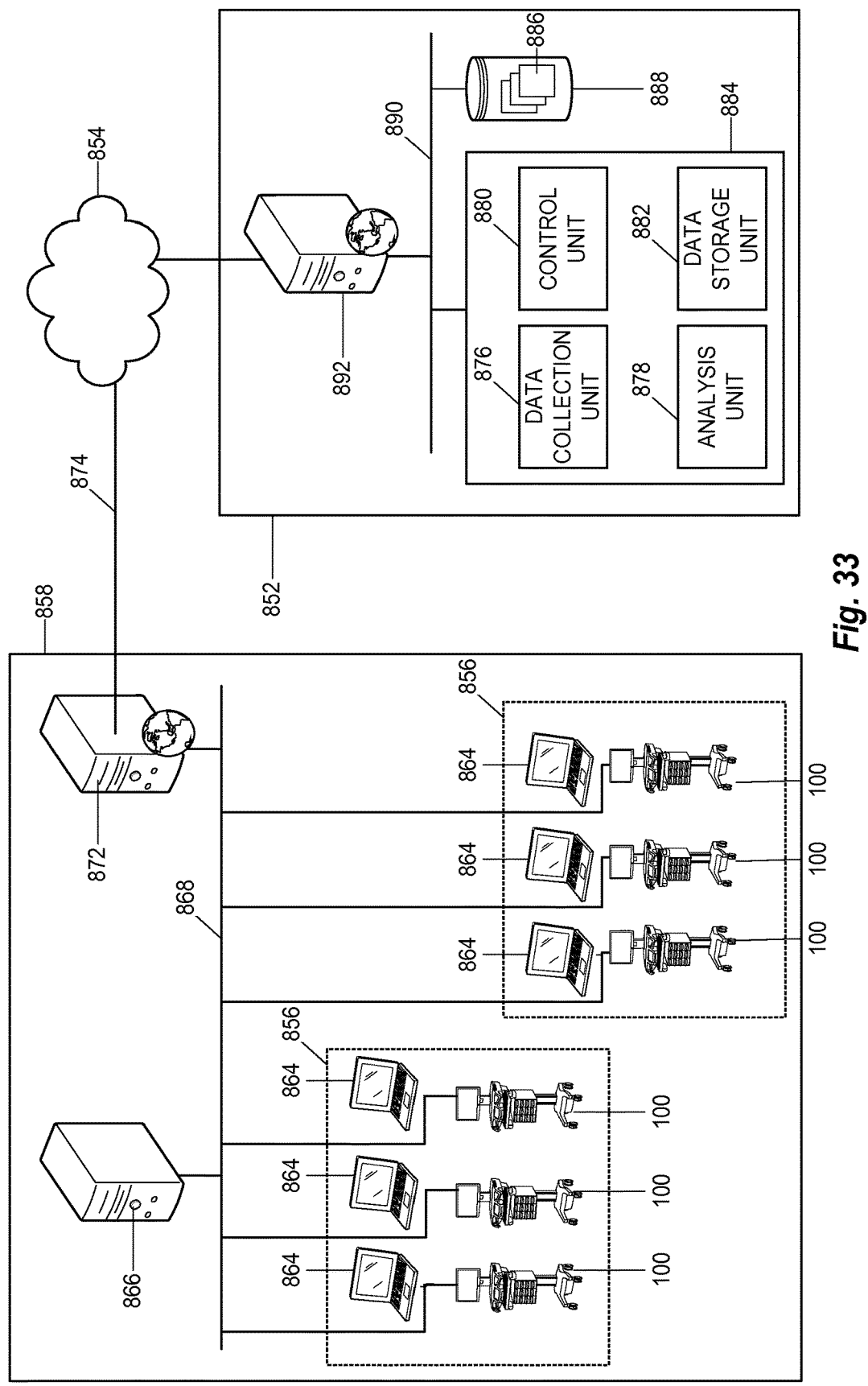
FIG. 33 is an exemplary schematic block diagram of the fleet management system of FIG. 32 in communication with medical carts of a hospital to provide remote services to the medical carts of the hospital in accordance with an embodiment.

FIG. 33 is a more detailed schematic block diagram of the fleet management system 852 in communication with a hospital 858 to provide remote monitoring, diagnostic and maintenance services for medical carts 100 within the hospital's fleet. Although depicted with respect to a hospital 858 and units/floors 856 within that hospital 858, those of ordinary skill in the art will readily understand based upon the detailed description above, and the following description of FIG. 33 how the detailed schematic block diagram may be applied at a higher hierarchical level, such as at the hospital system 860 level, or at a lower hierarchical level and also with respect to clinical health care via telemedicine.

Referring now to FIG. 33, a hospital 858 includes a plurality of medical carts 100 communicatively coupled to a communications bus or network 868. The communications bus or network 868 may be, for example, an Ethernet-based bus that may use any desired or suitable local area network (LAN) or wide area network (WAN) protocol to provide communications, or a wireless-based network that may use any desired or suitable wireless communication protocol. Generally speaking, the medical carts 100 are communicatively coupled to the communications bus or network 868 via communication access points, routers, repeaters, etc. While one or more hospital servers 860 may also be communicatively coupled to the communications bus or network 868, it should be noted that the medical carts 100 are not communicatively coupled to the servers 860 or functionally interact with the servers 860. That is, the medical carts 100 need only utilize the communications system of the hospital (e.g., the communications bus or network 868 and/or a communication server 870), such that the medical carts 100 utilize the hospital network as a network service provider to an outside network, such as the Internet. It is to be understood that the hospital 858 illustrated in FIG. 33 is merely exemplary in nature and other types or configurations of hospitals can be used as well.

As illustrated in FIG. 33 and indicated above, the hospital 858 further includes a communication server 872, for example, a web server, communicatively coupled to any desired open communication network 854 such as, for example, the Internet via a communication link 874. The communication link 874 may be any suitable hardwired link such as a copper cable or other metal wire cable. Preferably, but not necessarily, the communication link 874 includes a fiber optic cable due to the increased bandwidth capacity associated with fiber optic networks. Still further, the communication link 874 may include any suitable wireless link such as, for example, a satellite or cellular phone link. Of course, the communication link 874 may be a hybrid of copper cable, fiber optic cable, and any wireless communication links.

The communication server 872, which may be implemented on a separate computer or workstation having software stored therein, enables the hospital 858 to communicate with the fleet management system 852 via the communication network 854. Alternatively or in addition, the communication server 872 functionality may be implemented within the server 866, if desired. As will be discussed in further detail below, the hospital 858 may send and receive data about the battery 328, controller 402, software or firmware updates, service requests, message and notification, subsystems or any other medical cart information to and from the fleet management system 852 via the communication network 854.

The fleet management system 852 includes a data collection unit 876, an analysis unit 878, a control unit 880, and a data storage unit 882, all of which may collectively form an application server 884. Each of the data collection unit 876, the analysis unit 878, the control unit 880, and the data storage unit 882, is preferably, but not necessarily implemented using one or more software routines that may be executed within the application server 884. In particular, the application server 884 may include one or more processors having associated memory that store and execute a number of routines to perform the steps of collecting data associated with each medical cart 100 or fleet of medical carts 100, analyzing the collected data to detect a condition, including past, present and projected conditions (e.g., trend analysis), associated with the medical cart 100 or fleet of medical carts 100, and automatically implementing an appropriate software application 886 in response to the detected condition. Of course, the processor may be a microprocessor, microcontroller, Application Specific Integrated Circuit (ASIC), or other processing device that is configured or programmed to perform the various data collection, control, and analysis activities described in further detail below.

As illustrated in FIG. 33, the application server 884 is in communication with a database 888 via a bus 890. The bus 890 may be an Ethernet-based LAN or WAN, or any other suitable bus. The database 888 stores a plurality of software tools or applications 886 that perform monitoring, diagnostic and/or maintenance activities for the medical carts 100. More specifically, the software applications 886 may include a battery monitoring application, a usage application, a cart calibration/configuration application, a medical cart utilization balancing application, a messaging and notification application, a work/service order generation application, a user preferences/profiles application, a medical cart access application, or any other applications related to monitoring, diagnosing, and/or monitoring the medical carts 100. Although all applications 886 are built into a single user interface, in another embodiment the applications 886 may be provided as separate, standalone applications each having its own user interface.

In particular, the data collection unit 876 may be configured to automatically collect and store data from the medical carts 100 via the communication network 854 in real-time as the process is running, or at periodic intervals, either by polling the medical carts 100 for the data and/or having the controller 402 programmed to automatically send the data to the fleet management system 852. The data collection unit 876 may collect this data directly from one or more of the medical carts 100. Alternatively or in addition, each medical cart 100 may collect data associated with the medical cart 100 when the medical cart 100 is not in communication with the fleet management system 852 and send that data to the fleet management system 852 once communication is reestablished. For example, the medical cart 100 may include an expert data collection tool or application stored in the controller 100 for insuring that the proper data is sent to the fleet management system 852 in a timely or periodic manner, particularly during periods where the medical cart 100 is out of communication with the fleet management system 852.

The collected data may include data pertaining to logins and logouts, voltage levels (indicative of use/nonuse), the time and length of usage, communication access points within the hospital, configuration information such as installed subsystems and devices, battery usage and performance, charging times and lengths, access logs, service requests, user preferences, passcodes and user lists, software/firmware installed for the controller 402 and smart subsystems/devices, connection activity between the medical cart and the fleet management system, and any other data associated with the medical cart 100. In particular, the data collection unit 876 may collect data that may be used to determine cart usage (e.g., compare groups, individual carts, individual users, etc. against averages and best practices of other users, groups, hospitals, etc.), battery performance (e.g., capacity, average charge rates, average charge levels), faults (e.g., battery over current, battery over temperature, software or driver failure, subsystem initialization failure, CAN bus receive error, device failure, power system initialization failure, communication protocol failure, no model number, no serial number, command format failure, CAN bus communication failure, command error, etc.), alarms and events (e.g., power supply failure, battery failure, lift malfunction, drawer access malfunction, etc.), medical cart connectivity and movement (e.g., non-communicating medical carts, connection intervals, medical cart locator/tracking based on access points, such as the number of access points, percentage of time by access point, etc.), usage/load (e.g., usage hours, average power/charge used, etc.), access monitoring (e.g., logins, drawer access by user and/or medical cart, etc.), user charging behavior (e.g., the charge of the battery as left for the next user, minimum charge capacity level reached after charging while logged in, idle medical carts (i.e., not used and not being charged), etc.), usage of notifications and service requests (e.g., types of service requests, breakdown of alerts and messages sent by fleet management users, etc.), and any other data generated by the medical carts 100.

Upon receiving the collected data, the analysis unit 878 may detect a condition associated with the medical cart 100. For example, the analysis unit 878 may determine which medical carts 100 associated with the hospital 858 or unit 856 have one or more subsystems approaching failure, such as the battery if battery capacity is decreasing based on trends from evaluating current and past battery capacity. The analysis unit 878 may also determine that the vents of the power source are clogged based on the temperature of the battery 328 and/or the power source 314 as a whole. In addition, the analysis unit 878 may determine which medical carts within the hospital 858 or unit 856 are being overutilized or underutilized. The analysis unit 878 may also determine user behavior and usage of a cart over time, such as by monitoring a user's habits in recharging the battery based on the times the user uses the medical cart and leaves the medical cart idle, length of charge, and battery charge level relative to capacity. Similarly, the analysis unit 878 may determine faults, alarms and events based on service requests and failure notifications from the medical cart. Further, the analysis unit 878 may determine whether the medical cart and/or its subsystems have the latest software or firmware updates based the configuration of the medical cart (e.g., installed software, firmware and subsystems) and on data about the software/firmware versions currently installed in its subsystems, and comparing that data to a list of the latest versions of that software or firmware. Still further, the analysis unit 878 may determine whether a request has been received, such as login access request, drawer access request, service request, etc.

If desired, the analysis unit 878 may compare the collected data with one or more stored parameters to determine if the collected data are within an acceptable range. For example, the analysis unit 878 may compare a statistical measure (such as the mean, median, etc.) of the battery capacity, usage, charge time, etc. over a predetermined period of time and/or the actual or instantaneous value of the measurement to a specific operating range or limit to detect an out-of-range measurement. Similarly, the analysis unit may compare the collected data with data from other medical carts 100, either in the same unit, hospital or hospital system, and compare that to data from other medical carts in the same unit, hospital or hospital systems, or to data from other medical carts in other units, hospitals or hospital systems, to determine best practices based on actual usage by end users. For example, if battery usage and performance is more optimized based on the user behavior and usage of one medical cart, that analysis may be used in comparison to the user behavior and usage of other medical carts to identify sub-optimal usage, including, but not limited to, battery usage, charging behavior, charge times, etc.

Further, by examining the appropriate bit flag of an error parameter generated by one of the medical carts 100 during an alarm or event, the analysis unit 878 may determine whether an alarm or event requires immediate corrective action because it is limiting the operation of the medical cart 100, or whether the alarm or event is associated with a condition that is not critical to, or which would not adversely affect, the usage of the medical cart 100, and therefore does not require immediate action. In a similar manner, the analysis unit 878 may examine the type of service requested in a service request to determine the expediency of servicing the medical cart 100. In yet another example, the analysis unit 878 may determine where medical carts are being utilized or not utilized, as well as which medical carts are being utilized higher than average, which medical carts are being utilized lower than average, including usage based on time and location. Of course, any other desired processing of the collected data could be performed using any known techniques or available applications.

The fleet management system 852 further includes a communication server 892, for example a web server, communicatively coupled to the communication network 854 via a communication link 894. As with communication link 874, the communication link 894 may be a hardwired link, a wireless link, or any desired combination of hardwired and/or wireless links. The communication server 892 associated with the fleet management system 852, which may be implemented on a separate computer having software stored therein, enables the fleet management system 852 to receive data and information from, and send information to, the medical carts 100 via the communication network 854 and via the hospital communication system, such as the communication server 872 and bus 868. Alternatively or in addition, the communication server 892 functionality may be implemented within the application server 884.

While the software routines making up the application server 884 are described as being stored and executed in a distributed manner using a plurality of processing units (i.e., the data collection unit 876, the analysis unit 878, the control unit 880, and the data storage unit 882) that are communicatively coupled to each other, it should be understood that the software routines of the application server 884 may be stored and executed within a single processing unit. Furthermore, each of the data collection unit 876, the analysis unit 878, the control unit 880, and the data storage unit 882 need not be located within a single server computer at a single location. Rather, one or more of the units 876, 878, 888, 882 may be located at different geographical locations from each other, and adapted to communicate with each other via, for example, the Internet. Still further, while FIG. 33 shows the plurality of software applications 886 being located in a database 888 that is separate and distinct from the application server 884, it should be recognized that the software applications 886 could, instead, be stored and executed within the application server 884 itself.

During operation, the analysis unit 878 analyzes the collected data to detect one or more conditions associated with the medical carts 100 in accordance with a set of stored rules or other algorithms. Upon detecting a condition, the analysis unit 878 produces a condition indication indicative of the detected condition, examples of which have been described above. The condition indication may be one of a plurality of predefined conditions stored in the analysis unit 878. In response to the condition indication, the control unit 880 may automatically implement an appropriate software application 886 to further analyze the detected condition and/or to correct the detected condition. Generally speaking, the control unit 880 may automatically implement the appropriate software application 886 based on the type of condition (e.g., subsystem failure or imminent failure, under/over utilization, inefficient usage/performance, access request, suboptimal user behavior such as poor charging times, lack of charging), the nature or identity of the source of the condition (e.g., whether it originated from the medical cart 100 or from a user via a service request, etc.), or any other desired criteria.

Similarly, the analysis unit 878 may determine faults, alarms and events based on service requests and failure notifications from the medical cart. Further, the analysis unit 878 may determine whether the medical cart and/or its subsystems have the latest software or firmware updates based the configuration of the medical cart (e.g., installed software, firmware and subsystems) and on data about the software/firmware versions currently installed in its subsystems, and comparing that data to a list of the latest versions of that software or firmware. Still further, the analysis unit 878 may determine whether a request has been received, such as login access request, drawer access request, service request, etc.

The control unit 880 may automatically execute the appropriate software application 886 locally at the fleet management system 852 and calculate parameters to, for example, monitor and/or troubleshoot the medical carts 100. In particular, the control unit 880 may use the load balancing application to calculate parameters for optimizing/balancing the load or usage of medical carts 100 within a particular group, such that usage of the medical carts are more evenly distributed across the group and across time. For example, where usage of medical carts 100 peaks during daytime hours, underutilized carts during that time may be identified for usage during non-peak hours while over-utilized carts are identified for charging and/or service. Thus, the control unit 880 may use the load balancing application to create a schedule that optimizes medical cart usage within a group and communicate that schedule to the hospital or group.

Further, the control unit 880 may use the battery monitoring application to identify a failed, or soon-to-fail battery of a medical cart 100 based on the analysis unit identifying a poorly performing battery. In turn, the control unit 880 may use the work/service order generation application to automatically notify a technician, either at the hospital 858 and/or the service facility 860, to exchange the battery. Alternatively, or in addition, the control unit 880 may use the work/service order generation application to automatically order and deliver a new battery to the hospital to exchange the failed or failing battery.

The control unit 880 may also use the usage application to identify poor usage habits on the part of the user. For example, if a particular user uses medical carts in a suboptimal manner, such as by using a medical cart before it is fully charged (particularly if other medical carts were available), failing to charge the cart for the next user or leaving the cart in an idle state, the control unit 880 may automatically generate and communicate a message or notification to the user or a technician, reminding the user or technician of proper usage of the medical cart 100 and identify training needs.

In a similar manner, if the detected condition means a cart requires service and/or should not be utilized, for example due to a fault, event, alarm or service request, the control unit 880 may use the medical cart access application to automatically communicate a signal to the medical cart 100 locking out all users, and/or use the messaging notification application to notify users that the medical cart should not be utilized, and/or further using the work/service order generation application to submit a message or notification to service personnel, such as a technician in the hospital or in the service facility 862 requesting service of the medical cart 100. In using the work/service order generation application, the control unit 880 may cause a work order to be automatically generated for the service personnel, including a scheduling for service based on an urgency calculated based on the severity of the detected condition, such as subsystem failure or imminent failure based on known parameters, information about the detected condition and information for addressing the detected condition and/or services the medical cart 100.

In yet another example, in response to a request for access, the control system 880 may utilize the medical cart access application to verify the authenticity of the user requesting access, for example by comparing the passcode provided by the user (such as that entered in an attempted login), to a list of authorized users for that medical cart 100 and associated passcode for those authorized users. Provided there is a match, or the user is otherwise authenticated, the control system 880 may generate and transmit a signal to the medical cart 100 granting the user access or unlocking all, or selected ones of, the drawers 107 of the medical cart 100, as well as resetting the users passcode and using the messaging and notification application to transmit the new passcode to the user.

In any event, the fleet management system 852 may communicate the calculated parameters to the hospital 858 via the communication server 892, the communication network 854 and the hospital communication server 872. In particular, the fleet management system 852 may communicate the calculated parameters to individual medical carts 100. Of course, the fleet management system 852 may also communicate the calculated parameters to the additional third parties, such as a technician at the service facility 860.

Alternatively or in addition, the control unit 880 may use the cart calibration/configuration application to automatically download the appropriate software application 886 to the medical cart 100. The software applications 886 may then be implemented under the direction of the control unit 880, in the appropriate sequence, and at the appropriate times to carry out the desired actions. For example, the software application 886 downloaded to a medical cart 100 may be a firmware or software update where it has been determined that the medical cart 100 or one of its subsystems lacks the latest version. In another example, the software application 886 may be a diagnostic routine that may be executed by the controller 402 of the medical cart to run a self-diagnostic in response to a detected condition (e.g., low battery capacity, abnormal operating temperature, etc.).

Still further, the control unit 880 may activate a web page providing graphical and/or textual information such as, for example, instructions from an operator's manual for the medical cart 100, for guiding a user or technician at the hospital 858 in manually troubleshooting and/or correcting the detected condition.

The data storage unit 882 may be used to organize and provide long-term storage for one or more of the collected data, the condition indications, and calculated parameters. In this manner, authorized hospital personnel may access the information at any future date via the communication network 854.

In one embodiment, a web-based software routine may automatically generate, update and maintain a web page within the communication server 892 and/or application server 884, and hosted by the fleet management system 854, that permits an authorized user to view reports on a particular medical cart 100 or on fleet of medical carts 100 (for example, within the user's unit/floor, hospital or hospital group) via the communication network 854, thereby allowing a user to view a report on a medical cart 100 or fleet of medical carts 100 remotely from where that medical cart 100 is located or even remotely from the hospital 858 or hospital system 860. For example, reports, or summaries thereof, may be sent to phones, pagers, electronic mail, the medical cart 100 itself, etc. This may be particularly useful if the report is time critical (e.g., a failure alert). Additionally, or alternatively, the report may include any or all of the collected data from the medical cart(s) 100, the condition indications as generated by the analysis unit 878, parameters calculated by the control unit 880 as may be stored within the data storage unit 882, and serialized subsystem tracking or location (e.g., for recalls, service, etc.). Thus, hospital personnel may be provided with ready access to information about the medical cart(s) 100 within the fleet of medical carts that may not otherwise be readily available locally without undue expenditure and time, or that may not be otherwise available whatsoever without access to the applications 886, data collection unit 876, analysis unit 878, control unit 880 or data storage unit 882 of the fleet management system 852.

It should be understood from the above that the control unit 880 may automatically implement multiple software applications 886, either concurrently or successively, to correct the detected condition. As an example, the control unit 880 may automatically implement a monitoring application based on a detected condition indicating that further analysis is required to pinpoint a condition associated with a medical cart 100. In turn, the control unit 880 may, based on the results of the monitoring application, determine that a particular medical cart needs to be serviced, and may automatically execute the work/service order generation application to schedule service and/or order a replacement part. If desired, the control unit 880 may automatically order the replacement part directly from a supplier via the Internet. In this manner, the fleet management system 852 eliminates the need for a personnel at the hospital 858 to perform these functions manually. Alternatively, an engineering device solution application may be accessed to help the operator choose the correct devices for the application. In turn, the control unit 880 may automatically place the order for the devices.

While FIG. 33 depicts the communication network 854 as a single network such as, for example, the Internet or other public communication network, that links the medical carts 100 to the fleet management system 852 via the communication server 872, a plurality of other network structures or types may be used instead. For example, the medical carts 100 may be communicatively coupled to the fleet management system 852 via a network that may be based on Ethernet or some other protocol or standard.

Figure 34:
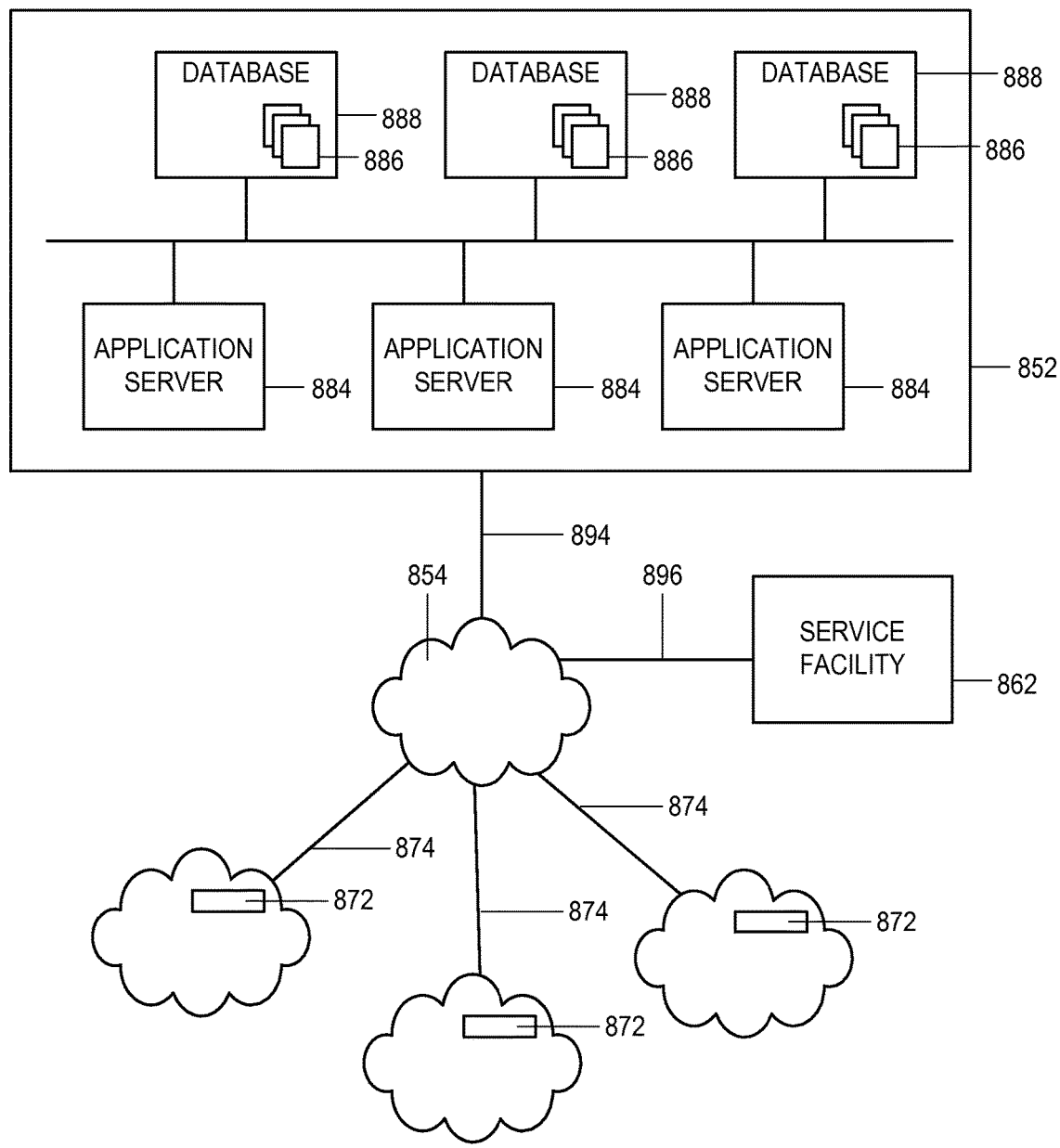
FIG. 34 is an exemplary schematic block diagram of the fleet management system of FIG. 32 that uses Internet-based communications to provide remote services to a plurality medical carts in a plurality of hospitals or hospital systems in accordance with an embodiment.

Referring now to FIG. 34, the fleet management system 852 enables one or more independently operable hospitals 858 or hospital system 860 that are physically remote from each other and from the fleet management system 852 to remotely access a plurality of software applications 886 via the Internet 854. As shown in FIG. 34, the fleet management system 852 may include a plurality of application servers 884 and a plurality of databases 888, all of which are communicatively coupled via a bus 890. Generally speaking, the plurality of application servers 884 may operate as a cluster or server farm, with processing and communications activities distributed across the multiple servers 884. As a result, computing capacity is greatly increased, thus reducing the risk of overwhelming a single server. However, in the event that one server 884 fails, another server in the cluster may function as a backup. Each of the databases 888 and application servers 886 may be located at a single location within the fleet management system 852 or, alternatively, may be located in different geographical locations from each other and/or the fleet management system 852, and adapted to communicate via any suitable communication network. Each of the hospitals or hospital groups 858, 860 may be owned by different business entities. Alternatively, multiple ones of the hospitals 858 may be grouped within a single business entity. In any event, each of the hospitals or hospital groups 858, 860 is communicatively coupled to the Internet 854 via respective communication servers 872 and respective secure communication links 874. In this manner, individual hospitals or hospital groups 858, 860 may independently communicate with the fleet management system 852 over a secure connection, and access data pertaining to their respective medical carts 100 while being restricted from accessing medical cart data of other hospitals, hospital groups, etc. Likewise, the third party provided of the fleet management system 852 may be restricted from some hospital data within the fleet management system 852. For example, the fleet management system 852 may store and transmit data in a secure environment utilizing industry-standard Secure Sockets Layer (SSL) technology providing robust encryption and/or data may be accessed via password protected areas specific to individual customers.

The fleet management system 852 allows the hospitals or hospital groups 858, 860 to have access to a multitude of software applications 886 without having to individually purchase the software applications 886 and associated hardware, software, and other support for the applications 886. Instead, the hospitals or hospital groups 858, 860 may pay a subscription fee to use the services provided by the fleet management system 852. If desired, different levels of service may be sold by the fleet management system 852 to provide different types or numbers of monitoring, diagnostic, and maintenance capabilities to a particular hospital or hospital group. In this manner, different hospitals or hospital groups can subscribe to different levels of services based on their actual needs, size, etc.

Still further, component, material, or other service facility 862 may be communicatively coupled to the Internet 854 via a communication link 896. While FIG. 34 shows the fleet management system 852, the hospitals or hospital groups 858, 860, and the service facility 862 as being communicatively coupled via the Internet 854, it is important to recognize that any other similar open communication network could be used as well.

Generally speaking, the fleet management system 852 provides outsourced or third-party medical cart 100 monitoring, diagnostic, and maintenance services on a subscription basis to a client or customer, such as, for example, one or more of the hospitals or hospital groups 858, 860, via the Internet 854. Therefore, the individual hospitals or hospital groups 858, 860 do not have to acquire the software, hardware, support personnel, etc. associated with the various monitoring, diagnostic, and maintenance applications. In this manner, the relatively high costs associated with building and maintaining the infrastructure of the fleet management system 852 may be shared among the plurality of physically separate hospitals or hospital groups 858, 860 and, if desired, among a plurality of business entities, each of which may be operating one or more hospitals 858 in physically remote locations. Thus, rather than requiring that each hospital or hospital group 858, 860 purchase its own monitoring, diagnostic, and maintenance applications, as well as any updated or revised versions of the applications 886, a hospital or hospital group may be able to cost effectively realize the benefits of having access to such applications.

In practice, the hospitals or hospital groups 858, 860 may have relatively short-term, nonexclusive software licensing agreements with the fleet management system 852. The fleet management system 852 may use the amount of processing time, the number of applications 886 implemented, the type of applications 886 implemented, or any other suitable metric to determine the fees to be charged to any particular customer.

Additionally, in contrast to conventional techniques and systems that typically require special (possibly custom) software and sometimes hardware installed on an end-user's computer to communicate with a medical cart 100, the fleet management system 852 enables remote users or operators to troubleshoot, repair, access information and/or data stored in the data storage unit 882, etc. using conventional internet browser software that is already being executed on virtually any workstation, portable computer, etc.

Thus, support may be provided for remote web based fleet management, monitoring, configuration, analysis, and updates without requiring installation of software on the end-user computers, servers or cart laptops/computers. Further, centralized and consistent visibility into medical cart operations, status and performance may be provided through the continuous collection and transmission of data using the embedded controller 402, and the remote updating of software and firmware may be conducted faster and without conflicts with end-user servers or computers. Likewise, the ability to receive notifications and alerts directly on the medical cart, and to submit service requests directly from the medical cart provides more efficient maintenance. Additionally, the fleet management system 852 may interact with end-user provided laptops or computers installed on the cart, and may build solutions by integrating with other software via API's (application programming interfaces) for external monitoring and analysis of cart features.

Using the above-disclosed systems and methods, operation of the medical cart 100 is independent and segregated from the end-user's computer and servers. Further, in an integrated solution, proactive monitoring may be achieved, such as by analyzing battery and medical cart operational data, and user behavior to proactively identify issues before they lead to decreased performance or service disruptions. Remote access management and monitoring using the fleet management system allows for unique PIN codes assignment to individual medical cart users, changed regularly, updated as users change roles, with appropriate PIN code lengths set based on number of users, and with timeouts configured based on security and user workflow requirements. The configurability of the medical cart allows for adaptation of medical cart parameters and settings to changes in user needs and workflows. Further, enhanced integration of medical cart functions with relevant external software solutions may be achieved, such as, for example, remote unlocking/locking of drawers using medication administration software solutions, transmitting notifications or alerts from existing messaging or paging systems, and receiving service requests into existing service ticket management systems.

The above-disclosed techniques may be implemented using any desired combination of software, firmware and hardware. For example, one or more microprocessors, microcontrollers, application specific integrated circuits (ASICs), etc. may access instructions or data stored on machine or processor accessible storage media to carry out the methods and to implement the apparatus described herein. The storage media may include any combination of devices and/or media such as, for example, solid state storage media including random access memory (RAM), read-only memory (ROM), electrically erasable programmable read-only memory (EEPROM), etc., optical storage media, magnetic storage media, etc.

Thus, while the present disclosure provides specific examples, which are intended to be illustrative only and not to be limiting of the invention, it will be apparent to those of ordinary skill in the art that changes, additions or deletions may be made to the disclosed embodiments without departing from the spirit and scope of the invention.

The invention claimed is:

1. A medical cart comprising:
an embedded controller comprising a computer readable memory and a processor operatively coupled to the memory;
a substantially horizontal work surface;
a touch-sensitive display operatively coupled to the controller and embedded within the work surface such that the touch-sensitive display may be viewed and operated by a user;
a power system operatively coupled to the embedded controller, wherein said power system comprises a battery;
a drawer and an electronically operable locking mechanism operatively coupled to the embedded controller and adapted to electronically lock and unlock the drawer when the drawer is closed;
a light operatively coupled to the embedded controller;
a directional locking caster operatively coupled to the embedded controller;
a lift mechanism configured to raise and lower the work surface; and
a display application stored on the computer readable memory and adapted to be executed by the processor to generate a graphical user interface on the touch-sensitive display, wherein the said graphical user interface comprises an image of a drawer locking control icon, an image of a lighting control icon, an image of a caster lock icon indication indicating whether a direction lock is engaged or disengaged on the directional locking caster, an image of a lift control icon, and an image of power status icon;
wherein the display application enables an operator to select a section of the touch-sensitive display pertaining to the drawer locking control icon to electronically lock or unlock the drawer, and wherein the controller is adapted to cause the locking mechanism to electronically lock or unlock the drawer in response to the operator section;
wherein the display application enables an operator to select a first section of the touch-sensitive display pertaining to the lighting control icon to electronically turn the light on or off, and wherein the controller is adapted to electronically turn the light on or off in response to the operator selection;
wherein the display application enables an operator to select a second section of the touch-sensitive display pertaining to the caster lock icon to electronically lock the directional locking caster, and wherein the controller is adapted to electronically engage or disengage the directional lock of the directional locking caster in response to the operator selection;
wherein the display application enables an operator to select a third section of the touch-sensitive display pertaining to the lift control icon to control raising and lowering of the work surface, and wherein the controller is adapted to raise and lower the work surface in response to the operator selection;
wherein the display application enables an operator to select a fourth section of the touch-sensitive display pertaining to the power status icon to monitor the status of the power system, and wherein the controller is adapted to generate a further display indicating the status of the power system;
wherein the memory is adapted to store a user preference pertaining to at least the height of the work surface and the arrangement of the drawer locking control icon, the lighting control icon, the caster lock icon, and the lift control icon on the graphical user interface, wherein the controller is adapted to initiate the setting on the medical cart automatically when the user logs in.

2. The medical cart of claim 1, further comprising a plurality of lights, wherein the touch-sensitive display comprises an image of a lighting control icon for each light, wherein the display application enables an operator to select a section of the touch-sensitive display pertaining to the lighting control icon to individually turn each light on or off, and wherein the controller is adapted to individually turn each light on or off in response to the operator selection.

3. The medical cart of claim 1, wherein the touch-sensitive display comprises an image of a brightness control icon for the display, wherein the display application enables an operator to select a section of the touch-sensitive display pertaining to the brightness control icon to adjust the brightness of the touch-sensitive display, and wherein the controller is adapted to adjust the brightness of the touch-sensitive display in response to the operator selection.

4. The medical cart of claim 1, further comprising a communication interface stored on the computer readable memory and adapted to be executed by the processor to utilize a first communication system external to the medical cart to communicate with a second communication system located remotely from the first communication system.

5. The medical cart of claim 4, wherein the touch-sensitive display comprises an image to request service for the medical cart, wherein the display application enables an operator to select a section of the touch-sensitive display pertaining to the request and enables the operator to generate a service order, and wherein the communication interface is adapted to communicate the service order to the second communication system via the first communication system.

6. The medical cart of claim 4, wherein the touch-sensitive display comprises an image of a message, wherein the display application enables an operator to select a section of the touch-sensitive display pertaining to the message, and wherein the communication interface is adapted to communicate the message to the second communication system via the first communication system.

7. The medical cart of claim 4, wherein the communication interface is adapted to receive application updates for the medical cart from the second communication system via the first communication system.

8. The medical cart of claim 4, further comprising a data collection application stored on a computer readable memory and adapted to be executed on the processor to collect status information associated with one or more subsystems of the medical cart, wherein the communication interface is adapted to communicate the status information to the second communication system via the first communication system, wherein said subsystems of the medical cart comprise the drawer and locking mechanism, power supply, the directional locking caster, the light, and lift mechanism.

9. The medical cart of claim 8, further comprising an analysis application stored on a computer readable memory and adapted to be executed on the processor to analyze the status information to detect a condition associated with the associated subsystem, wherein the communication interface is adapted to communicate the detected condition to the second communication system via the first communication system.

10. The medical cart of claim 8, wherein the status information pertains to one or more of the group consisting of: power system status, battery status, battery temperature, battery current, battery performance, battery charging, drawer access, faults, sub-system status, communication with the second communication system and user access.

11. The medical cart of claim 4 wherein said embedded controller is configured to receive instructions from a remote user by way of said first and second communications interface and command the locking mechanism to electronically lock or unlock the drawer.

12. The medical cart of claim 1, further comprising a communications bus operatively coupled to the controller and adapted to receive a peripheral sub-system inserted inline into the communications bus, wherein the peripheral sub-system comprises a microcontroller, and wherein the controller is adapted to automatically recognize the peripheral sub-system upon insertion, establish communication with the peripheral sub-system microcontroller, and update the display application to display one or more controls pertaining to the peripheral sub-system.

13. The medical cart of claim 12, wherein the communications bus comprises a control area network (CAN) bus.

14. The medical cart of claim 1 wherein actuation of the control limits movement of the medical cart to either forwards and backwards movement or side to side movement.

15. The medical cart of claim 1 wherein actuation of the control causes a latch to extend horizontally into the caster.

* * * * *

UNITED STATES PATENT AND TRADEMARK OFFICE
CERTIFICATE OF CORRECTION

PATENT NO. : 10,453,572 B1  
APPLICATION NO. : 13/782841  
DATED : October 22, 2019  
INVENTOR(S) : Richard Jason Brooks et al.

Page 1 of 1

It is certified that error appears in the above-identified patent and that said Letters Patent is hereby corrected as shown below:

In the Specification

Column 14, Line 1, please delete "100." and insert --402.--.
Column 24, Line 42, please insert --.-- after 854 and before The.

In the Claims
Column 37, Claim 8, Line 6, please insert --the-- before power supply.
Column 37, Claim 8, Line 7, please insert --the-- before and lift mechanism.

Signed and Sealed this  
Twenty-sixth Day of November, 2019

Andrei Iancu  
*Director of the United States Patent and Trademark Office*